United States Patent [19]
Yamamatsu et al.

[11] Patent Number: 6,040,472
[45] Date of Patent: Mar. 21, 2000

[54] CATALYST FOR USE IN PRODUCING CARBOXYLIC ESTERS

[75] Inventors: Setsuo Yamamatsu, Fuji; Tatsuo Yamaguchi, Shizuoka-ken, both of Japan; Koshiro Yokota, Pasadena, Calif.

[73] Assignee: Asahi Kasei Kogyo Kabushiki Kaisha, Osaka, Japan

[21] Appl. No.: 08/945,308

[22] PCT Filed: Jul. 18, 1996

[86] PCT No.: PCT/JP96/02008

§ 371 Date: Oct. 23, 1997

§ 102(e) Date: Oct. 23, 1997

[87] PCT Pub. No.: WO97/03751

PCT Pub. Date: Feb. 6, 1997

[30] Foreign Application Priority Data

Jul. 18, 1995 [JP] Japan ..................................... 7-181547
Jul. 19, 1995 [JP] Japan ..................................... 7-182721

[51] Int. Cl.$^7$ ............................. C07C 69/74; B01J 31/00
[52] U.S. Cl. ........................... 560/210; 502/102; 560/238
[58] Field of Search ..................... 560/210, 238; 502/102

*Primary Examiner*—Paul J. Killos
*Attorney, Agent, or Firm*—Birch, Stewart, Kolasch & Birch, LLP

[57] ABSTRACT

Disclosed is a novel catalyst for use in producing a carboxylic ester from an aldehyde, an alcohol and molecular oxygen, which comprises a carrier having supported thereon Pd and Pb in a Pd/Pb atomic ratio (S) of $3/0.7 \leq S \leq 3/1.3$, and which exhibits a maximum intensity peak at a diffraction angle ($2\theta$) in the range of from 38.55° to 38.70° in a powder X-ray diffraction pattern thereof, wherein the peak is ascribed to the (111) crystal face diffraction of a Pd—Pb intermetallic compound. The catalyst can be efficiently produced by subjecting a catalyst precursor comprising a carrier having supported thereon a reducible Pd compound or a mixture of a reducible Pd compound and a reducible Pb compound to a reduction treatment in the presence of lead ions and at least one compound selected from a lower fatty acid, an alkali metal salt and an alkaline earth metal salt, or by subjecting a catalyst prepared by a conventional method, which comprises a carrier having supported thereon Pd or a mixture of Pd and Pb, to an activation treatment. By using the catalyst, the desired carboxylic ester can be produced with high selectivity, while suppressing the formation of by-products, even under high temperature and high aldehyde concentration conditions. Further, in the continuous production of a carboxylic ester using the catalyst, stabilization of the catalyst can be effectively performed, so that a desired carboxylic ester can be stably produced with high efficiency and in high yield for a prolonged period of time.

30 Claims, 2 Drawing Sheets

Curve Fitting and Resolution of Overlapping Peaks
  1: Pb4f(7/2) (Pb⁰)
  2: Pb4f(5/2) (Pb⁰)
  3: Pb4f(7/2) (Pbox)
  4: Pb4f(5/2) (Pbox)
  5: X-ray Satellite ascribed to Si2s (MgKα3)
  6: X-ray Satellite ascribed to Si2s (MgKα4)
(Pb⁰: Pb in metallic state; Pbox: Pb in oxidized state)

CATALYST FOR USE IN PRODUCING CARBOXYLIC ESTERS

BACKGROUND OF THE INVENTION

1. Technical Field

The present invention relates to a catalyst for use in producing a carboxylic ester from an aldehyde, an alcohol and molecular oxygen, a method for producing the catalyst, and a method for the production of a carboxylic ester by using the catalyst. More particularly, the present invention is concerned with a novel catalyst which comprises a carrier having supported thereon palladium and lead in a specific atomic ratio, and which exhibits a maximum intensity peak at a diffraction angle (2θ) in a specific range in a powder X-ray diffraction pattern thereof. The present invention is also concerned with a method for producing the catalyst and a method for the continuous production of a carboxylic ester from an aldehyde, an alcohol and molecular oxygen by using the catalyst. In the production of a carboxylic ester using the catalyst of the present invention, the desired carboxylic ester can be obtained with high selectivity even when the reaction is conducted under high temperature and high aldehyde concentration conditions. Further, the catalyst of the present invention exhibits high mechanical strength and high corrosion resistance. In the continuous method for producing a carboxylic ester using the catalyst of the present invention, the desired carboxylic ester can be produced with high efficiency and in high yield for a prolonged period of time.

2. Prior Art

Methods for producing methyl methacrylate or methyl acrylate, which is commercially useful, have already been practiced on a commercial scale. For example, a method for producing methyl methacrylate has been commercially practiced in which methacrolein is oxidized with molecular oxygen to produce methacrylic acid and then, the methacrylic acid produced is reacted with methanol to produce methyl methacrylate. As a result of various attempts for improving catalysts over many years, the yield of methacrylic acid in the above-mentioned step of oxidizing methacrolein has been improved to some extent, namely to a value in the range of from 80% to 85%, which is, however, still unsatisfactory from the commercial viewpoint. Therefore, with respect to the yield of methacrylic acid in the above step, a further improvement has been desired. Further, heteropolyacid catalysts, which are conventionally used in the above reaction for oxidizing methacrolein to produce methacrylic acid, have problems in that they have poor thermal stability, so that the heteropolyacid catalysts are gradually decomposed at the reaction temperatures. It has been reported that improvements have been made in the thermal stability of heteropolyacids. However, it is generally considered that even such improved catalysts are still unsatisfactory in catalytic life when used in commercial practice for the production of methacrylic acid from methacrolein.

On the other hand, a new process for producing methyl methacrylate or methyl acrylate has been attracting attention, in which methacrolein or acrolein is reacted with methanol and molecular oxygen to there-by produce methyl methacrylate or methyl acrylate by a single-step process {hereinafter, methacrolein and acrolein are frequently collectively referred to as "(meth)acrolein", and methyl methacrylate and methyl acrylate are frequently collectively referred to as "methyl (meth)acrylate"}. In this process of reacting (meth)acrolein with methanol and molecular oxygen, it is essential to use a catalyst containing palladium.

Conventionally, the above-mentioned single-step process has a problem in that an aldehyde decomposition reaction occurs as a side reaction to thereby by-produce a hydrocarbon and carbon dioxide gas, so that the yield of a carboxylic ester as the desired product is low. This method is also disadvantageous in that the alcohol undergoes oxidation as a side reaction to by-produce an aldehyde which is different from the aldehyde used as a starting material, and the by-produced aldehyde causes formation of an undesired carboxylic ester which is different from the desired carboxylic ester, so that the selectivity based on the alcohol is also poor (for example, when the alcohol is methanol, methyl formate is by-produced as an undesired carboxylic ester, and when the alcohol is ethanol, methyl acetate is by-produced as an undesired carboxylic ester). Further, there is also a disadvantage that the conventional catalyst cannot maintain its activity for a long period of time. Especially when a commercially valuable process for producing a carboxylic ester from an α·β-unsaturated aldehyde {such as (meth) acrolein} as a starting material, is practiced, a large amount of decomposition products is produced, such as carbon dioxide gas and an olefin (which is propylene when methacrolein is used as a starting material). Thus, this process has not been successfully practiced.

In Examined Japanese Patent Application Publication (Japanese Kokoku) Nos. 57-035856, 57-035857, and 57-035859, the present inventors proposed a catalyst containing palladium and lead, and showed that, in the production of a carboxylic ester using this catalyst, the selectivity for methyl (meth)acrylate based on (meth)acrolein can be largely improved to a level as high as more than 90%. However, with this catalyst, the selectivity for methyl (meth) acrylate is low when the reaction temperature is 50° C. or more, so that it is difficult to produce methyl (meth)acrylate with high economical efficiency.

Subsequently, in Examined Japanese Patent Application Publication (Japanese Kokoku) No. 62-007902, the present inventors proposed a catalyst comprising an intermetallic compound in which palladium and lead are bonded to each other in a simple integral ratio. In this Japanese patent document, the present inventors showed that, in the production of a carboxylic ester using this catalyst, the decomposition of (meth)acrolein is almost completely suppressed, and the catalyst activity can be maintained for a prolonged period of time.

The new single-step process using these new types of catalysts has also an advantage in that the process can be performed in one step, as compared to the conventional two-step process in which a desired carboxylic ester is produced via (meth)acrylic acid and in which the yield of the desired carboxylic ester and the life of the catalyst are still unsatisfactory. Therefore, it has been desired that the new single-step process be commercialized as a new method for producing commercially useful raw materials for various valuable polymers.

However, when the production of, for example, methyl methacrylate (MMA) is conducted, using the above-mentioned new catalysts, under economically advantageous reaction conditions necessary for commercially practicing the new method, i.e., under reaction conditions such that the reaction temperature is as high as 60° C. or more and the methacrolein concentration of the reaction system is as high as 20% or more, not only does the selectivity for MMA become low, but also the by-production of methyl formate due to the oxidation of methanol is sharply increased. For example, Examined Japanese Patent Application Publication (Japanese Kokoku) No. 62-007902 shows that not only can an MMA selectivity exceeding 90% be achieved, but also the by-production of methyl formate is suppressed to a level as low as 0.03 to 0.06 mole/mole of MMA. However, these favorable results can be obtained only when the reaction is conducted under moderate reaction conditions such that the methacrolein concentration of the reaction system is as low as 10% or less and the reaction temperature is as low as 40 to 60° C. When the reaction is conducted under such moderate reaction conditions, the MMA concentration of the resultant reaction mixture is low and, hence, the recycling of a large amount of unreacted methanol inevitably becomes necessary, so that a large amount of vapor becomes necessary for recycling the unreacted methanol. In addition, in this case, since the productivity of the method is low, it is necessary to use a reactor having a large volume. Therefore, this proposal is economically disadvantageous. For obviating the above economical disadvantages of the reaction, it is desired to increase the methacrolein concentration of the reaction system as much as possible and elevate the reaction temperature to a level as high as possible. Examined Japanese Patent Application Publication (Japanese Kokoku) No. 5-069813 shows a reaction example in which the methacrolein concentration of the reaction system is 20% and the reaction temperature is 80° C. However, in this reaction conducted under such high methacrolein concentration and high reaction temperature conditions, it is impossible to obtain a MMA selectivity, based on methacrolein, as high as more than 90%. Further, in this reaction conducted under the above severe reaction conditions, a marked by-production of methyl formate occurs in an amount as large as 0.0923 mole/mole of MMA, which is about 2 times the amount of methyl formate by-produced in the reaction conducted under the above-mentioned moderate reaction conditions. Moreover, when this reaction is conducted under more severe reaction conditions such that the methacrolein concentration is increased up to 30%, a decomposition reaction of methacrolein is likely to occur, so that the MMA selectivity based on methacrolein becomes further lowered.

Palladium is a precious metal and expensive and, hence, when palladium is used as a component for a catalyst, palladium is usually used in the form of a composition comprising a carrier having palladium which is dispersedly supported on the carrier. The selection of an appropriate carrier is extremely important. In Unexamined Japanese Patent Application Laid-Open Specification (Japanese Kokai) Nos. 57-35856, 57-35857, 57-35858, 57-35859 and 57-35860, activated carbon, silica, alumina, calcium carbonate and the like are mentioned as examples of carriers in connection with the method for producing a carboxylic ester by reacting an aldehyde, an alcohol and oxygen in the presence of a palladium-containing catalyst. In order to examine whether or not catalysts employing these carriers can be used for a commercial production process, the present inventors made intensive studies on palladium catalysts employing these carriers. As a result, they found that these catalysts are not completely satisfactory with respect to the catalyst life under the reaction conditions. Specifically, it was found that when the reaction is conducted using an activated carbon-carried palladium catalyst in a slurry form in an agitation type reactor or a bubble column reactor (which is frequently employed in a commercial production process), the activated carbon carrier is unsatisfactory in mechanical strength. Further, it was found that although an alumina carrier has high mechanical strength, an alumina carrier has an inherent disadvantage in that it is corroded with an acidic substance, such as methacrylic acid or acrylic acid, which acidic substance is a typical by-product of the reaction, so that the expensive palladium supported on the alumina carrier is likely to come-off from the carrier. It was also found that a calcium carbonate carrier is more likely to be corroded with an acidic substance than an alumina carrier and, hence, is unsuitable for use in a commercial production process. With respect to a silica carrier, an unfavorable phenomenon was observed such that the silica carrier is gradually corroded with water present in the reaction system, causing the silica to be dissolved out in the reaction system. Thus, this suggests that a silica carrier cannot be stably used for a long period of time. Further, it was found that a silica carrier has poor mechanical strength, as compared to an alumina carrier. As apparent from the above, a catalyst carrier which has not only high mechanical strength and high physical stability, but also high chemical stability such that it is not susceptible to corrosion with water, an acidic substance and an alkaline substance, has not yet been proposed.

It has been reported that, in an attempt to improve the mechanical strength and hydrolysis resistance of a silica carrier, a silica gel is modified by, for example, changing the production method of a silica gel or subjecting a silica gel to sintering. However, there is no report that both of the mechanical strength and hydrolysis resistance of a silica carrier can be improved simultaneously without impairing the desired properties of the catalyst using the silica carrier. For example, it is known that quartz, which is one type of silica, is hard and has both high mechanical strength and high hydrolysis resistance. However, quartz has a small specific surface area (1 $m^2/g$ or less). Therefore, quartz cannot support a metal thereon in the form of well dispersed fine particles, so that a catalyst using quartz as a carrier has extremely low reaction activity per unit weight. For this reason, it is difficult to use quartz as a carrier in a catalyst.

As described hereinabove, a material for a carrier to be used in a catalyst is required to have properties such that it not only maintains a large specific surface area for a satisfactorily long period of time, but also has both high mechanical strength and high corrosion resistance to a liquid corrosive substance inherent in the reaction for producing a carboxylic ester. Conventionally, a carrier satisfying all of these requirements has not been known. Therefore, for achieving the economic improvement of the reaction, it has been desired to develop a catalyst which not only can be used for producing a desired carboxylic ester (e.g., MMA) with a selectivity as high as more than 90% even when the reaction is conducted under high temperature and high aldehyde concentration conditions, while suppressing the production of by-products (such as methyl formate), but also has both high mechanical strength and high corrosion resistance.

SUMMARY OF THE INVENTION

In these situations, the present inventors have made extensive and intensive studies on catalyst systems containing palladium and lead, with a view toward developing a catalyst which can be used for producing a desired carboxylic ester with high selectivity even when the reaction is conducted under high temperature and high aldehyde concentration conditions, while suppressing the production of an alcohol-derived by-product (such as methyl formate). Specifically, the present inventors focused their attention on a specific Pd—Pb intermetallic compound having a Pd/Pb atomic ratio of 3/1, i.e., $Pd_3Pb_1$, among the intermetallic compounds (comprising palladium and lead bonded to each other in a simple integral ratio) which compounds had been proposed by the present inventors in Examined Japanese Patent Application Publication (Japanese Kokoku) No. 62-007902, and the present inventors have made intensive studies on the atomic ratio, catalyst properties and the like of the specific intermetallic compound. As a result, the present inventors have unexpectedly found that, in a method for producing a carboxylic ester from an aldehyde, an alcohol and molecular oxygen, when use is made of a catalyst which comprises a carrier having supported thereon palladium and lead in a Pd/Pb atomic ratio of from 3/0.7 to 3/1.3, and which exhibits a maximum intensity peak at a diffraction angle (2θ) in the range of from 38.55° to 38.70° in a powder X-ray diffraction pattern thereof, wherein the peak is ascribed to the (111) crystal face diffraction of a Pd—Pb intermetallic compound, not only can a carboxylic ester be produced with high selectivity even when the reaction is conducted under high temperature and high aldehyde concentration conditions (high temperature and high aldehyde concentration conditions are effective for improving the productivity of a desired carboxylic ester), but also the production of an alcohol-derived by-product, such as methyl formate, is effectively suppressed. The present inventors have also found a method for producing the novel catalyst with certainty and with high efficiency. The present invention has been completed, based on these findings.

Accordingly, a primary object of the present invention is to provide a catalyst for use in a carboxylic ester production method comprising reacting an aldehyde, an alcohol and molecular oxygen, wherein the catalyst comprises a specific catalyst containing palladium and lead, and enables not only a desired carboxylic ester to be produced with high selectivity even when the reaction is conducted at high temperature and high aldehyde concentration conditions (high temperature and high aldehyde concentration conditions are effective for improving the productivity of a desired carboxylic ester), but also the production of an alcohol-derived by-product, such as methyl formate, to be effectively suppressed.

It is another object of the present invention to provide a method for producing the above-mentioned catalyst.

It is a further object of the present invention to provide a method for the production of a carboxylic ester by using the above-mentioned catalyst, especially a continuous method for the production of a carboxylic ester wherein deterioration of the catalyst is suppressed.

The foregoing and other objects, features and advantages of the present invention will be apparent from the following detailed description and claims, taken in connection with the accompanying drawings.

DETAILED DESCRIPTION OF THE INVENTION

Figure 1:
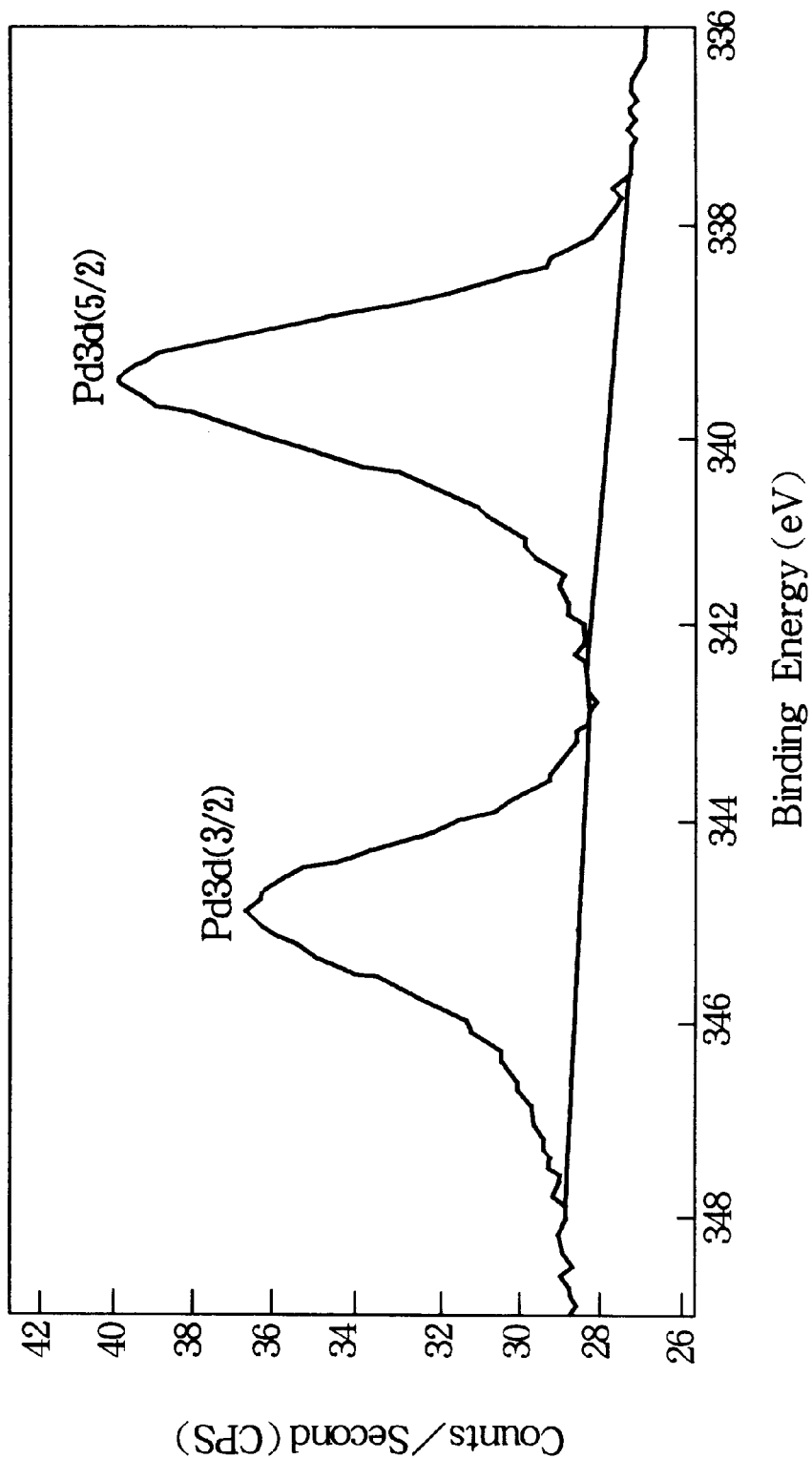
FIG. 1 shows a spectrum obtained from metallic palladium by X-ray photoelectron spectroscopy, showing peaks ascribed to the Pd(3d) electrons of metallic palladium.

In one aspect of the present invention, there is provided a catalyst for use in producing a carboxylic ester from an aldehyde, an alcohol and molecular oxygen, which comprises a carrier having supported thereon palladium and lead in a Pd/Pb atomic ratio (S) of $3/0.7 \leq (S) \leq 3/1.3$, the catalyst exhibiting a maximum intensity peak at a diffraction angle (2θ) in the range of from 38.55° to 38.70° in a powder X-ray diffraction pattern thereof, wherein the peak is ascribed to the (111) crystal face diffraction of a Pd—Pb intermetallic compound.

For an easy understanding of the present invention, the essential features and various preferred embodiments of the present invention are enumerated below.

1. A catalyst for use in producing a carboxylic ester from an aldehyde, an alcohol and molecular oxygen, which comprises a carrier having supported thereon palladium and lead in a Pd/Pb atomic ratio (S) of $3/0.7 \leq S \leq 3/1.3$, the catalyst exhibiting a maximum intensity peak at a diffraction angle (2θ) in the range of from 38.55° to 38.70° in a powder X-ray diffraction pattern thereof, wherein the peak is ascribed to the (111) crystal face diffraction of a Pd—Pb intermetallic compound.

2. The catalyst according to item 1 above, exhibiting, in a spectrum obtained from the catalyst by X-ray photoelectron spectroscopy, a ratio of from 1/0.2 to 1/0.7 in terms of the $\{Pd3d(3/2)+Pd3d(5/2)\}/\{Pb4f(7/2)\times1.75\}$ ratio of the sum of respective intensities of two peaks respectively ascribed to the 3d(3/2) electron and the 3d(5/2) electron of metallic palladium to the intensity of a peak ascribed to the 4f(7/2) electron of metallic lead which is multiplied by 1.75.

3. The catalyst according to item 1 or 2 above, wherein the carrier is an aluminum-containing silica composition comprising silica and alumina, which has an aluminum proportion of from 1 to 30 mol. %, based on the total molar amount of silicon and aluminum in the composition.

4. The catalyst according to item 1 or 2 above, wherein the carrier comprises a silica-alumina-magnesia composition having silicon, aluminum and magnesium proportions of from 42 to 90 mol. %, from 5.5 to 38 mol. %, and from 4 to 38 mol. %, respectively, based on the total molar amount of the silicon, the aluminum and the magnesium.

5. The catalyst according to item 1 or 2 above, wherein the carrier comprises a crystalline metallosilicate which, in the anhydride state and on a molar basis, has a composition represented by the following formula (1);

$$xM_{2/n}O \cdot ySiO_2 \cdot R_{2/w}O \qquad (1)$$

wherein:

M represents at least one cation having the valence of n;

R represents at least one metal having the valence of w, which is selected from metals belonging to Groups IB, IIB, IIIA, IIIB, IVA, IVB, VA, VB, VIB, VIIB and VIII of the short-form Periodic Table;

n is 1 or 2;

w is an integer of from 1 to 4;

x=0.3=0.1; and $0.5 \leq y \leq 500$.

6. A method for producing a catalyst of item 1 above, which comprises subjecting a catalyst precursor comprising a carrier having supported thereon a reducible palladium compound or a mixture of a reducible palladium compound and a reducible lead compound to a reduction treatment with a reducing agent in a solvent in the presence of lead ions and at least one compound selected from the group consisting of a $C_1$–$C_5$ fatty acid, an alkali metal salt and an alkaline earth metal salt.

7. The method according to item 6 above, wherein the reducible palladium compound is at least one salt selected from palladium salts of organic acids and inorganic acids, and the reducible lead compound is at least one salt selected from lead salts of organic acids and inorganic acids.

8. The method according to item 6 or 7 above, wherein the alkali metal salt is an alkali metal salt of a $C_1$–$C_5$ fatty acid, and the alkaline earth metal salt is an alkaline earth metal salt of a $C_1$–$C_5$ fatty acid.

9. The method according to any one of items 6 to 8 above, wherein the reducing agent comprises at least one member selected from the group consisting of formaldehyde, formic acid, hydrazine, methanol and molecular hydrogen.

10. The method according to any one of items 6 to 9 above, wherein the solvent comprises at least one member selected from the group consisting of water and an alcohol.

11. A method for producing a catalyst of item 1 above, which comprises subjecting a catalyst intermediate comprising a carrier having supported thereon palladium or a mixture of palladium and lead in a Pd/Pb atomic ratio (S) of $3/0 \leq S \leq 3/10$ to a reduction treatment with a reducing agent in the presence of lead ions in a solvent.

12. The method according to item 11 above, wherein the reduction treatment is conducted in the presence of at least one compound selected from the group consisting of a $C_1$–$C_5$ fatty acid, an alkali metal salt of a $C_1$–$C_5$ fatty acid and an alkaline earth metal salt of a $C_1$–$C_5$ fatty acid.

13. The method according to item 11 or 12 above, wherein the reducing agent comprises at least one member selected from the group consisting of formaldehyde, formic acid, hydrazine, methanol and molecular hydrogen.

14. The method according to any one of items 11 to 13 above, wherein the solvent comprises at least one member selected from the group consisting of water and an alcohol.

15. A method for producing a catalyst of item 1 above, which comprises oxidizing a catalyst intermediate comprising a carrier having supported thereon palladium and lead in a Pd/Pb atomic ratio (S) of $3/0.7 \leq S \leq 3/1.3$ with a gaseous oxidizing agent and subsequently reducing the resultant oxidized catalyst intermediate with a gaseous reducing agent, wherein a sequence of the oxidation and the reduction is conducted at least once.

16. The method according to item 15 above, wherein the gaseous oxidizing agent comprises molecular oxygen.

17. The method according to item 15 or 16 above, wherein the gaseous reducing agent comprises at least one member selected from methanol gas, molecular hydrogen and $C_2$–$C_4$ olefin gas.

18. A method for producing a catalyst of item 1 above, which comprises oxidizing a catalyst intermediate comprising a carrier having supported thereon palladium and lead in a Pd/Pb atomic ratio (S) of $3/1.3 < S \leq 3/10$ with a gaseous oxidizing agent and subsequently reducing the oxidized catalyst intermediate with a gaseous reducing agent, wherein a sequence of the oxidation and the reduction is conducted at least once; and, subsequent to the sequence of the oxidation and the reduction which sequence is conducted at least once, treating the resultant catalyst intermediate with a solution of at least one compound selected from the group consisting of a $C_1$–$C_5$ fatty acid, an alkali metal salt of a $C_1$–$C_5$ fatty acid and an alkaline earth metal salt of a $C_1$–$C_5$ fatty acid in a solvent.

19. The method according to item 18 above, wherein the gaseous oxidizing agent comprises molecular oxygen.

20. The method according to item 18 or 19 above, wherein the gaseous reducing agent comprises at least one member selected from methanol gas, molecular hydrogen and $C_2$–$C_4$ olefin gas.

21. The method according to any one of items 18 to 20 above, wherein the solvent comprises at least one member selected from the group consisting of water and an alcohol.

22. A method for producing a catalyst of item 1 above, which comprises treating a catalyst intermediate comprising a carrier having supported thereon palladium and lead in a Pd/Pb atomic ratio (S) of $3/2.5 \leq S \leq 3/10$ with a solution of at least one compound selected from the group consisting of a $C_1$–$C_5$ fatty acid, an alkali metal salt of a $C_1$–$C_5$ fatty acid and an alkaline earth metal salt of a $C_1$–$C_5$ fatty acid in a solvent.

23. The method according to item 22 above, wherein the solvent comprises at least one member selected from the group consisting of water and an alcohol.

24. A method for producing the catalyst of item 1 above, which comprises reacting, in a reactor, a catalyst intermediate comprising a carrier having supported thereon palladium or a mixture of palladium and lead in a Pd/Pb atomic ratio (S) of $3/0 \leq S \leq 3/10$ with an alcohol or a mixture of an alcohol and an aldehyde in the presence of lead ions, wherein the reaction is conducted under conditions such that the partial pressure of oxygen at the outlet of the reactor is from 0 to 0.8 kg/cm$^2$.

25. A method for producing the catalyst of item 2 above, which comprises reacting, in a reactor, a catalyst intermediate comprising a carrier having supported thereon palladium or a mixture of palladium and lead in a Pd/Pb atomic ratio (S) of $3/0 \leq S \leq 3/10$ with an alcohol or a mixture of an alcohol and an aldehyde in the presence of lead ions, wherein the reaction is conducted under conditions such that the partial pressure of oxygen at the outlet of the reactor is from 0 to 0.4 kg/cm$^2$.

26. A method for producing the catalyst of item 2 above, which comprises reacting, in a reactor, the catalyst of item 1 above with an alcohol or a mixture of an alcohol and an aldehyde in the presence of lead ions, wherein the reaction is conducted under conditions such that the partial pressure of oxygen at the outlet of the reactor is from 0 to 0.8 kg/cm$^2$.

27. A method for continuously producing a carboxylic ester, which comprises continuously reacting an aldehyde, an alcohol and molecular oxygen in a reactor in the presence of the catalyst of any one of items 1 to 5 above, while adding to the reactor a substance capable of forming lead ions in a reaction system comprising the aldehyde, the alcohol and the molecular oxygen.

28. The method according to item 27 above, wherein the continuous reaction is conducted under conditions such that the partial pressure of oxygen at the outlet of the reactor is 0.8 kg/cm$^2$ or less.

29. The method according to item 27 or 28 above, wherein the molecular oxygen is in the form of air.

30. A method according to any one of items 27 to 29 above, wherein the aldehyde is selected from the group consisting of methacrolein, acrolein and a mixture thereof, and the alcohol is methanol.

The present invention is described below in detail.

In the present invention, the term "catalyst precursor" means a composition comprising a carrier having supported thereon a reducible palladium compound or a mixture of a reducible palladium compound and a reducible lead compound, which composition is used as a starting material in one mode of the method for producing the catalyst of the present invention.

In the present invention, the term "catalyst intermediate" means a catalyst composition comprising a carrier having supported thereon palladium or a mixture of palladium and lead in a Pd/Pb atomic ratio (S) of 3/0 to 3/10, which does not satisfy all or part of the essential requirements of the catalyst of the present invention, and which is subjected to an activation treatment to thereby produce the catalyst of the present invention. Examples of catalyst intermediates include a conventional catalyst prepared by a known method, and a spent catalyst which originally satisfied the essential requirements of the catalyst of the present invention, but has become deteriorated as a result of use in the reaction of producing a desired carboxylic ester, so that it no longer satisfies a part or all of the requirements of the catalyst of the present invention.

In the present invention, the term "activation" means any of various processes for modifying or altering the above-mentioned "catalyst intermediate" so as to obtain a catalyst satisfying all of the essential requirements of the catalyst of the present invention.

In the present invention, the term "high quality" is used for identifying a catalyst containing a palladium/lead intermetallic compound ($Pd_3Pb_1$) which has a substantially ideal crystal lattice having no or only few lattice defects. The term "low quality" is used for identifying a catalyst containing a palladium/lead intermetallic compound which has many defects in the crystal lattice.

In the present invention, the term "high purity" is used for identifying a catalyst which has an extremely small content of impurity lead values which are lead values other than those of a palladium/lead intermetallic compound ($Pd_3Pb_1$) contained in the catalyst, such as a lead oxide and metallic lead, and in which catalyst substantially all of the metal values are those of the palladium/lead intermetallic compound. The term "low purity" is used for identifying a catalyst having a large content of the above-mentioned impurity lead values.

When a catalyst has a "low quality" or a "low purity", such a catalyst exhibits very poor catalytic performance, such as very low selectivity for a desired carboxylic ester (e.g., MMA), as compared to the catalyst of the present invention.

When the catalysts disclosed in Examined Japanese Patent Application Publication (Japanese Kokoku) No. 62-007902 are used for the production of a carboxylic ester wherein the reaction is conducted under severe reaction conditions, namely, under high reaction temperature and high aldehyde concentration conditions, the selectivity for a desired carboxylic ester, such as MMA, becomes poor. The present inventors have made intensive researches on the reason for the poor selectivity exhibited in the reaction using the catalysts of the above-mentioned Japanese Patent document. As a result, the present inventors have found that the reason for the poor selectivity resides in that the catalysts of the above-mentioned Japanese patent document contain a large amount of impurities, such as a lead compound (e.g. lead oxide) and/or metallic lead, and have a very low purity with respect to $Pd_3Pb_1$. For example, the catalyst of Example 1 of the above-mentioned Examined Japanese Patent Application Publication No. 62-007902 has been prepared in such a manner as gives a Pd/Pb atomic ratio of 3/1.5. It is presumed that, in this catalyst, 0.5 lead atom per molecule of the intermetallic compound is supported on the carrier in the form of a lead compound (such as lead oxide) and/or metallic lead, and that the presence of the lead compound and/or metallic lead as impurities largely lowers the purity of $Pd_3Pb_1$. Further, the catalyst of Example 4 of the above-mentioned Japanese patent document has been prepared in such a manner as gives a Pd/Pb atomic ratio of 3/3, and contains 2 lead atoms in the form of impurities per molecule of the intermetallic compound and, hence, the purity of $Pd_3Pb_1$ is even lower than the catalyst of Example 1 of the same Japanese patent document. In other words, the catalysts of the above-mentioned Japanese patent document have extremely low purity, that is, these catalysts contain lead values not participating in the formation of $Pd_3Pb_1$ in an amount as large as 50 to 200%, based on the number of the lead atoms participating in the formation of $Pd_3Pb_1$. The present inventors have found that the presence of such lead-containing impurities is the main reason why the selectivity for a desired carboxylic ester is low when the reaction for producing the carboxylic ester is conducted using the catalysts of Examined Japanese Patent Application Publication no. 62-007902 under severe reaction conditions, namely, under high reaction temperature and high aldehyde concentration conditions.

The present inventors have made further studies and made various attempts to produce a catalyst containing palladium and lead in a Pd/Pb atomic ratio which is as close to 3/1 as possible and to reduce the amount of lead-containing impurities in the catalyst to a level as small as possible. However, the present inventors have found that even when a catalyst is produced in a manner such that the Pd/Pb atomic ratio becomes 3/1 by the conventional production method of a Pd/Pb-supporting catalyst, only a low quality Pd/Pb-supporting catalyst having many lattice defects can be obtained, and that when the reaction for producing a carboxylic ester is conducted using such a low quality Pd/Pb-supporting catalyst, the selectivity for the desired carboxylic ester becomes largely lower rather than the selectivity achieved in the reaction conducted using the catalysts of Examined Japanese Patent Application Publication No. 62-007902. In other words, conventionally, an ideal catalyst has not been obtained which not only carries, as a catalyst active species, a high quality $Pd_3Pb_1$ having no or only few lattice defects, but also has an advantage such that the amount of lead-containing impurities is very small.

The present inventors have made still further studies on how to form, on a carrier, a high quality intermetallic compound $Pd_3Pd_1$ having the stoichiometric atomic ratio, without using an excess amount of lead. As a result, they have found that the step of reducing a reducible palladium compound is important for attaining the objective. Specifically, the present inventors have found that, as described in detail below, a $Pd_3Pd_1$ crystal having no or only few lattice defects can be almost stoichiometrically produced by subjecting a catalyst precursor comprising a carrier having supported thereon a reducible palladium compound or a mixture of a reducible palladium compound and a reducible lead compound to a reduction treatment in a solvent in the presence of lead ions and at least one member selected from a lower fatty acid, alkali metal ions and alkaline earth metal ions, with a reducing agent, such as formaldehyde, formic acid, hydrazine, methanol or molecular hydrogen. The mechanism for this result has not yet been elucidated. However, it is presumed that a reducible palladium compound is successively reduced to form metallic Pd having activated hydrogen formed thereon and, then, the activated hydrogen reduces a Pb ion to form metallic Pb, thereby successively forming $Pd_3Pb_1$, enabling the stable growth of a $Pd_3Pd_1$ crystal. It is also presumed that the presence of at least one member selected from a lower fatty acid, alkali metal ions and alkaline earth metal ions improves the selectivity for the formation of $Pd_3Pb_1$ in the reaction between Pd and Pb. Thus, the present inventors have succeeded in production of a catalyst which contains a Pd—Pb intermetallic compound of a $Pd_3Pb_1$ structure having no or only few lattice defects, without using an excess amount of lead.

Accordingly, in one mode of the method of the present invention for producing the catalyst of the present invention, a catalyst precursor comprising a carrier having supported thereon a reducible palladium compound or a mixture of a reducible palladium compound and a reducible lead compound is subjected to a reduction treatment in a solvent system composed of water and/or alcohol in the presence of lead ions and at least one compound selected from the group consisting of a $C_1$–$C_5$ fatty acid, an alkali metal salt and an alkaline earth metal salt, thereby obtaining a catalyst containing, with high purity, a high quality $Pd_3Pb_1$ intermetallic compound having no or only few lattice defects. As described above, the obtained catalyst has advantages such that, in the production of a carboxylic ester using this catalyst, the desired carboxylic ester can be obtained with high selectivity even when the reaction is conducted under severe reaction conditions, namely, under high reaction temperature and high aldehyde concentration conditions. As described above, herein, the term "catalyst precursor" means a composition comprising a carrier having supported thereon reducible compound(s) of metal(s) which provides catalyst active sites, that is, the term means a composition which becomes a metallic catalyst upon being subjected to reduction.

Further, the present inventors have also found that an ideal catalyst comprising a carrier having supported thereon $Pd_3Pb_1$ having no or only few lattice defects, in which the amount of lead-containing impurities is suppressed to a very low level, can also be obtained by subjecting to the below-described activation treatment a Pd—Pb intermetallic compound-containing catalyst which does not satisfy a part or all of the essential requirements of the catalyst of the present invention, i.e., the requirement of having high purity and the requirement of having high quality. As described in detail below, by conducting the below-described activation treatment, lattice defects of a $Pd_3Pb_1$ can be easily decreased without increasing the amount of lead-containing impurities, such as an undesired lead compound (e.g. lead oxide) and/or metallic lead, so that a high quality $Pd_3Pb_1$ can be obtained. That is, it has become possible to obtain a catalyst comprising a carrier having supported thereon a high quality $Pd_3Pb_1$ with high purity. Further, it has been found that, in the production of a carboxylic ester using this catalyst, the desired carboxylic ester can be obtained with high selectivity even when the reaction is conducted under severe reaction conditions.

It is also requisite that the catalyst of the present invention comprise a carrier having supported thereon palladium and lead in a Pd/Pb atomic ratio (S) of $3/0.7 \leq S \leq 3/1.3$. It is preferred that the Pd/Pb atomic ratio (S) be in the range of $3/0.9 \leq S \leq 3/1.1$. When the proportion of lead in the above-mentioned Pd/Pb atomic ratio exceeds 1.3, there is a problem such that, in the reaction using the catalyst, the production of by-products, such as methyl formate, is largely increased. When the proportion of lead in the above-mentioned Pd/Pb atomic ratio is less than 0.7, there is a problem such that, in the reaction using the catalyst, the decomposition of aldehyde is increased, so that the selectivity for the desired carboxylic ester, such as MMA, becomes largely lowered. It is desired that the Pd/Pb atomic ratio be as close to 3/1 as possible.

It is requisite that the catalyst of the present invention exhibit a maximum intensity peak at a diffraction angle ($2\theta$) in the range of from 38.55° to 38.70° in a powder X-ray diffraction pattern thereof, wherein the peak is ascribed to the (111) crystal face diffraction of a Pd—Pb intermetallic compound. When the maximum intensity peak is exhibited at a diffraction angle ($2\theta$) smaller than 38.55°, there is a problem such that, in the carboxylic ester production reaction using the catalyst, the production of by-products, such as methyl formate, is largely increased. When the maximum intensity peak is exhibited at a diffraction angle ($2\theta$) larger than 38.70°, the decomposition of aldehyde is increased, so that the selectivity for the desired carboxylic ester, such as MMA, becomes largely lowered.

When the catalyst of the present invention, which satisfies both of the above-mentioned Pd/Pb atomic ratio requirement and diffraction angle ($2\theta$) requirement, is used for the production of a carboxylic ester, the selectivity for the desired carboxylic ester, such as MMA, can be improved to a level as high as more than 90%. This effect is important especially when the reaction is conducted under commercially advantageous reaction conditions, namely, under high reaction temperature and high aldehyde concentration conditions.

Among catalysts of the present invention which comprise a carrier having supported thereon a high-quality $Pd_3Pb_1$ with high purity, especially preferred is a catalyst having a surface structure and a surface composition, both of which are precisely controlled so as to exhibit, in a spectrum obtained from the catalyst by X-ray photoelectron spectroscopy, a ratio of from 1/0.2 to 1/0.7 in terms of the $\{(Pd3d(3/2)+Pd3d(5/2)\}/\{Pb4f(7/2)\times 1.75\}$ ratio of the sum of respective intensities of two peaks respectively ascribed to the 3d(3/2) electron and the 3d(5/2) electron of metallic palladium to the intensity of a peak ascribed to the 4f(7/2) electron of metallic lead which is multiplied by 1.75. It has been found that such a catalyst having a surface structure and a surface composition, both of which are precisely controlled so as to exhibit the above-mentioned X-ray photoelectron spectroscopic characteristics, is advantageous not only in that, in the reaction using the catalyst, even when the reaction is conducted under severe reaction conditions, namely, under high reaction temperature and high aldehyde concentration conditions, the production of by-products, such as methyl formate, can be suppressed to a low level and the selectivity for a desired carboxylic ester is high, but also in that the conversion of aldehyde is high even when the reaction is conducted under severe reaction conditions.

The analysis of the catalyst by X-ray photoelectron spectroscopy is effective for investigating the surface portion of the catalyst (a surface portion having a depth of about 10 Å), and the ratio of metallic palladium to metallic lead can be calculated from the ratio of the total intensity (area) of two peaks for metallic palladium to the intensity (area) of a peak for metallic lead. When the above peak intensity ratio of metallic palladium to metallic lead is within the above-mentioned range, the catalyst of the present invention exhibits further improved catalyst properties as mentioned above.

Specifically, it has unexpectedly been found that, when the surface structure and surface composition of the catalyst containing $Pd_3Pd_1$ as a catalyst active species are precisely controlled so as to exhibit the above-mentioned specific characteristics in the X-ray photoelectron spectrum, the selectivity for the desired carboxylic ester is improved not only on an aldehyde basis, but also on an alcohol basis. When use is made of the catalyst of the present invention having its surface structure and surface composition precisely controlled so as to exhibit, in a spectrum obtained from the catalyst by X-ray photoelectron spectroscopy, a ratio of from 1/0.2 to 1/0.7 in terms of the {Pd3d(3/2)+Pd3d(5/2)}/{Pb4f(7/2)×1.75} ratio of the sum of respective intensities of two peaks respectively ascribed to the 3d(3/2) electron and the 3d(5/2) electron of metallic palladium to the intensity of a peak ascribed to the 4f(7/2) electron of metallic lead which is multiplied by 1.75, not only is there the advantage that the desired carboxylic ester can be obtained with high selectivity and the production of by-products, such as methyl formate, can be suppressed to a low level even when the reaction is conducted under severe reaction conditions, namely, under high reaction temperature and high aldehyde concentration conditions, but also there is the advantage that the conversion of aldehyde is high even when the reaction is conducted under severe reaction conditions.

The reason why, by the use of the catalyst exhibiting the above-mentioned specific X-ray photoelectron spectroscopic characteristics, the above-mentioned advantages that the production of by-products, such as methyl formate, can be suppressed to a low level, that the selectivity for a desired carboxylic ester is high, and further that the conversion of aldehyde is high even under severe reaction conditions can be achieved, has not yet been elucidated. However, the following presumption has been made. Lead has a low oxidation-reduction potential and hence is susceptible to oxidation-reduction. However, when the surface structure and surface composition of the catalyst are precisely controlled so as to exhibit the above-mentioned specific X-ray photoelectron spectroscopic characteristics, the lead atoms in $Pd_3Pd_1$ are stabilized, so that the excellent properties of $Pd_3Pd_1$ as a catalyst active species are fully exerted.

Further, when the catalyst of the present invention exhibits, in a spectrum obtained from the catalyst by X-ray photoelectron spectroscopy, a ratio of from 1/0 to 1/0.2 in terms of the {Pd3d(3/2)+Pd3d(5/2)}/{electrically charged lead} ratio of the sum of respective intensities of two peaks respectively ascribed to the 3d(3/2) electron and the 3d(5/2) electron of metallic palladium to the intensity of a peak ascribed to electrically charged lead, there is an advantage that, in the reaction using the catalyst, the production of by-products, such as methyl formate, can be further suppressed. It is desired that the above-mentioned {Pd3d(3/2)+Pd3d(5/2)}/{electrically charged lead} ratio be as close to 1/0 as possible.

I. Carrier

[I-A] Preferred Carrier

With respect to a carrier to be used in the catalyst of the present invention, there is no particular limitation. However, it is preferred to use an aluminum-containing silica type carrier, a silica-alumina-magnesia type carrier or a crystalline aluminosilicate type carrier, because each of these three types of carriers has advantageously high mechanical strength.

Hereinbelow, an explanation is made on the mechanism of the achievement of such a high mechanical strength of each of the above-mentioned three types of carriers, which mechanical strength contributes to the prolonged life of the catalyst of the present invention. The reason why these carriers have such a high mechanical strength is believed to be as follows. With respect to the aluminum-containing silica type carrier, it is believed that this type of carrier has a high mechanical strength due to the following reasons. When aluminum (Al) is added to a non-crosslinked silica (Si—O) chain present in a silica gel, to thereby form an Si—O—Al—O—Si bond, it is advantageous not only in (i) that the stability to acidic substances which is inherent in the Si—O chain is not impaired, but also in (ii) that the Si—O chains are strongly bonded together due to the formation of an Al-crosslinked structure, so that the hydrolysis resistance (hereinafter, frequently, simply referred to as "water resistance") of the silica gel is greatly improved. Further, the formation of the Si—O—Al—O—Si crosslink structure is advantageous in (iii) that the amount of the non-crosslinked Si—O chains becomes smaller than in the case of a simple silica gel having no Al-crosslinked structure, so that the mechanical strength of the Al-crosslinked silica gel is greatly improved. That is, it is believed that the increase in the amount of the Si—O—Al—O—Si bonds formed contributes to the improvement in the mechanical strength and the water resistance of the alumina-containing silica type carrier.

With respect to the silica-alumina-magnesia type carrier, it is believed that this type of carrier has a high mechanical strength due to the following reasons. When magnesium is present together with the above-mentioned Si—O—Al—O—Si structure, it is advantageous in (iv) that the electric charge formed in the Si—O—Al—O—Si structure due to the difference in valence between Si (which is tetravalent) and Al (which is trivalent) is compensated and neutralized by the presence of magnesium (which is divalent). Therefore, the silica-alumina-magnesia type carrier has a good balance in electric charge due to the presence of the above three components, so that it is advantageous in (v) that this type of carrier has a further improved stability in structure. That is, the silica-alumina-magnesia type carrier exhibits substantially neutral properties, contrary to the silica-alumina carrier which exhibits acidic properties Therefore, it can be presumed that when this silica-alumina-magnesia type carrier is used in a catalyst, the formation of a by-produced acetal, which vigorously occurs under acidic conditions, can be advantageously suppressed due to the neutral properties of the silica-alumina-magnesia type carrier.

Another type of carrier which can be preferably used in the present invention is a carrier comprising a crystalline metallosilicate which, in the anhydride state and on a molar basis, has a composition represented by the following formula (1);

$$xM_{2/n}O \cdot ySiO_2 \cdot R_{2/w}O \qquad (1)$$

wherein:

M represents at least one cation having the valence of n;

R represents at least one metal having the valence of w, which is selected from metals belonging to Groups IB, IIB, IIIA, IIIB, IVA, IVB, VA, VB, VIB, VIIB and VIII of the short-form Periodic Table;

n is 1 or 2;

w is an integer of from 1 to 4;

x=0.3±0.1; and 0.5≦y≦500.

With respect to the above-mentioned crystalline metallosilicate which comprises a regularly constructed chain structure, it is considered that when, for example, R in formula (1) above is Al, a crystalline structure comprising a regularly constructed chain structure: Si—O—Al—O—Si is formed, so that the amount of non-crosslinked sites in the crystalline metallosilicate is small. For this reason, it is considered that the crystalline metallosilicate type carrier has a markedly improved resistance to hydrolysis.

Further, as mentioned above, it is considered that a carrier having the Si—O—Al—O—Si crosslink structure has improved mechanical strength as compared to the carrier comprising a simple silica gel. Therefore, it is considered that the crystalline metallosilicate type carrier has improved mechanical strength and water resistance due to the formation of the Si—O—Al—O—Si crosslink structure and crystalline structure comprising the above crosslink structure.

With respect to the cation M, it is considered that the electric charge formed in the Si—O—Al—O—Si structure due to the difference in valence between Si (which is tetravalent) and Al (which is trivalent) is compensated and neutralized by the presence of the cation M. Therefore, this crystalline metallosilicate type carrier has a good balance in electric charge due to the presence of the above three components, so that this type of carrier has a further improved stability in crystal structure.

On the other hand, as mentioned above, a conventional silica-alumina carrier is a substance having a strong acidity. Therefore, it will be easily understood that the silica-alumina type carrier is likely to by-produce an acetal from an aldehyde and an alcohol, both of which are feedstock materials used in the method of the present invention for producing a carboxylic ester. For this reason, this type of carrier was considered to be inappropriate for use as a carrier in the method of the present invention for producing a carboxylic ester, so that no intensive studies have been made with respect to this type of carrier. However, the present inventors have unexpectedly found that when catalysts containing a carrier selected from the above-mentioned three types of carriers are used, not only can the by-production of acetal be suppressed to an extremely low level, but also a high productivity of the desired carboxylic ester can be achieved. Further, it has been found that a catalyst comprising such a carrier exhibits not only high reactivity, but also excellent mechanical strength and water resistance. In the present invention, it is preferred that the reaction for producing a carboxylic ester using the catalyst of the present invention be conducted while maintaining the pH of the reaction system at 6 to 9. It is considered that under this pH condition, unfavorable phenomena caused by the acidity of the silica-alumina structure can be effectively suppressed.

Hereinbelow, an explanation is made on the above-mentioned three specific types of carriers, i.e., an aluminum-containing silica composition, a silica-alumina-magnesia composition and a crystalline metallosilicate, which can be preferably used in the catalyst of the present invention for improving the life of the catalyst.

With respect to a carrier of an aluminum-containing silica composition comprising silica and alumina, it is preferred that the composition have an aluminum proportion of from 1 to 30 mol. %, based on the total molar amount of silicon and aluminum in the composition. That is, it is preferred that the composition have an Al/(Al+Si) proportion of from 1 to 30 mol. % In the present invention, it is more preferred that the composition have an aluminum proportion of from 5 to 30 mol. %. When the aluminum proportion of the composition is less than 1 mol. %, the composition cannot achieve a satisfactory improvement in mechanical strength and hydrolysis resistance of the carrier. On the other hand, when the aluminum proportion of the composition exceeds 30 mol. %, a marked lowering of acid resistance and mechanical strength of the carrier is observed. The reason for this is considered to reside in that when the aluminum proportion of the composition exceeds 30 mol. %, the excess amount of Al atoms which cannot be incorporated in the silica (Si—O) chain are separated from the composition and deposited on the composition.

With respect to a carrier comprising the silica-alumina-magnesia composition, it is preferred that the composition have silicon, aluminum and magnesium proportions of from 42 to 90 mol. %, from 5.5 to 38 mol. % and from 4 to 38 mol. %, respectively, based on the total molar amount of the silicon, the aluminum and the magnesium. In the present invention, it is more preferred to use, as a carrier, a composition having silicon, aluminum and magnesium proportions of from 75 to 90 mol. %, from 5.5 to 15 mol. % and from 4 to 10 mol. %, respectively, based on the total molar amount of the silicon, the aluminum and the magnesium. When the silicon, aluminum and magnesium proportions are outside the above-mentioned respective ranges, the composition cannot achieve a satisfactory improvement in mechanical strength and hydrolysis resistance of the carrier. The reason for this is considered to reside in that only when the composition has silicon, aluminum and magnesium proportions within the above-mentioned respective ranges, these three components can form a specific structure in which the components are stably bonded together.

With respect to a carrier comprising the crystalline metallosilicate, it is preferred that the crystalline metallosilicate has, in the anhydride state and on a molar basis, a composition represented by formula (1) above. The carrier comprising the crystalline metallosilicate having a composition represented by formula (1) above not only has excellent mechanical strength but also is advantageous from a viewpoint of ease in preparation of a catalyst containing such a carrier.

[I-B] Preparation of a Carrier to be Preferably Used in the Present Invention

Hereinbelow, an explanation is made on a method for preparing the above-mentioned three types of carriers to be preferably used in the present invention. (I-B-1) An explanation is provided on a method for preparing a carrier of a silica-alumina composition as a representative example of an aluminum-containing silica composition. The following five representative modes of the method can be mentioned below.

(1) From commercially available compositions comprising silica and alumina, a composition satisfying the requirements of the composition of the silica-alumina carrier defined in the present invention is chosen;

(2) A silica sol is added to a solution of an aluminum compound, and a reaction is conducted.

(3) A silica sol is reacted with a water-insoluble aluminum compound.

(4) A silica gel is added to an aqueous solution of a water-soluble aluminum compound, and a reaction is conducted.

(5) A silica gel is reacted in the solid phase with an aluminum compound.

Of course, methods for preparing the silica-alumina carrier to be used in the present invention are not restricted to the above-mentioned methods. The resultant aluminum-containing silica composition is calcined under conditions as described below, to thereby obtain a silica-alumina composition to be used as a carrier in the present invention.

Methods (2) to (5) above are explained below in detail. Examples of silica materials include a silica sol, water glass (sodium silicate) and a silica gel. There is no particular limitation with respect to the length of the Si—O chain in the silica gel as long as the silica gel contains non-crosslinked Si atoms. With respect to the above aluminum compound, it is preferred to use a water-soluble compound, such as sodium aluminate, aluminum chloride hexahydrate, aluminum perchlorate hexahydrate, aluminum sulfate, aluminum nitrate nonahydrate, aluminum diacetate and the like. However, a water-insoluble compound, such as aluminum hydroxide or aluminum oxide, may also be used as long as the compound is capable of reacting with a non-crosslinked Si atom which is present in the silica material, such as a silica sol or a silica gel.

In each of methods (2) and (3) above, in which a silica sol is used as a starting material, the silica sol is mixed with an aluminum compound to obtain a mixture sol, and the obtained mixture sol is subjected to a hydrothermal reaction at a temperature of 20 to 100° C. for 1 to 48 hours. The resultant product is dried and then calcined under conditions (temperatures, time and atmosphere) as described below, to thereby obtain a carrier having a silica-alumina composition. Alternatively, an alkaline aqueous solution is added to a mixed sol of a silica sol and an aluminum compound, so that the silica and aluminum compound are coprecipitated, and the precipitate is separated and dried to obtain a gel. Then, the obtained gel is calcined under conditions as described below, to thereby obtain a carrier having a silica-alumina composition. Further, a carrier of a silica-alumina composition having a predetermined particle diameter can be prepared. For example, a particulate composition can be prepared by spray drying the above-mentioned mixed sol, or a granular composition can be obtained by granulating the dried gel obtained from the above-mentioned mixed sol.

In method (3) above, a silica sol is reacted with a water-insoluble aluminum compound. The aluminum compound may be preliminarily pulverized so as to be provided in a particulate form having a predetermined particle diameter, or in a coarsely pulverized form. A silica sol is mixed with the water-insoluble aluminum compound, which has preliminarily been pulverized, and a reaction is conducted at a temperature of 20 to 100° C. for 1 to 48 hours. The resultant product is dried and then calcined under conditions as described below, to thereby obtain a carrier having a silica-alumina composition. Instead of employing the preliminarily pulverized form of aluminum compound, a silica-alumina composition obtained after calcination may be pulverized so as to have a predetermined particle diameter.

In method (4) above, in which a silica gel is used as a starting material, a silica gel is reacted with a water-soluble aluminum compound. The silica gel may be preliminarily pulverized so as to be provided in a particulate form having a predetermined particle diameter, or in a coarsely pulverized form. The preliminarily pulverized silica gel is mixed with the water-soluble aluminum compound, and a reaction is conducted at a temperature of 20 to 100° C. for 1 to 48 hours. The resultant product is dried and then calcined under conditions as described below, to thereby obtain a carrier having a silica-alumina composition. Instead of employing the preliminarily pulverized form of silica gel, a silica-alumina composition obtained after calcination may be pulverized to have a predetermined particle diameter.

In method (5) above, in which a silica gel is used as a starting material as in method (4) above, a silica gel is reacted in the solid phase with an aluminum compound. In this method, Al is caused to react, in the solid phase, with non-crossliked Si atoms in the silica gel. Each of the silica gel and the aluminum compound may be preliminarily pulverized so as to be provided in a particulate form having a predetermined particle diameter, or in a coarsely pulverized form. In this case, these two components may be individually pulverized, or these two components may be mixed together and the resultant mixture may be subjected to pulverization. Instead of employing the preliminary pulverized forms of two components, the silica-alumina composition obtained by reaction and calcination may be pulverized so as to have a predetermined particle diameter.

(I-B-2) Hereinbelow, an explanation is made on a method for preparing a carrier of a silica-alumina-magnesia composition. The following five representative modes of the method can be mentioned below.

(1) A silica-alumina gel is prepared, and then, magnesia is added thereto, to thereby effect a reaction therebetween.

(2) A silica sol is reacted with an aluminum compound and a magnesium compound.

(3) A silica sol is reacted with a water-insoluble aluminum compound and a water-insoluble magnesium compound.

(4) A silica gel is added to an aqueous solution of a water-soluble aluminum compound and a water-soluble magnesium compound, and a reaction is conducted.

(5) A silica gel is reacted in the solid phase with an aluminum compound and a magnesium compound, and the resultant composition containing silica, aluminum, and magnesium is calcined under conditions (temperature, time and atmosphere) as described below, to thereby obtain a silica-alumina-magnesia composition to be used as a carrier in the present invention.

Methods (1) to (5) above are explained below in detail. Examples of silica materials include a silica sol, water glass (sodium silicate) and a silica gel. There is no particular limitation with respect to the length of the Si—O chain in the silica gel as long as the silica gel contains non-crosslinked Si atoms. With respect to the above aluminum compound, it is preferred to use a water-soluble compound, such as sodium aluminate, aluminum chloride hexahydrate, aluminum perchlorate hexahydrate, aluminum sulfate, aluminum nitrate nonahydrate, aluminum diacetate and the like. However, a water-insoluble compound, such as aluminum hydroxide or aluminum oxide, may also be used as long as the compound is capable of reacting with a non-crosslinked Si atom which is present in the silica material, such as a silica sol or a silica gel. Examples of magnesium materials include magnesium oxide, magnesium hydroxide, magnesium acetate, magnesium nitrate, magnesium chloride and magnesium sulfate.

In method (1) above, in which a silica-alumina gel is used as a starting material, sulfuric acid is added to water glass (sodium silicate), to thereby obtain a silica hydrogel having a pH of 8 to 10.5, and a solution of $Al_2(SO_4)_3$ is added to the hydrogel, to thereby obtain a mixture having a pH of 2 or less. Then, sodium aluminate is added to the obtained mixture, to thereby obtain a silica-alumina hydrogel having a pH of 5 to 5.5. The water content of the obtained hydrogel is adjusted to 10 to 40% by, for example, spray drying. After magnesia is added to the hydrogel, the resultant mixture is subjected to hydrothermal reaction at a temperature of 50 to 90° C. for 1 to 5 hours. The resultant product is dried and then calcined under conditions as described below, to thereby obtain a silica-alumina-magnesia composition.

In each of methods (2) and (3) above, in which a silica sol is used as a starting material, the silica sol is mixed with an aluminum compound and a magnesium compound to obtain a mixture sol, and the obtained mixture sol is subjected to a hydrothermal reaction at a temperature of 20 to 100° C. for 1 to 48 hours. The resultant product is dried and then calcined under conditions as described below, to thereby obtain a carrier of a silica-alumina-magnesia composition. Alternatively, an alkaline aqueous solution is added to a mixed sol of a silica sol, an aluminum compound and a magnesium compound, so that the silica, aluminum compound and magnesium compound are coprecipitated, and the precipitate is separated and dried to obtain a gel. Then, the obtained gel is calcined under conditions as described below, to thereby obtain a carrier of a silica-alumina-magnesia composition. Further, a carrier having a silica-alumina-magnesia composition having a predetermined particle diameter can be prepared. For example, a particulate composition can be prepared by spray drying the above-mentioned mixed sol, or a granular composition can be obtained by granulating the dried gel obtained from the above-mentioned mixed sol.

In method (3) above, a silica sol is reacted with a water-insoluble aluminum compound and a water-insoluble magnesium compound. Each of the aluminum compound and the magnesium compound may be preliminarily pulverized so as to be provided in a particulate form having a predetermined particle diameter, or in a coarsely pulverized form. A silica sol is mixed with the water-insoluble aluminum compound and water-insoluble magnesium compound, each of which has preliminarily been pulverized, and a reaction is conducted at a temperature of 20 to 100° C. for 1 to 48 hours. The resultant product is dried and then calcined under conditions as described below, to thereby obtain a carrier of a silica-alumina-magnesia composition. Instead of employing the preliminarily pulverized form of aluminum compound and magnesium compound, a silica-alumina-magnesia composition obtained after calcination may be pulverized so as to have a predetermined particle diameter.

In method (4) above, in which a silica gel is used as a starting material, a silica gel is reacted with a water-soluble aluminum compound and a water-soluble magnesium compound. The silica gel may be preliminarily pulverized so as to be provided in a particulate form having a predetermined particle diameter, or in a coarsely pulverized form. The preliminarily pulverized silica gel is mixed with the water-soluble aluminum compound and water-soluble magnesium compound, and a reaction is conducted at a temperature of 20 to 100° C. for 1 to 48 hours. The resultant product is dried and then calcined under conditions as described below, to thereby obtain a carrier having a silica-alumina-magnesia composition. Instead of employing the preliminarily pulverized form of silica gel, a silica-alumina-magnesia composition obtained after calcination may be pulverized to have a predetermined particle diameter.

In method (5) above, in which a silica gel is used as a starting material as in method (4) above, a silica gel is reacted in the solid phase with an aluminum compound and a magnesium compound. In this method, Al and Mg are caused to react, in the solid phase, with non-crosslinked Si atoms in the silica gel. Each of the silica gel, the aluminum compound and the magnesium compound may be preliminarily pulverized so as to be provided in a particulate form having a predetermined particle diameter, or in a coarsely pulverized form. In this case, these three components may be individually pulverized, or these three components may be mixed together and the resultant mixture may be subjected to pulverization. Instead of employing the preliminarily pulverized forms of the three components, the silica-alumina-magnesia composition obtained by reaction and calcination may be pulverized so as to have a predetermined particle diameter. (I-B-3) An explanation will now be made on the carrier comprising the crystalline metallosilicate of formula (1).

In formula (1), M represents a cation having a valence of 1 or 2. The cation is selected from a proton and cations of metals belonging to Groups IB, IIA, IIB, IIIA, IIIB, IVA, IVB, VB, VIB, VIIB and VIII of the short-form Periodic Table.

R in formula (1) represents at least one metal having a valence of 1 to 4, which is selected from metals belonging to Groups IB, IIB, IIIA, IIIB, IVA, IVB, VA, VB, VIB, VIIB and VIII of the short-form Periodic Table. Examples of such metals usable as R include aluminum, boron, gallium, titanium, chromium and iron.

It is preferred that the crystalline metallosilicate be a crystalline aluminometallosilicate in which aluminum is incorporated as at least one metal represented by R. It is more preferred that the crystalline metallosilicate be a crystalline aluminosilicate.

The silica/$R_{2/w}O$ molar ratio of the crystalline metallosilicate is represented by y in formula (1), and y is in the range of from 0.5 to 500, preferably from 0.5 to 200, more preferably from 0.5 to 100. When the silica/$R_{2/w}O$ molar ratio is outside the above-mentioned range, the effects of improving mechanical properties and water resistance are small. The reason for this is presumed to reside in that a stable crystalline metallosilicate structure is formed only when the silica/$R_{2/w}O$ molar ratio is within the above-mentioned range.

X in formula (1) represents the amount of cation necessary for neutralizing a negative charge which is generated by the bonding between silica and $R_{2/w}O$, wherein the amount of cation is expressed in terms of the molar ratio of $M_{2/n}O$ to $R_{2/w}O$, and X in formula (1) is in the range of 0.3±0.1, independently of the value of y.

There are a wide variety of types of crystalline metallosilicates. Specific examples of structurally different crystalline metallosilicates include zeolites of the nalcime family, the faujasite family, the chabazite family, the natrolite family, the phillipsite family, the mordenite family, the ZSM-5 family, the ZSM-5-like family and the ZSM-11 family.

Examples of zeolites of the ZSM-5-like family include ZSM-8 (see German Patent No. 2,049,755), ZETA-1 (see German Patent No. 2,548,697), ZETA-3 (see British Patent No. 1,553,209), UN-4 (see German Patent No. 3,268,503), UN-5 (see German Patent No. 3,169,606), TZ-01 (see U.S. Pat. No. 4,581,216), crystalline aluminosilicate (see U.S. Pat. No. 4,954,326), TRS (see German Patent No. 1,924,870), MB-28 (see European Patent No. 21,445), TSZ {see Unexamined Japanese Patent Application Laid-Open Specification (Japanese Kokai) No. 58-45111} and AZ-1 (see European Patent No. 113,116).

The crystalline metallosilicate to be used in the present invention can be synthesized by a hydrothermal reaction wherein the reaction is conducted usually at 20 to 100° C. for 1 to 48 hours.

With respect to the source of silica, there is no particular limitation. Water glass, a silica sol, a silica gel or the like can be used as the source of silica.

As the source of metals, inorganic metal compounds and organometal compounds can be used. Examples of inorganic metal compounds include metal salts, such as a metal sulfate, a metal nitrate and the like, metal halides, such as a metal chloride, a metal bromide and the like, and a metal oxide and the like.

If desired, the synthesis of the crystalline metallosilicate to be used in the present invention may be conducted in the presence of an organic template. Preferred examples of organic templates include a urea compound, such as dimethyl urea or the like, a quaternary ammonium salt, such as tetrapropyl ammonium salt or the like, a diamine, such as hexamethylene diamine, and an alcohol.

When an organic template is employed for the synthesis of a microcrystalline metallosilicate, it is necessary that, after the hydrothermal reaction, organic matters be removed from the crystals of the synthesized crystalline metallosilicate. Examples of methods for removing organic matters include a method in which a calcination is conducted at 400 to 800° C. for 1 to 48 hours in air, and a liquid phase oxidation method using an oxidizing agent, such as hydrogen peroxide. (I-B-4) The specific surface area of each of the above-mentioned compositions, which are preferably employable as a carrier for the catalyst of the present invention, is generally from 10 to 700 m$^2$/g, preferably from 20 to 350 m$^2$/g, more preferably from 50 to 300 m$^2$/g, as measured by the BET nitrogen adsorption method. When the specific surface area is less than 10 m$^2$/g, there are disadvantages such that it is difficult to support a palladium component on the carrier, that a palladium component, even if supported on the carrier, is likely to come-off from the carrier, and that the catalyst activity is low. A large specific surface area of the carrier does not pose a particular problem on the activity of the catalyst. However, when the specific surface area of the carrier is large, the mechanical strength and water resistance of the catalyst tend to be low. Therefore, it is most preferred that the specific surface area be selected from the range of from 50 to 200 m$^2$/g.

The above-mentioned various compositions, which are preferably employable as a carrier for the catalyst of the present invention, are calcined at an appropriate temperature so as to provide a desired specific surface area within the range mentioned above. Generally, the calcination temperature is selected from the range of from 200 to 800° C. When the calcination temperature is more than 800° C., a marked lowering in specific surface area of the carrier disadvantageously occurs. With respect to the atmosphere to be used for the calcination, there is no particular limitation. However, the calcination is generally conducted in air or nitrogen gas. The calcination time is chosen, taking into consideration the desired specific surface area. However, the calcination is generally conducted for 1 to 48 hours.

II. Production of Catalyst

With respect to the production of the catalyst of the present invention, a detailed explanation is given below.

[II-A] Production of the Catalyst of the Present Invention from a Catalyst Precursor Hereinbelow, an explanation is made on a method for producing the catalyst of the present invention, which comprises subjecting a catalyst precursor comprising a carrier having supported thereon a reducible palladium compound or a mixture of a reducible palladium compound and a reducible lead compound to a reduction treatment with a reducing agent in a solvent in the presence of lead ions and at least one compound selected from the group consisting of a $C_1$–$C_5$ fatty acid, an alkali metal salt and an alkaline earth metal salt.

The catalyst precursor comprising a carrier having supported thereon a reducible palladium compound (which is hereinafter, frequently referred to simply as "palladium compound") can be prepared by a conventional method. In a representative method for preparing the catalyst precursor, a carrier is added to an aqueous solution of a soluble palladium salt, such as palladium chloride and, the resultant mixture is heated at 20 to 100° C. for 1 to 24 hours so that the carrier is well impregnated with the aqueous palladium salt solution. Thus, a catalyst precursor comprising the carrier having a palladium salt supported thereon can be obtained.

With respect to a catalyst precursor comprising a carrier having a mixture of a reducible palladium compound and a reducible lead compound, the preparation of the catalyst precursor can be conducted in the same manner as mentioned above. That is, a carrier is well impregnated with an aqueous solution of a soluble palladium compound, such as palladium chloride, and a soluble lead compound, such as lead acetate by heating a mixture of the carrier and the aqueous solution at 20 to 100° C. for 1 to 24 hours. The palladium compound and lead compound can be applied to the carrier simultaneously, or either of the palladium compound and lead compound is first applied to the carrier and then, the remaining one can be applied to the carrier.

The metallic species of the catalyst precursor may contain, in addition to the essential palladium or the essential mixture of palladium and lead, other metallic elements, for example, mercury, thallium, bismuth, tellurium, nickel, chromium, cobalt, indium, tantalum, copper, zinc, zirconium, hafnium, tungsten, manganese, silver, rhenium, antimony, tin, rhodium, ruthenium, iridium, platinum, gold, titanium, aluminum, boron and silicon. Compounds of the above metallic elements other than palladium and lead can be employed in an amount of 5% by weight or less, preferably not more than 1% by weight (in terms of metal), based on the weight of the final catalyst containing all metallic species in reduced form.

Further, at least one metallic species selected from alkali metals and alkaline earth metals can be incorporated in the catalyst precursor. Such an incorporation of at least one compound selected from an alkali metal salt and an alkaline earth metal salt in the catalyst precursor is preferred because the catalyst containing such a compound exhibits high reactivity. The alkali metal salt and/or alkaline earth metal salt can be employed in an amount of 0.01 to 30% by weight, preferably 0.01 to 5% by weight (in terms of metal), based on the weight of the final catalyst containing all metallic species in reduced form. A small amount of at least one of the above metallic species (including alkali metals and alkaline earth metals) other than palladium and lead may be intruded between the crystal lattices and/or may be substituted for the palladium and/or lead in the crystal lattice. In practice, at least one of the salts of these metallic species (including alkali metals and alkaline earth metals) other than Pd and Pb can be added to the aqueous solution of a Pd compound or a mixture of a Pd compound and a Pb compound so as to be adsorbed on or attached to the carrier, or can be originally supported on a carrier. Alternatively, at least one of these other metallic species can be added to a reduction reaction system used for producing a final catalyst by reducing the catalyst precursor.

The palladium compounds and lead compounds to be used for preparing catalyst precursors include palladium salts and lead salts of, for example, organic acids, such as formic acid and acetic acid; and inorganic acids, such as sulfuric acid, hydrochloric acid and nitric acid, and also include, for example, organic complexes of palladium and lead, such as ammine complexes and benzonitrile complexes; oxides of palladium and lead; and hydroxides of palladium. Preferred examples of palladium compounds include palladium chloride and palladium acetate, and preferred examples of lead compounds include lead nitrate and lead acetate. Preferred examples of alkali metal compounds and alkaline earth metal compounds include organic acid salts, inorganic acid salts and hydroxides of alkali metals and alkaline earth metals, and, among them, $C_1$–$C_5$ fatty acid salts are most preferred.

Examples of carriers include silica, alumina, silica-alumina, zeolite, magnesia, magnesium hydroxide, titania, calcium carbonate, activated carbon and the like. However, the above-mentioned three specific types of carriers are most preferred.

In the catalyst of the present invention, the amount of palladium supported on the carrier is not specifically limited, however, is generally in an amount of from 0.1 to 20% by weight, preferably from 1 to 10% by weight, based on the weight of the carrier. The amount of lead supported on the carrier is also not specifically limited, however, is generally in an amount of from 0.1 to 20% by weight, preferably from 1 to 10% by weight, based on the weight of the carrier. In this connection, it should be noted that the Pd/Pb atomic ratio is important rather than the respective amounts of palladium and lead supported on the carrier. The ratio of the palladium compound to the lead compound is selected within the range of from 3/0 to 3/1.3, preferably from 3/0 to 3/0.7 in terms of the Pd/Pb atomic ratio.

Thus, the catalyst of the present invention can be produced by subjecting the above-mentioned catalyst precursor to a reduction treatment with a reducing agent in a solvent in the presence of lead ions in an amount necessary for obtaining a final catalyst comprising a carrier having supported thereon palladium and lead in an atomic ratio (S) of $3/0.7 \leq S \leq 3/1.3$, wherein the solvent is at least one member selected from the group consisting of water and an alcohol, such as methanol, and the reducing agent is at least one member selected from the group consisting of formaldehyde, formic acid, hydrazine, methanol and molecular hydrogen.

An illustrative explanation is made below on the production of the catalyst of the present invention from the catalyst precursor comprising a carrier having supported thereon a palladium compound or a mixture of a palladium compound and a lead compound.

As mentioned above, the catalyst precursor is dispersed in a solvent selected from the group consisting of water and an alcohol (such as methanol), and subjected to a reduction treatment with a reducing agent, under heating at 20 to 200° C., preferably 40 to 160° C., in the presence of lead values in an amount necessary for obtaining a catalyst of the present invention.

Solvents other than water and an alcohol (such as methanol) can also be used as a solvent for the reduction treatment as long as the solvents used are inert to the reduction system under the reduction treatment conditions. However, the use of water or methanol is preferred from a practical point of view.

As the reducing agent, there can be mentioned formaldehyde, formic acid, hydrazine, methanol, molecular hydrogen and a mixture thereof. In the case of the reduction treatment using formaldehyde, formic acid, hydrazine or a mixture thereof, it can be used in such a manner that it is simply added, in the form of a solution thereof in water and/or methanol, to the catalyst precursor dispersion. In the case of the reduction treatment using methanol, the reduction treatment becomes more simple. That is, the reduction treatment can be effected by only dispersing the catalyst intermediate in methanol. In the case of the reduction treatment using molecular hydrogen, pure hydrogen gas, or a gaseous mixture of hydrogen gas and an inert gas (such as nitrogen gas or methane gas) in which the hydrogen concentration of the gaseous mixture is 0.1% or more by volume, is blown into the catalyst precursor dispersion under from 1 to several tens atm, preferably from 1 to several atm. Formaldehyde, formic acid, hydrazine, methanol or molecular hydrogen is used in a molar amount of from 0.1 to 100 times, preferably from 0.5 to 10 times as large as the molar amount of the palladium compound contained in the catalyst precursor. The use of a reducing agent in excess of the above range poses no problems. Addition of an alkali (such as sodium hydroxide) to the reduction system is preferred because the reduction reaction can easily proceed.

The alkali is usually used in a 1/100 to equimolar amount relative to the molar amount of the reducing agent.

In the reduction treatment, it is requisite that lead ions be present in the reduction system. For this purpose a lead-containing substance is usually added to a dispersion of the catalyst precursor in water, methanol or a mixture thereof. The type of the lead-containing substance is not specifically limited as long as it can be dissolved in the dispersion in the form of lead ions. Examples of lead-containing substances include lead salts of organic acids, such as formic acid and acetic acid; and lead salts of inorganic acids, such as sulfuric acid, hydrochloric acid and nitric acid, and also include lead oxide; and lead hydroxide. Among them, lead nitrate and lead acetate are preferred because these lead salts have high solubility. In this connection, it should be noted that it is not always necessary to add a lead-containing substance from the outside of the reduction system, but lead ions dissolved-out from the catalyst precursor are sometimes sufficient for the purpose.

The amount of a lead-containing substance to be added may be varied depending on the type of the catalyst precursor used. However, it is essential that a lead-containing substance be added to the reduction system in an amount necessary for obtaining a final catalyst of the present invention comprising a carrier having supported thereon palladium and lead in a Pd/Pb atomic ratio (S) of $3/0.7 \leq S \leq 3/1.3$. That is, in order that the catalyst having such a Pd/Pb atomic ratio can be obtained, an appropriate amount of the lead-containing substance is chosen from the range of from 3/0 to 3/1.3 in terms of the Pd/Pb atomic ratio of the Pd contained in the palladium compound of the catalyst precursor to the Pb contained in the lead-containing substance, and the lead-containing substance is added to the catalyst precursor dispersion in an amount satisfying the above-mentioned Pd/Pb atomic ratio, followed by reduction treatment.

The lead-containing substance can be continuously or intermittently added prior to or during the reduction treatment.

In the reduction treatment of the catalyst precursor, even when the catalyst precursor already has a Pd/Pb atomic ratio (S) in the range of $3/0.7 \leq S \leq 3/1.3$, it may be subjected to a reduction treatment while adding a lead-containing substance to the reduction reaction system, as long as the final catalyst has a Pd/Pb atomic ratio not exceeding 3/1.3. Alternatively, the reduction treatment may be conducted without adding any lead-containing substance (in this case, Pb ions dissolved out from the catalyst precursor serve as Pb ions necessary in the reduction process).

As mentioned above, the catalyst of the present invention can be obtained by subjecting the catalyst precursor to a reduction treatment in the presence of Pb ions and at least one compound selected from the group consisting of a lower ($C_1$–$C_5$) fatty acid, an alkali metal salt and an alkaline metal salt.

Examples of lower ($C_1$–$C_5$) fatty acids include propionic acid, acetic acid and maleic acid. A most preferred lower fatty acid is acetic acid from a practical viewpoint. The lower fatty acid can be used in a molar amount of from 0.1 to 30 times, preferably from 1 to 15 times as large as the molar amount of palladium salt (in terms of Pd) contained in the catalyst precursor. The lower fatty acid can be added simultaneously with or prior to the addition of the reducing agent, wherein the latter is preferred from a viewpoint of effects achieved. The addition of a lower fatty acid is effective especially when the catalyst precursor contains both a palladium compound and a lead compound.

In the reduction treatment, it is preferred to use an alkali metal salt and/or an alkaline earth metal salt, each of a lower ($C_1$–$C_5$) fatty acid. The present inventors have found that the use of such an alkali metal salt and/or an alkaline earth metal salt in the reduction treatment is very effective for obtaining a catalyst of the present invention which comprises a carrier having supported thereon palladium and lead in the form of a high quality $Pd_3Pb_1$ intermetallic compound having no or only few lattice defects. This effect can be achieved with respect to not only a catalyst containing only a palladium compound but also a catalyst precursor containing both a palladium compound and a lead compound. The alkali metal salt and/or alkaline earth metal salt, each of a lower fatty acid, can be used in a molar amount of from 0.1 to 30 times, preferably from 1 to 15 times as large as the molar amount of the palladium compound (in terms of Pd). Preferred examples of alkali metal salts and alkaline earth metal salts include sodium acetate and magnesium acetate. The reason why the reduction treatment conducted in the presence of lead ions and at least one compound selected from a lower fatty acid, an alkali metal salt and an alkaline earth metal salt gives a high quality $Pd_3Pd_1$ intermetallic compound having no or only few lattice defects has not yet been elucidated, however, it is believed that, by virtue of the presence of protons, alkali metal cations and/or alkaline earth metal cations, the lead ions are caused to easily, selectively interact with the defective portions of the crystal lattice of the Pd—Pb intermetallic compound, thereby facilitating the lead ions to be introduced into the crystal lattice.

The reduction treatment of the catalyst precursor can be conducted at room temperature to 200° C. under a pressure necessary for maintaining the reduction treatment system in a liquid state, preferably at 40 to 160° C. under atmospheric pressure to several atm. The reduction treatment time varies depending on the type of the catalyst active species and the reduction treatment conditions, but is generally in the range of from several minutes to 100 hours. It is preferred to choose the reduction treatment conditions so that the reduction can be completed within several hours. Completion of the reduction can be easily confirmed by measuring the diffraction angle ($\theta$) for a maximum intensity peak ascribed to the (111) crystal face diffraction with respect to the powder X-ray diffraction pattern of the catalyst obtained by the reduction treatment.

The type of the reactor used in the reduction treatment is not specifically limited, and a conventional agitation vessel type reactor can generally be used.

By subjecting the catalyst precursor to a reduction treatment in such a manner as mentioned above, a high quality, high purity catalyst having no or only few lattice defects can be obtained, wherein the catalyst comprises a carrier having supported thereon palladium and lead in a Pd/Pb atomic ratio (S) of $3/0.7 \leq S \leq 3/1.3$, and wherein the catalyst exhibits a maximum intensity peak at a diffraction angle ($2\theta$) in the range of from 38.55° to 38.70° in a powder X-ray diffraction pattern thereof, wherein the peak is ascribed to the (111) crystal face diffraction of a Pd—Pb intermetallic compound. In a more preferred aspect of the present invention, the catalyst exhibits, in a spectrum obtained from the catalyst by X-ray photoelectron spectroscopy, a ratio of from 1/0.2 to 1/0.7 in terms of the $\{Pd3d(3/2)+Pd3d(5/2)\}/\{Pb4f(7/2)\times1.75\}$ ratio of the sum of respective intensities of two peaks respectively ascribed to the 3d(3/2) electron and the 3d(5/2) electron of metallic palladium to the intensity of a peak ascribed to the 4f(7/2) electron of metallic lead which is multiplied by 1.75.

When the diffraction angle ($2\theta$) for a maximum intensity peak ascribed to the (111) crystal face diffraction of a Pd—Pb intermetallic compound in the powder X-ray diffraction pattern of the catalyst is less than 38.55°, the yield of a desired carboxylic ester, based on the alcohol used, is extremely lowered, leading to an increase in unfavorable by-production of, for example, methyl formate. When the diffraction angle ($2\theta$) is larger than 38.70°, an aldehyde decomposition reaction is likely to occur markedly, so that the yield of a desired carboxylic ester, based on the aldehyde, is lowered. On the other hand, when the amount of lead in the catalyst is larger than the amount corresponding to the Pd/Pb ratio of 3/1.3, a reaction of by-producing, for example, methyl formate, is likely to occur markedly. Whereas, when the amount of lead in the catalyst is smaller than the amount corresponding to the Pd/Pb atomic ratio of 3/0.7, the selectivity for a desired carboxylic ester, for example, MMA, is markedly lowered. In contrast, by the use of the catalyst of the present invention, the yield of a desired carboxylic ester is improved not only on an aldehyde basis but also on an alcohol basis.

By the above-mentioned preparation method of the present invention, it has become possible to obtain a catalyst having a Pd/Pb atomic ratio of from 3/0.7 to 3/1.3, namely, close to 3/1, containing no or only very little excess lead as lead impurities, and having no or only few lattice defects. It may seem to be possible to obtain a catalyst having a Pd/Pb atomic ratio close to 3/1. However, when a catalyst having a Pd/Pb atomic ratio close to 3/1, which is produced by the conventional preparation method, is used, it results in a poor selectivity for a desired carboxylic ester. The above-mentioned preparation method of the present invention has rendered it possible to obtain a high quality, high purity catalyst having not only a Pd/Pb atomic ratio close to 3/1 but also having no or only few lattice defects. Thus, not only can an improved selectivity for a desired carboxylic ester, such as MMA, be achieved, whereby the formation of a by-product derived from the alcohol, for example, methyl formate, is greatly suppressed, but also the smaller content of lead impurities in the catalyst contributes to a decrease in dissolution-out of lead values into the waste water from the process for the production of carboxylic esters, thereby enabling the treatment cost for detoxifying the lead values contained in the waste water to be obviated. Therefore, various significant practical advantages can be brought about by the present invention.

As mentioned above, the catalyst preparation method of the present invention is simple, wherein the catalyst precursor comprising a carrier having supported thereon a palladium compound or a mixture of a palladium compound and a lead compound is subjected to a reduction treatment with a reducing agent in a solvent in the presence of lead ions and at least one compound selected from the group consisting of a $C_1$–$C_5$ fatty acid, an alkali metal salt and an alkaline earth metal salt. The reasons why a catalyst containing, with high purity, a high quality $Pd_3Pb_1$ intermetallic compound having no or only few lattice defects can be obtained by the method of the present invention have not yet been elucidated. However, it is presumed that, in one aspect, activated hydrogen, which is formed on a catalyst under the above-mentioned reduction conditions, plays an important role in the formation of a defect-free lattice of a high quality, high purity Pd—Pb intermetallic compound, that is, such activated hydrogen and the lead ions together serve to facilitate change of the lattice structure of a once formed Pd—Pb intermetallic compound to a defect-free lattice structure, and that, in another aspect, the alkali metal cations and/or the alkaline earth metal cations play an important role in facilitating the lead ions to selectively interact with defective portions of the lattice of the Pd—Pb intermetallic compound.

The palladium-lead catalyst obtained by the above-mentioned preparation process of the present invention can be advantageously used in a process for producing a carboxylic ester from an aldehyde, an alcohol and molecular oxygen. The amount of catalyst is not specifically limited, but largely varies depending on the types of raw materials, the composition and preparation method of the catalyst, the reaction conditions, the reaction modes and the like. For example, when the catalyst is used in a slurry form, it is preferred to use the catalyst in an amount of from 0.04 to 0.5 kg per liter of a reaction system comprising the aldehyde, the alcohol and molecular oxygen.

[II-B] Production of the Catalyst of the Present Invention by Activation of a Catalyst Intermediate (II-B-1) Preparation of a Catalyst Intermediate Hereinbelow, an explanation is made on another method for obtaining a catalyst of the present invention. This method comprises activating catalyst compositions, each comprising a carrier having supported thereon palladium or a mixture of palladium and lead, wherein the catalyst compositions have various Pd/Pb atomic ratios and do not satisfy all or part of the requirements of the high quality, high purity catalyst of the present invention (each of such catalyst compositions is, hereinafter, frequently referred to as a "catalyst intermediate").

In the present invention, as already mentioned above, the term "activation" means various processes for modifying or altering the above-mentioned catalyst intermediate, so as to obtain a catalyst satisfying all of the requirements of the catalyst of the present invention.

Examples of catalyst intermediates include a conventional catalyst prepared by a known method, and a spent catalyst which originally satisfied the essential requirements of the catalyst of the present invention, but has become deteriorated as a result of use in the reaction of producing a desired carboxylic ester, so that it no longer satisfies a part or all of the requirements of the catalyst of the present invention.

In a representative method for preparing a catalyst intermediate, a carrier is added to an aqueous solution of a soluble palladium compound, such as palladium chloride, or an aqueous solution of a mixture of a soluble palladium compound, such as palladium chloride, and a soluble lead compound, such as lead acetate; the resultant mixture is heated at 20 to 100° C. for 1 to 24 hours so that the carrier is well impregnated with the aqueous solution of the palladium compound or the aqueous solution of the mixture of the palladium compound and the lead compound; and the reduction of the Pd or the mixture of the Pd and the Pb supported on the carrier is conducted using formaldehyde, formic acid, hydrazine, methanol, hydrogen gas or the like. For preparing a catalyst intermediate comprising a carrier having supported thereon a mixture of palladium and lead, the palladium compound and lead compound can be applied to the carrier simultaneously, or either of the palladium compound and lead compound is first applied to the carrier and then, the remaining one can be applied to the carrier. Alternatively, a carrier having a palladium compound supported thereon may be subjected to reduction in the presence of the lead compound.

The metallic species of the catalyst intermediate may contain, in addition to the essential palladium or the essential mixture of palladium and lead, other metallic elements, for example, mercury, thallium, bismuth, tellurium, nickel, chromium, cobalt, indium, tantalum, copper, zinc, zirconium, hafnium, tungsten, manganese, silver, rhenium, antimony, tin, rhodium, ruthenium, iridium, platinum, gold, titanium, aluminum, boron and silicon. Compounds of the above metallic elements other than a palladium salt and a lead salt can be employed in an amount of 5% by weight or less, preferably not more than 1% by weight (in terms of metal), based on the weight of all of the metallic species in reduced form.

Further, at least one metallic species selected from alkali metals and alkaline earth metals can be incorporated in the catalyst intermediate by the use of at least one compound selected from an alkali metal salt and an alkaline earth metal salt. Such an incorporation of at least one metallic species selected from alkali metals and alkaline earth metals is preferred because the catalyst having such a metallic species supported on the carrier exhibits high reactivity. The alkali metal salt and/or alkaline earth metal salt can be employed in an amount of 0.01 to 30% by weight, preferably 0.01 to 5% by weight (in terms of metal), based on the weight of all metallic species in reduced form. A small amount of at least one of the above metallic species (including alkali metals and alkaline earth metals) other than palladium and lead may be intruded between the crystal lattices and/or may be substituted for the palladium and/or lead in the crystal lattice. In practice, at least one of salts of these metallic species (including alkali metals and alkaline earth metals) other than Pd and Pb can be added to the aqueous solution of Pd or a mixture of Pd and Pb so as to be adsorbed on or attached to the carrier, or can be originally supported on a carrier. Alternatively, at least one of these other metallic species can be added to a reduction reaction system used for preparing a catalyst intermediate.

The palladium compounds and lead compounds to be used for preparing catalyst intermediates include palladium salts and lead salts of, for example, organic acids, such as formic acid and acetic acid; and inorganic acids, such as sulfuric acid, hydrochloric acid and nitric acid, and also include, for example, organic complexes of palladium and lead, such as ammine complexes and benzonitrile complexes; oxides of palladium and lead; and hydroxides of palladium and lead. Preferred examples of palladium compounds include palladium chloride and palladium acetate, and preferred examples of lead compounds include lead nitrate and lead acetate. Preferred examples of alkali metal compounds and alkaline earth metal compounds include organic acid salts, inorganic acid salts and hydroxides of alkali metals and alkaline earth metals.

Examples of carriers include silica, alumina, silica-alumina, crystalline metallosilicate, silica-alumina-magnesia, magnesium hydroxide, titania, calcium carbonate, activated carbon and the like. From a viewpoint of mechanical strength, silica-alumina, silica-alumina-magnesia and crystalline metallosilicate are preferred. Further, the above-mentioned specific types of silica-alumina, silica-alumina-magnesia and crystalline metallosilicate are most preferred.

In the catalyst of the present invention, the amount of palladium supported on the carrier is not specifically limited, however, is generally in an amount of from 0.1 to 20% by weight, preferably from 1 to 10% by weight, based on the weight of the carrier. The amount of lead supported on the carrier is also not specifically limited, however, is generally in an amount of from 0 to 20% by weight, preferably from 1 to 10% by weight, based on the weight of the carrier. In this connection, it should be noted that the Pd/Pb atomic ratio is important rather than the respective amounts of palladium and lead supported on the carrier. The catalyst intermediate used in the present invention has a Pd/Pb atomic ratio (S) of $3/0 \leq S \leq 3/1.3$, preferably $3/0.1 \leq S \leq 3/3$. However, the preferred range of the Pd/Pb atomic ratio (S) of the catalyst intermediate varies depending on which activation method is selected from the first to fourth activation methods described below.

(II-B-2) Activation of a Catalyst Intermediate

A detailed explanation is given below with respect to a method for producing the catalyst of the present invention by activating a catalyst intermediate comprising a carrier having supported thereon palladium, or a mixture of palladium and lead.

As already mentioned above, the term "activation" used herein means a process for obtaining the catalyst of the present invention from a catalyst intermediate comprising a carrier having supported thereon palladium or a mixture of palladium and lead. In the present invention, the following four methods (namely, first to fourth methods) are disclosed for effecting such an activation.

(II-B-2-i) The first activation method comprises reducing the above-mentioned catalyst intermediate in the presence of lead ions in a solvent selected from water, an alcohol (such as methanol) and a mixture thereof, under heating at 20 to 100° C. Other solvents than water and an alcohol (such as methanol) can also be used as a solvent for the activation treatment as long as the solvents used are inert to the activation reaction system under the activation treatment conditions. However, the use of water is preferred from a practical point of view.

As the reducing agent which serves as an activating agent for the catalyst intermediate, there can be mentioned formaldehyde, formic acid, hydrazine, methanol, molecular hydrogen and a mixture thereof. In the case of the activation treatment using formaldehyde, formic acid, hydrazine or a mixture thereof, it can be used in such a manner that it is simply added, in the form of a solution thereof in water and/or methanol, to a dispersion of the catalyst intermediate. In the case of the activation treatment using methanol, the activation process is more simple. That is, the activation can be performed by only dispersing the catalyst intermediate in methanol. In the case of the activation treatment using molecular hydrogen, pure hydrogen gas, or a gaseous mixture of hydrogen gas and an inert gas (such as nitrogen gas or methane gas), wherein the hydrogen concentration of the gaseous mixture is 0.1% or more by volume, is blown into the catalyst intermediate dispersion under 1 to several tens atm, preferably from 1 to several atm. Formaldehyde, formic acid, hydrazine, methanol or molecular hydrogen can be used in a molar amount of from 0.1 to 100 times, preferably from 0.5 to 10 times as large as the molar amount of the palladium contained in the catalyst intermediate. The use of an activating agent in excess of the above range poses no problems. Addition of an alkali (such as sodium hydroxide) to the activation reaction system is preferred because the activation can easily proceed. The alkali is usually used in a $1/100$ to equimolar amount relative to the molar amount of the activating agent.

In the first method of activation treatment, it is requisite that lead ions are present in the reaction system for the activation. For this purpose, a lead-containing substance is usually added to a dispersion of the catalyst intermediate in water, methanol or a mixture thereof. The type of the lead-containing substance is not specifically limited as long as it can be dissolved in the dispersion in the form of lead ions. Examples of lead-containing substances include lead salts of organic acids, such as formic acid and acetic acid; and lead salts of inorganic acids, such as sulfuric acid, hydrochloric acid and nitric acid, and also include lead oxide; and lead hydroxide. Among them, lead nitrate and lead acetate are preferred because these lead salts have high solubility. Generally, a lead-containing substance is added to a dispersion of the catalyst intermediate in a solvent selected from water, methanol and a mixture thereof, and the activation operation is conducted.

The amount of a lead-containing substance to be added may be varied depending on the type of the catalyst intermediate used. Generally, an appropriate amount of lead-containing substance is chosen within the range of from 3/0.01 to 3/2 in terms of the atomic ratio of the Pd contained in the catalyst intermediate to the Pb contained in the lead-containing substance, and the catalyst intermediate is dispersed in a solution of the lead-containing substance in water and/or methanol, and the activation operation is conducted.

In the above-mentioned activation method, it is preferred that the catalyst intermediate used have a Pd/Pb atomic ratio (S) of $3/0 \leq S \leq 3/1.3$.

In the above-mentioned activation method, for obtaining a catalyst comprising a carrier having supported thereon palladium and lead in a Pd/Pb atomic ratio of 3/0.7 to 3/1.3, preferably in a Pd/Pb atomic ratio as close to 3/1 as possible, it is preferred that the amount of lead-containing substance added to the activation reaction system be in the range of from 3/0.03 to 3/0.6 in terms of the Pd/Pb atomic ratio of the Pd contained in the catalyst intermediate to the Pb contained in the lead-containing substance. The lead-containing substance can be continuously or intermittently added prior to or during the activation treatment.

As mentioned above, for providing lead ions in the activation reaction system, a lead-containing substance is generally used. However, when the catalyst intermediate to be subjected to activation is of low purity, such a catalyst intermediate has a large amount of lead impurities. These lead impurities can be utilized as a source of lead ions, that is, the lead component contained in the catalyst intermediate as impurities is dissolved out in an ionized form thereof into the reaction system, thus providing lead ions in the reaction system even without addition of a lead-containing substance from the outside. In this case, for facilitating the lead component to be dissolved out into the reaction system, it is preferred that a lower ($C_1$–$C_5$) fatty acid, such as propionic acid, acetic acid, butyric acid or maleic acid, be added to the activation reaction system. When the amount of lower fatty acid added to the reaction system is too large, the amount of lead dissolved out into the reaction system becomes too large, so that the final catalyst is likely to be deteriorated. Therefore, the lower fatty acid can be used in a molar amount of from 0.1 to 30 times, preferably from 1 to 15 times as large as the molar amount of the palladium contained in the catalyst intermediate. From a practical point of view, it is preferred to use acetic acid which is easily available.

The above-mentioned fatty acid may be added to the solvent simultaneously with the addition of a reducing agent which serves as an activating agent. However, when the fatty acid is added to the solvent prior to the addition of the reducing agent, the necessary amount of lead ions can be dissolved out into the reaction system more efficiently. Further, even when a lead-containing substance is used, it is preferred to use a fatty acid, because the necessary amount of the lead-containing substance to be added to the reaction system can be decreased.

In the above-mentioned first activation method, it is preferred to use an alkali metal salt and/or an alkaline earth metal salt, each of a lower ($C_1$–$C_5$) fatty acid. The present inventors have found that the use of such an alkali metal salt and/or an alkaline earth metal salt in the activation treatment is very effective for obtaining a catalyst of the present invention which comprises a carrier having supported thereon palladium and lead in the form of a high quality $Pb_3Pb_1$ intermetallic compound having no or only few lattice defects. The alkali metal salt and/or alkaline earth metal salt, each of a lower fatty acid, can be used in a molar amount of from 0.1 to 30 times, preferably from 1 to 15 times as large as the molar amount of the palladium contained in the catalyst intermediate. Preferred examples of alkali metal salts and alkaline earth metal salts include sodium acetate and magnesium acetate. The reason why the activation treatment conducted in the presence of lead ions and at least one compound selected from an alkali metal salt and an alkaline earth metal salt gives a high quality $Pd_3Pd_1$ intermetallic compound having no or only few lattice defects has not yet been elucidated, however, it is believed that, by virtue of the presence of alkali metal cations and/or alkaline earth metal cations, the lead ions are caused to easily, selectively interact with defective portions of the crystal lattice of the Pd—Pb intermetallic compound, thereby facilitating the lead ions to be introduced into the crystal lattice.

The alkali metal salts and/or the alkaline earth metal salts can be used instead of the above-mentioned lower fatty acid, so as to achieve the effect of dissolving out the lead impurities from the catalyst intermediate.

When the activation treatment of the catalyst intermediate is conducted using the above-mentioned lower fatty acid, and/or the above-mentioned alkali metal salt and/or alkaline earth metal salt, it is preferred to use a catalyst intermediate having a Pd/Pb atomic ratio of from 3/0.1 to 3/10.

The activation treatment of the catalyst intermediate can be conducted at room temperature to 200° C. under a pressure necessary for maintaining the reduction treatment system in a liquid state, preferably at 40 to 160° C. under atmospheric pressure to several atm.

The activation treatment time varies depending on the type of the catalyst active species and the activation treatment conditions, but is generally in the range of from several minutes to 100 hours. It is preferred to choose the activation treatment conditions so that the activation can be completed within several hours. Completion of the activation can be easily confirmed by measuring the diffraction angle (2θ) for a maximum intensity peak ascribed to the (111) crystal face diffraction with respect to the powder X-ray diffraction pattern of the catalyst obtained by the activation treatment.

The type of reactor used in the activation treatment is not specifically limited, and a conventional agitation vessel type reactor can generally be used.

(II-B-2-ii) With respect to the second method for activation of the catalyst intermediate, a detailed explanation is given below.

The second method for activation of the catalyst intermediate comprises oxidizing a catalyst intermediate and subsequently reducing the resultant oxidized catalyst intermediate, wherein:

(1) the oxidation is conducted using a gaseous oxidizing agent comprising molecular oxygen;
(2) the reduction is conducted using a gaseous reducing agent comprising at least one member selected from methanol gas, molecular hydrogen and $C_2$–$C_4$ olefin gas; and
(3) optionally, a sequence of the oxidation as in item (1) above and the reduction as in item (2) above is repeated.

In the case of the oxidation treatment using molecular oxygen, the catalyst intermediate is heated at a temperature of 200° C. or more, preferably from 200 to 600° C., for about 30 minutes or more, generally from 1 to 10 hours, while flowing pure oxygen gas or a gaseous mixture of oxygen gas and an inert gas (such as nitrogen gas or carbon dioxide gas) in which the oxygen concentration of the gaseous mixture is 0.1% or more by volume.

In the case of the reduction treatment using methanol gas, the catalyst intermediate is heated at a temperature of from 300 to 500° C., generally, for 1 to 10 hours under 1 to several atm, while flowing pure methanol gas or a gaseous mixture of methanol gas and an inert gas (such as nitrogen gas or methane gas) in which the methanol concentration of the gaseous mixture is 0.1% or more by volume. When the temperature of the reduction system is lower than 300° C., the activation operation cannot be conducted efficiently, and when the temperature of the system is higher than 500° C., a lowering of the activity of the catalyst is observed, which is believed to be ascribed to a sintering of metal particles.

In the case of the reduction treatment using molecular hydrogen (a hydrogen gas), the catalyst intermediate is heated at a temperature of from 200 to 500° C. for 1 to 10 hours under 1 to several tens atm, while flowing hydrogen gas. As in the case of the reduction treatment using methanol gas, when the temperature of the reduction system is lower than 200° C., the activation operation cannot be conducted efficiently, and when the temperature of the reduction system is higher than 500° C., a lowering of the activity of the catalyst is observed.

As mentioned above, the reduction of the oxidized catalyst intermediate is conducted using a gaseous reducing agent comprising at least one member selected from methanol gas, molecular hydrogen and $C_2$–$C_4$ olefin gas. In the last reduction treatment, it is preferred to use molecular hydrogen, rather than to use methanol gas and $C_2$–$C_4$ olefin gas.

For obtaining a catalyst having excellent properties, it is preferred to repeat a sequence of the oxidation treatment and reduction treatment, rather than to conduct the above-mentioned sequence only once. When the above-mentioned sequence is repeated, each sequence of the oxidation treatment (using a gaseous oxidizing agent comprising molecular oxygen) and the reduction treatment (using a gaseous reducing agent comprising at least one member selected from methanol gas, molecular hydrogen and $C_2$–$C_4$ olefin gas) can be conducted under substantially the same respective conditions as mentioned above. With respect to the times of repetition of the sequence, there is no particular limitation, as long as the catalyst of the present invention can be obtained, which comprises a carrier having supported thereon palladium and lead in a Pd/Pb atomic ratio (S) of $3/0.7 \leq S \leq 3/1.3$, and exhibits a maximum intensity peak at a diffraction angle (2θ) in the range of from 38.55° to 38.70° in the powder X-ray diffraction pattern thereof, wherein the peak is ascribed to the (111) crystal face diffraction of a Pd—Pb intermetallic compound. In practice, the times of repetition may vary depending on the type of the catalyst intermediate to be subjected to activation. However, the above-mentioned sequence is generally repeated 2 to 10 times.

The second activation method is especially advantageous for activating a catalyst intermediate which comprises a carrier having supported thereon palladium and lead in a Pd/Pb atomic ratio (S) of $3/0.7 \leq S \leq 3/1.3$, but does not satisfy the requirement of the catalyst of the present invention with respect to the X-ray diffraction pattern thereof. On the other hand, when a low purity catalyst intermediate which, for example, has a Pd/Pb atomic ratio (S) of $3/1.3 \leq S \leq 3/10$ is subjected to activation by the second activation method, even after the above-mentioned sequence of oxidation and reduction treatments is repeatedly conducted, a large amount of lead-containing impurities remains in the resultant catalyst intermediate. In this case, such a low purity catalyst intermediate can be supplementarily treated with a lower ($C_1$–$C_5$) fatty acid, such as formic acid, acetic acid, propionic acid, butyric acid, maleic acid and methacrylic acid so as to obtain a high purity catalyst having a Pd/Pb atomic ratio (S) of $3/0.7 \leq S \leq 3/1.3$.

Such a supplementary treatment with a lower ($C_1$–$C_5$) fatty acid is conducted by heating a dispersion of the above-mentioned low purity catalyst intermediate obtained by the second activation method in a solvent selected from water, an alcohol (such as methanol) and a mixture thereof. Other solvents than water and an alcohol (such as methanol) can also be used as a solvent for the treatment with a lower fatty acid as long as the solvents used are inert to the catalyst intermediate. However, the use of water is preferred from a practical point of view. The content of the lower fatty acid in the reaction system for the supplementary treatment is from 0.1 to 20% by weight. The supplementary treatment with a lower fatty acid is conducted at room temperature to 200° C., preferably at 40 to 160° C.

Instead of conducting the above supplementary treatment for converting the low purity catalyst intermediate obtained by the second activation method to a high purity catalyst of the present invention, the removal of the lead-containing impurities can be achieved, during the reaction for producing a carboxylic ester using the low purity catalyst intermediate obtained by the second activation method, by utilizing a carboxylic acid, such as methacrylic acid, which is by-produced during the reaction.

In the oxidation treatment, it is preferred to use an alkali metal salt and/or an alkaline earth metal salt, each of a $C_1$–$C_5$ fatty acid. The alkali metal salt and/or the alkaline earth metal salt is used in a molar amount of from 0.1 to 30 times, preferably from 1 to 15 times, as large as the molar amount of the palladium contained in the catalyst intermediate. The content of the alkali metal salt and/or the alkaline earth metal salt in the oxidation reaction system is from 0.1 to 20% by weight. Preferred examples of the alkali metal salt and the alkaline earth metal salt include sodium acetate and magnesium acetate. (The alkali metal salt and/or the alkaline earth metal salt, each of a lower fatty acid, can be used instead of the above-mentioned lower fatty acid in the above-mentioned supplementary treatment.) The alkali metal and/or the alkaline earth metal can be used in the form of an oxide, a hydroxide or a carbonate. In this case, each of the alkali metal compounds and each of the alkaline earth metal compounds can be used individually or in combination.

(II-B-2-iii) Hereinbelow, an explanation is provided on the third activation method. In the third activation method, a catalyst intermediate (which has been prepared by a conventional method) comprising a carrier having supported thereon palladium and lead, but having a large amount of lead (i.e., a Pd/Pb atomic ratio (S) of $3/2.5 \leq S \leq 3/10$) is treated with a lower ($C_1$–$C_5$) fatty acid in a solvent selected from water, an alcohol (such as methanol) and a mixture thereof. By this method, a high purity catalyst comprising a high quality $Pd_3Pb_1$ intermetallic compound having no or only few lattice defects can be obtained.

As mentioned above, the catalyst intermediate to be used in the third activation method is a catalyst (which has been prepared by a conventional method) comprising a carrier having supported thereon palladium and lead in a Pd/Pb atomic ratio (s) of $3/2.5 \leq S \leq 3/10$, preferably, $3/2.5 \leq S \leq 3/5$. Such a catalyst intermediate is of low purity, containing a large amount of lead impurities.

The third activation method comprises a simple operation of treating a catalyst intermediate comprising a carrier having supported thereon palladium and lead, but having a large amount of lead (i.e., a Pd/Pb atomic ratio (s) of $3/2.5 \leq S \leq 3/10$) with a lower ($C_1$–$C_5$) fatty acid. Illustratively stated, for example, as in Example 35 below, the third activation method can be conducted by dispersing the catalyst intermediate in an aqueous 0.1 to 20% by weight solution of, for example, acetic acid, and heating the resultant dispersion while stirring.

The lower ($C_1$–$C_5$) fatty acid to be used in the third activation method is selected from formic acid, acetic acid, propionic acid, butyric acid, maleic acid and methacrylic acid. From a commercial viewpoint, it is most preferred to use acetic acid which is easily available. It is preferred that the lower fatty acid be used in the form of a solution thereof in a solvent selected from water, an alcohol (such as methanol) and a mixture thereof, wherein the content of the lower fatty acid in the solution is from 0.1 to 20% by weight, more preferably from 1 to 15% by weight. Other solvents than water and alcohol (such as methanol) can be used in the activation treatment as long as the solvents used are stable and inert to the catalyst intermediate. However, it is preferred to use an aqueous solution of a lower fatty acid from a viewpoint of ease in preparation and handling thereof. When an inorganic acid, such as hydrochloric acid or sulfuric acid; an organic acid, such as paratoluenesulfonate; or the like is used for the activation instead of the lower fatty acid, a desired catalyst having excellent properties cannot be obtained. Therefore, in the third activation method, it is requisite to use a solution of the above-mentioned fatty acid in a solvent selected from water, an alcohol (such as methanol) and a mixture thereof, wherein the content of the fatty acid in the solvent does not exceed 20% by weight.

The lower fatty acid can be continuously added to a reactor during the activation treatment, or can be charged in a reactor together with the catalyst intermediate prior to the start of the activation treatment. Therefore, the amount of the lower fatty acid to be used for the activation treatment varies depending on the manner of activation treatment. However, the fatty acid can generally be used in a molar amount of from 10 to 1,000 times as large as the molar amount of the palladium contained in the catalyst intermediate.

Further, in the third activation method, it is preferred to use an alkali metal salt and/or an alkaline earth metal salt, each of a lower ($C_1$–$C_5$) fatty acid. The alkali metal salt and/or the alkaline earth metal salt, each of a lower fatty acid, can be used in a molar amount of from 0.1 to 30 times, preferably from 1 to 15 times, as large as the molar amount of the palladium contained in the catalyst intermediate. The content of the alkali metal salt and/or the alkaline earth metal salt in the activation reaction system is from 0.1 to 20% by weight. Preferred examples of alkali metal salts and alkaline earth metal salts include sodium acetate and magnesium acetate.

(The alkali metal salt and/or the alkaline earth metal salt can be used instead of the above-mentioned lower fatty acids.)

The alkali metal and/or the alkaline earth metal can be used in the form of a oxide thereof, a hydroxide thereof or a carbonate thereof. In this case, each of the alkali metal compounds and each of the alkaline earth metal compounds can be used individually or in combination.

The activation treatment of the catalyst intermediate can be conducted at room temperature to 200° C., preferably at 40 to 160° C.

The activation treatment time varies depending on the manner of the activation treatment, the treatment temperature and the type of the catalyst intermediate. However, when the activation treatment time is too long, a lowering of the performance of the catalyst is likely to occur. The treatment time is generally in the range of from 0.1 to 100 hours, preferably from 0.5 to 20 hours.

In the third activation method, the activation treatment can be conducted using an agitation vessel type reactor, a bubble column reactor or the like, in which the catalyst intermediate is used in the form of a slurry obtained by dispersing the catalyst intermediate in the above-mentioned solvent. In this case, the content of the catalyst intermediate in the slurry is generally from 0.04 to 0.5 kg/liter of the reaction system. Alternatively, the activation can be conducted by charging the catalyst intermediate in a fixed-bed reactor, and flowing a solution containing a lower fatty acid through the reactor.

(II-B-2-iv) A detailed explanation will be given on the fourth activation method in the present invention. The fourth activation method is a simple method in which the activation of a catalyst intermediate is conducted simply by reacting the catalyst intermediate with an alcohol or a mixture of an alcohol and an aldehyde in the presence of lead ions and under a specific oxygen partial pressure, to thereby obtain a catalyst of the present invention.

Examples of aldehydes usable for the activation include formaldehyde; $C_1$–$C_{10}$ aliphatic saturated aldehydes, such as acetoaldehyde, propionaldehyde, isobutylaldehyde and glyoxal; $C_3$–$C_{10}$ aliphatic $\alpha$·$\beta$-unsaturated aldehydes, such as acrolein, methacrolein and crotonaldehyde; $C_6$–$C_{20}$ aromatic aldehydes, such as benzaldehyde, tolylaldehyde, benzylaldehyde and phthalaldehyde, and derivatives of these aldehydes. The above-mentioned aldehydes may be used alone or as a mixture of two or more aldehydes.

Examples of alcohols include $C_1$–$C_{10}$ aliphatic saturated alcohols, such as methanol, ethanol, isopropanol and octanol; $C_2$–$C_{10}$ diols, such as ethylene glycol and butanediol; $C_3$–$C_{10}$ aliphatic unsaturated alcohols, such as allyl alcohol and methallyl alcohol; and $C_6$–$C_{20}$ aromatic alcohols, such as benzyl alcohol. The above-mentioned alcohols may be used alone or as a mixture of two or more alcohols.

There is no particular limitation with respect to the ratio of an aldehyde to an alcohol in the mixture of an aldehyde and an alcohol to be used in the reaction. For example, the molar ratio of an aldehyde to an alcohol may be chosen within the wide range of from 1/1,000 to 10/1. Generally, the molar ratio of an aldehyde to an alcohol may be in the range from 1/2 to 1/50. Alternatively, an alcohol may be used alone for the reaction.

In the fourth activation method, the activation of the catalyst intermediate can be conducted simultaneously with production of a carboxylic ester in a single reaction system and, hence, the fourth activation method has great practical significance. For example, when the activation of a catalyst intermediate is conducted to produce a catalyst for MMA production while conducting the production of MMA simultaneously, methacrolein and methanol can be advantageously used as an aldehyde and an alcohol, respectively.

The amount of the catalyst intermediate to be used in the fourth activation method is not specifically limited, and may largely vary depending on the types of the aldehyde and alcohol to be used, the type of the catalyst intermediate, and the reaction conditions and the like. However, for example, when the catalyst intermediate is activated in a slurry form, it is preferred to use the catalyst intermediate in an amount of from 0.04 to 0.5 kg per liter of the slurry.

In the fourth activation method, as in the first to the third activation methods, it is requisite that lead ions be present in the reaction system. For this purpose a lead-containing substance is usually added to the reaction system. The type of the lead-containing substance is not specifically limited as long as it can be dissolved in the reaction system to produce lead ions. Examples of lead-containing substances include lead salts of organic acids, such as formic acid and acetic acid; and lead salts of inorganic acids, such as sulfuric acid, hydrochloric acid and nitric acid, and also include lead oxide; lead hydroxide; and lead powder. Among them, lead nitrate and lead acetate are preferred because these lead salts have high solubility.

The amount of the lead-containing substance to be added may be varied depending on the type of the catalyst intermediate used. An appropriate amount of the lead-containing substance is chosen from the range of 3/0.01 to 3/2 in terms of the (Pd/Pb) atomic ratio of the Pd present on the catalyst intermediate to the Pb contained in the lead-containing substance, and the lead-containing substance is dissolved or dispersed in an alcohol or a mixture of an aldehyde and an alcohol. The lead-containing substance can be continuously or intermittently added prior to or during the activation treatment. The lead concentration in the alcohol or in the mixture of the alcohol and the aldehyde is not specifically limited. However, the lead concentration of the reaction system is generally 0.1 to 2,000 ppm, usually from 1 to 200 ppm. When it is desired to shorten the time for the activation treatment, it is preferred to increase the lead concentration.

In the fourth activation method, for obtaining a catalyst comprising a carrier having supported thereon palladium and lead in a Pd/Pb atomic ratio (S) in the range of $3/0.7 \leq S \leq 3/1.3$, and for achieving a Pd/Pb atomic ratio as close to 3/1 as possible, it is preferred that the amount of the lead-containing substance be chosen from the range of 3/0.03 to 3/0.6 in terms of the (Pd/Pb) atomic ratio of the Pd present on the intermediate to the Pb contained in the lead-containing substance.

As mentioned above, for providing lead ions in the reaction system for the activation treatment, a lead-containing substance is generally added to the reaction system. However, when the catalyst intermediate to be subjected to activation is of low purity, for example when the catalyst intermediate has a Pd/Pb atomic ratio of from 3/1.3 to 3/3, such a catalyst intermediate has a large amount of lead-containing impurities, such as lead oxides and metallic lead. In such a case, instead of adding a separate lead-containing substance, these lead-containing impurities contained in the catalyst intermediate can be utilized as the source of lead ions, that is, the lead component is dissolved out from the catalyst composition in an ionized form into the reaction system. In this case, for facilitating the dissolution-out of the lead component from the lead-containing impurities into the reaction system, it is preferred that a lower ($C_1$–$C_5$) fatty acid, such as propionic acid, acetic acid, butyric acid, maleic acid or methacrylic acid, be added to the reaction system. Among these lower fatty acids, acetic acid is most preferred because it is easily available. The lower fatty acid can be used in a molar amount of from 0.1 to 30 times, preferably from 1 to 15 times as large as the molar amount of the palladium present on the catalyst intermediate. When the activation of the catalyst intermediate is conducted while continuously feeding an alcohol or a mixture of an aldehyde and an alcohol, the concentration of the lower fatty acid in the reaction system is chosen from the range of from 0.1 to 20 weight %.

When a lower fatty acid, such as methacrylic acid or the like is by-produced from the aldehyde and the alcohol during the activation reaction, the amount of a lower fatty acid to be added to the reaction system may be decreased or the addition of a lower fatty acid may be omitted.

The lower fatty acid may be added to the reaction system simultaneously with the start of the activation reaction. However, it is preferred to add the lower fatty acid to the reaction system prior to the start of the activation reaction, since a sufficient amount of lead to conduct the activation can be dissolved out from the catalyst intermediate. Even when a lead-containing substance is added to provide lead ions in the reaction system, the addition of a lower fatty acid is preferable since the amount of a lead-containing substance to be added to the reaction system can be decreased.

In the fourth activation method, it is important that the oxygen partial pressure at the outlet of the reactor be 0.8 kg/cm$^2$ or lower. The oxygen partial pressure is preferably 0.4 kg/cm$^2$ or lower. The oxygen partial pressure at the outlet of the reactor may be 0 kg/cm$^2$.

The oxygen to be used in the activation of the catalyst intermediate is molecular oxygen, which may be in the form of oxygen gas or a gas mixture of an oxygen gas and an inert diluent gas, such as nitrogen gas and carbon dioxide gas. Molecular oxygen may be provided in the form of air. In any case, it is important to control the amount of oxygen to be introduced to the reactor so as to give an oxygen partial pressure of 0.8 kg/cm$^2$ or less as measured at the outlet of the reactor. The lower the oxygen partial pressure at the outlet of the reactor, the smaller the necessary lead concentration for the activation of the catalyst intermediate. Therefore, a lowering of the oxygen partial pressure at the outlet of the reactor contributes to a decrease in amount of lead values dissolved-out into the waste water from the process for the production of carboxylic esters, thereby enabling the cost for detoxifying the lead contained in the waste water to be decreased. Thus, in practice, a minimum necessary amount of lead is chosen from the range of from 1 to 200 ppm, and it is preferable that the oxygen partial pressure at the outlet of the reactor be 0.4 km/cm$^2$ or less.

The catalyst intermediate which can be preferably used in the fourth activation method is a catalyst intermediate having a Pd/Pb atomic ratio (S) of $3/0 \leq S \leq 3/10$. However, for example, when the catalyst intermediate comprises a carrier having supported thereon palladium and lead in a Pd/Pb atomic ratio (S) of $3/1.3 \leq S \leq 3/10$, practically $3/1.3 \leq S \leq 3/3$, such a catalyst intermediate contains a large amount of lead-containing impurities. In the activation of such a low purity catalyst intermediate, it is desired to make an effective use of lead-containing impurities as a source of lead ions. In such a case, the oxygen partial pressure at the outlet of the reactor is set at a relatively high value. Thus, it is necessary that the oxygen partial pressure and the lead concentration in the reaction system be varied within the ranges mentioned above, depending on the properties of the catalyst intermediate to be used.

The activation of the catalyst intermediate may be performed under pressure in a wide range, i.e., from reduced pressure to superatmospheric pressure. Generally, the activation reaction is conducted under a pressure of from 0.5 to 20 kg/cm$^2$, in terms of the total of the pressure of molecular oxygen, the pressure of an inert gas, if any, and the vapor pressure of a solvent. The total pressure should be chosen so that the oxygen concentration of a gas flowing out from the reactor does not exceed the explosion limit (8%).

The fourth activation method may be performed at room temperature to 200° C. under a pressure necessary for maintaining the reaction system in a liquid state. It is preferred that the reaction be conducted at 40 to 160° C. under atmospheric pressure to several atm. The activation reaction time in the fourth activation method varies depending on the type of the catalyst intermediate and the activation reaction conditions, but is generally in the range of from several hours to 500 hours. It is preferred to choose the activation reaction conditions so that the reaction can be completed within 100 hours.

(II-B-2-v) The type of reactor to be used in the activation treatment is not specifically limited, and a conventional agitation vessel type reactor can be used.

By subjecting a catalyst intermediate to an activation treatment by using one of the first to fourth activation methods described above, a catalyst of the present invention containing, with high purity, a high quality Pd$_3$Pb$_1$ intermetallic compound having no or only few lattice defects can be obtained, wherein the catalyst comprises a carrier having supported thereon palladium and lead in a Pd/Pb atomic ratio (S) of $3/0.7 \leq S \leq 3/1.3$, and exhibits a maximum intensity peak at a diffraction angle (2θ) in the range of from 38.55° to 38.70° in a powder X-ray diffraction pattern thereof, wherein the peak is ascribed to the (111) crystal face diffraction of a Pd—Pb intermetallic compound.

By these activation methods, a high quality catalyst having a Pd/Pb atomic ratio as close to 3/1 as possible can be produced. For example, by subjecting, to an appropriately selected activation method, a low purity catalyst intermediate containing lead in an excess amount such that the amount of lead in the catalyst is larger than the amount corresponding to the Pb/Pd atomic ratio of 3/2.5, a high purity catalyst having a Pd/Pb atomic ratio as close to 3/1 as possible can be produced. As described above, with respect to a conventional catalyst obtained using a conventional catalyst preparation method, even if the catalyst has a Pb/Pd atomic ratio close to 3/1, it is inevitably a low purity, low quality catalyst having many lattice defects and containing a large amount of impurities, such as lead oxides and metallic lead. Such a conventional catalyst results in a poor selectivity for a desired carboxylic ester. The above-mentioned preparation method of the present invention has rendered it possible to obtain a catalyst which has conventionally been impossible to produce, namely, a high quality, high purity catalyst having not only a Pd/Pb atomic ratio close to 3/1 but also having no or only few lattice defects, wherein the catalyst exhibits specific X-ray diffraction characteristics. Thus, not only can an improved selectivity for a desired carboxylic ester, such as MMA, be achieved, whereby the formation of a by-product derived from the alcohol, for example, methyl formate is greatly suppressed, but also the small content of lead impurities in the catalyst contributes to a decrease in dissolution-out of lead values into the waste water from the process for the production of carboxylic esters, thereby enabling the treatment cost for detoxifying the lead values contained in the waste water to be obviated. Therefore, various significant practical advantages can be brought about by the present invention.

III. Control of the Surface Structure of the Catalyst

Hereinbelow, an explanation is made on a catalyst comprising a carrier having supported thereon palladium and lead, which catalyst has a controlled surface structure, and which catalyst is one of the preferred embodiments of the present invention, and on a method for obtaining such a catalyst having a controlled surface structure.

The surface structure-controlled catalyst comprising a carrier having supported thereon palladium and lead is a catalyst which exhibits, in a spectrum obtained from the catalyst by X-ray photoelectron spectroscopy, a ratio of from 1/0.2 to 1/0.7 in terms of the {Pd3d(3/2)+Pd3d(5/2)}/{Pb4f(7/2)×1.75} ratio of the sum of respective intensities of two peaks respectively ascribed to the 3d(3/2) electron and the 3d(5/2) electron of metallic palladium to the intensity of a peak ascribed to the 4f(7/2) electron of metallic lead which is multiplied by 1.75. Such a surface structure-controlled catalyst may be simultaneously formed at the time that a catalyst intermediate is subjected to any one of the above four activation methods (i.e., the first to fourth activation methods) depending on the conditions employed. However, such a surface structure-controlled catalyst can be positively, surely obtained by employing the following methods.

In the above-mentioned fourth activation method, the activation treatment is conducted, wherein:

1) the range of partial pressure of oxygen is further limited; or 2) instead of a catalyst intermediate, a catalyst of the present invention, which comprises a carrier having supported thereon palladium and lead in a Pd/Pb atomic ratio (S) of $3/0.7 \leq S \leq 3/1.3$, is subjected to activation treatment.

In the surface structure-controlling method 1) above, there is no particular limitation with respect to the catalyst intermediate to be employed. On the other hand, in the surface structure-controlling method 2) above, instead of a catalyst intermediate, use is made of a catalyst which comprises a carrier having supported thereon palladium and lead in a Pd/Pb atomic ratio (S) of $3/0.7 \leq S \leq 3/1.3$, exhibiting a maximum intensity peak at a diffraction angle ($2\theta$) in the range of from 38.55° to 38.70° in a powder X-ray diffraction pattern thereof, wherein the peak is ascribed to the (111) crystal face diffraction of a Pd—Pb intermetallic compound.

In each of the above surface structure-controlling methods, an alcohol or a mixture of an alcohol and an aldehyde is used as in the above fourth activation method. The type of each of an alcohol and an aldehyde and the ratio of an aldehyde to an alcohol in the mixture of an aldehyde and an alcohol are the same as in the fourth activation method.

In each of the surface-controlling methods, it is requisite that lead ions be present in the reaction system for the surface controlling treatment. For this purpose, a lead-containing substance is usually added to a dispersion of a starting catalyst to be subjected to surface-controlling treatment (i.e., the catalyst intermediate, or the catalyst of the present invention) in water, methanol or a mixture thereof. The type of lead-containing substance is not specifically limited as long as it can be dissolved in the form of lead ions. Examples of lead-containing substances include lead salts of organic acids, such as formic acid and acetic acid; and lead salts of inorganic acids, such as sulfuric acid, hydrochloric acid and nitric acid, and also include lead oxide; and lead hydroxide. Among them, lead nitrate and lead acetate are preferred because these lead salts have high solubility.

In each of the surface-controlling methods, the amount of a lead-containing substance to be added may be varied depending on the type of the starting catalyst to be subjected to surface structure-controlling treatment. Generally, an appropriate amount of lead-containing substance is chosen within the range of from 3/0.01 to 3/2 in terms of the atomic ratio of the Pd contained in the starting catalyst to the Pb contained in the lead-containing substance, and the starting catalyst is dispersed in a solution of the lead-containing substance in water and/or methanol, and the surface structure-controlling operation is conducted.

The lead-containing substance can be continuously or intermittently added prior to or during the surface structure-controlling treatment. The lead concentration in an alcohol or a mixture of an alcohol and an aldehyde varies depending upon the manner of addition of the lead-containing substance into the activation reaction system, but the lead concentration is generally from 0.1 to 2,000 ppm, preferably from 1 to 200 ppm. When it is desired to shorten the period of time required for the surface structure-controlling treatment, it is recommended to employ a high concentration of lead.

For obtaining a catalyst comprising a carrier having supported thereon palladium and lead in a Pd/Pb atomic ratio of 3/0.7 to 3/1.3 in method 1) above, preferably in a Pd/Pb atomic ratio as close to 3/1 as possible in each of methods 1) and 2) above, it is preferred that the amount of the lead-containing substance added to the reaction system for surface structure-controlling treatment be in the range of from 3/0.03 to 3/0.6 in terms of the Pd/Pb atomic ratio of Pd contained in the starting catalyst to Pb contained in the lead-containing substance.

As mentioned above, for providing lead ions in the reaction system for surface structure-controlling treatment, a lead-containing substance is generally used. However, in method 1) above, when the catalyst intermediate to be subjected to surface structure-controlling treatment is of low purity (which, for example, has a Pd/Pb ratio (S) of $3/1.3 \leq S \leq 3/3$), such a catalyst intermediate has a large amount of lead impurities.

In this case, for facilitating the dissolution-out of lead component from the lead-containing impurities into the reaction system, it is preferred that a lower ($C_1$–$C_5$) fatty acid, such as propionic acid, acetic acid, butyric acid, maleic acid or methacrylic acid, be added to the surface structure-controlling reaction system. Among these lower fatty acids, acetic acid is most preferred because it is easily available. The lower fatty acid can be used in a molar amount of from 0.1 to 30 times, preferably from 1 to 15 times, as large as the molar amount of the palladium present on the catalyst intermediate. When the surface structure-controlling treatment is conducted while continuously feeding an alcohol or a mixture of an alcohol and an aldehyde, it is preferred that the concentration of the lower fatty acid in the reaction system be selected from the range of from 0.1 to 20% by weight.

When a lower fatty acid, such as methacrylic acid or the like, is by-produced from the aldehyde or the alcohol in the reaction system during the surface structure-controlling treatment, the amount of a lower fatty acid to be added in the reaction system may be reduced or the addition of a lower fatty acid may be omitted.

The lower fatty acid may be added to the reaction system during the surface structure-controlling treatment. However, it is preferred to add the lower fatty acid to the reaction system prior to the start of the surface structure-controlling treatment, because a sufficient amount of lead to conduct the surface structure-controlling treatment can be dissolved out from the catalyst intermediate. Further, even when a lead-containing substance is added to provide lead ions in the reaction system, it is advantageous to use a lower fatty acid since, for example, the amount of a lead-containing substance to be added to the reaction system can be reduced.

In the surface structure-controlling treatment, it is preferred to use an alkali metal salt and/or an alkaline earth metal salt, each of a lower ($C_1$–$C_5$) fatty acid. Specifically, it is preferred that an alkali metal salt and/or an alkaline earth metal salt, each of a lower fatty acid be used in a molar amount of from 0.1 to 30 times, more preferably from 1 to 15 times as large as the molar amount of the palladium contained in the catalyst intermediate. When the surface structure-controlling treatment is conducted while continuously feeding an alcohol or a mixture of an alcohol and an aldehyde, it is preferred that the concentration of the lower fatty acid in the reaction system be selected from the range of from 0.1 to 20% by weight. Preferred examples of alkali metal salts and alkaline earth metal salts include sodium acetate and magnesium acetate. (These alkali metal salts and alkaline earth metal salts can be used as a substitute for the above-mentioned lower fatty acid.)

The alkali metal and/or the alkaline earth metal may be used in the form of an oxide, a hydroxide or a carbonate. In this case, each of the alkali metal compounds and each of the alkaline earth metal compounds may be used individually or in combination.

In the surface structure controlling treatment method 1) above, there is no particular limitation with respect to the type of a catalyst intermediate to be employed, which comprises a carrier having palladium and lead supported thereon. However, it is requisite that the reaction of the catalyst intermediate with the alcohol or the mixture of an alcohol and an aldehyde be conducted under the conditions such that the partial pressure of oxygen is 0 to 0.4 kg/cm$^2$, preferably 0 to 0.2 kg/cm$^2$, at the outlet of the reactor.

Oxygen is used in the form of molecular oxygen (i.e., oxygen gas) or a gaseous mixture of oxygen gas and an inert gas (such as nitrogen gas or carbon dioxide gas). Air also can be used. Irrespective of the form of oxygen employed, it is requisite that the partial pressure of oxygen be 0.4 kg/cm$^2$ or less at the outlet of the reactor.

In method 1) above, the lower the partial pressure of oxygen at the outlet of the reactor, the smaller the amount of lead necessary for the surface structure-controlling treatment. However, when the catalyst intermediate to be subjected to surface structure-controlling treatment is of low purity (which, for example, has a Pd/Pb atomic ratio (S) of $3/1.3 \leq S \leq 3/3$), such a catalyst intermediate has a large amount of lead impurities. In this case, it is preferred to utilize the lead component contained as impurities. In this instance, a relatively high partial pressure of oxygen is chosen within the above-mentioned range. Accordingly, the partial pressure of oxygen and the amount of lead to be added should be appropriately chosen within the respective ranges as mentioned above, depending on the type of the catalyst intermediate to be used.

The surface structure-controlling treatment 2) mentioned above is explained in detail below.

It is important that the catalyst to be subjected to the surface structure-controlling treatment 2) be the specific catalyst mentioned above. The oxygen partial pressure at the outlet of the reactor is in the range of from 0 to 0.8 kg/cm$^2$, preferably from 0 to 0.4 kg/cm$^2$.

The oxygen to be used is molecular oxygen, which may be in the form of oxygen gas or a gas mixture of an oxygen gas and an inert diluent gas, such as nitrogen gas and carbon dioxide gas. Molecular oxygen may be provided in the form of air. In any case, it is important to control the amount of oxygen to be introduced to the reactor so as to give an oxygen partial pressure of 0.8 kg/cm$^2$ or less as measured at the outlet of the reactor. The lower the oxygen partial pressure at the outlet of the reactor, the smaller the necessary lead concentration for the surface structure-controlling treatment.

The surface structure-controlling treatment can be conducted under pressure in a wide range, from reduced pressure to superatmospheric pressure. Generally, the treatment is conducted under a pressure of from 0.5 to 20 kg/cm$^2$. The pressure should be chosen so that the oxygen concentration of gas flowing out from the reactor does not exceed the explosion limit (8%).

The surface structure-controlling treatment can be conducted at room temperature to 200° C. under a pressure necessary for maintaining the reaction system in a liquid state. It is preferred that the reaction be conducted at 40 to 160° C. under atmospheric pressure to several atm.

The time required for the surface structure controlling-treatment varies depending on the type of the catalyst and the treatment reaction conditions. However, generally, the treatment time is in the range of from several hours to 500 hours. It is favorable to choose the treatment reaction conditions so that the treatment may be completed within 100 hours.

The type of reactor to be used in the surface structure-controlling treatment is not specifically limited, and a conventional agitation vessel type reactor can be used.

By conducting the surface structure-controlling treatment as explained above with reference to the above-mentioned treatments 1) and 2), it is possible to obtain the most preferable form of the catalyst of the present invention, i.e., a catalyst comprising a carrier having supported thereon palladium and lead in a Pd/Pb atomic ratio (S) of $3/0.7 \leq S \leq 3/1.3$, which catalyst exhibits a maximum intensity peak at a diffraction angle (2θ) in the range of from 38.55° to 38.70° in a powder X-ray diffraction thereof, the peak being ascribed to the (111) crystal face diffraction of a Pd—Pb intermetallic compound, and which catalyst exhibits, in a spectrum obtained from the catalyst by X-ray photoelectron spectroscopy, a ratio of from 1/0.2 to 1/0.7 in terms of the $\{Pd3d(3/2)+Pd3d(5/2)\}/\{Pd4f(7/2)\times 1.75\}$ ratio of the sum of respective intensities of two peaks respectively ascribed to the 3d(3/2) electron and the 3d(5/2) electron of metallic palladium to the intensity of a peak ascribed to the 4f(7/2) electron of metallic lead which is multiplied by 1.75.

IV. Production of a Carboxylic Ester

The catalyst of the present invention can be suitably used for reacting an aldehyde, an alcohol and molecular oxygen to produce a carboxylic ester. The amount of the catalyst is not specifically limited, and may be greatly varied, depending on the types of the starting materials for the reaction, the composition and preparation method of the catalyst, the reaction conditions and the mode of the reaction process. However, when the reaction is conducted using the catalyst in a slurry form, it is preferred to use the catalyst in an amount of 0.04 to 0.5 kg per liter of the reaction system.

Examples of aldehydes to be used in the method of the present invention for the production of a carboxylic ester include formaldehyde; $C_1$–$C_{10}$ aliphatic saturated aldehydes, such as acetoaldehyde, propionaldehyde, isobutylaldehyde and glyoxal; $C_3$–$C_{10}$ aliphatic α·β-unsaturated aldehydes, such as acrolein, methacrolein and crotonaldehyde; $C_6$–$C_{20}$ aromatic aldehydes, such as benzaldehyde, tolylaldehyde, benzylaldehyde and phthalaldehyde; and derivatives of these aldehydes. These aldehydes may be used alone or as a mixture of two or more aldehydes.

Examples of alcohols to be used in the method of the present invention for the production of a carboxylic ester include $C_1$–$C_{10}$ aliphatic saturated alcohols, such as methanol, ethanol, isopropanol and octanol; $C_2$–$C_{10}$ diols, such as ethylene glycol and butanediol; $C_3$–$C_{10}$ aliphatic unsaturated alcohols, such as allyl alcohol and methallyl alcohol; and $C_6$–$C_{20}$ aromatic alcohols, such as benzyl alcohol. These alcohols may be used alone or as a mixture of two or more alcohols.

In the method of the present invention for the production of a carboxylic ester, there is no particular limitation with respect to the ratio of an aldehyde to an alcohol in the reaction system. For example, the molar ratio of an aldehyde to an alcohol may be chosen within the wide range of from 1/1,000 to 10/1. Generally, the molar ratio of an aldehyde to an alcohol may be in the range from 1/2 to 1/50.

In the method of the present invention for the production of a carboxylic ester, any conventional reaction process, such as gas phase reaction, liquid phase reaction and trickle bed reaction may be employed. For example, when the method of the present invention is conducted by liquid phase reaction, any known reactor, such as a bubble column reactor, a draft tube reactor or an agitation type reactor, may be employed The oxygen to be used in the method of the present invention for the production of a carboxylic ester is molecular oxygen, which may be in the form of oxygen gas or a gas mixture of an oxygen gas and an inert diluent gas, such as nitrogen gas and carbon dioxide gas. Molecular oxygen may be provided in the form of air.

The reaction may be performed under pressure in a wide range from reduced pressure to superatmospheric pressure. Generally, the reaction is conducted under a pressure of from 0.5 to 20 kg/cm$^2$. The pressure should be chosen so that the oxygen concentration of gas flowing out from the reactor does not exceed the explosion limit (8%).

In the method of the present invention for the production of a carboxylic ester, it is preferred that an alkali metal compound or an alkaline earth metal compound (for example, an oxide, a hydroxide, a carbonate or a carboxylate) be added so as to maintain the reaction system at a pH of 6 to 9. By maintaining a pH of 6 or more, the dissolution-out of a lead component from the catalyst can be effectively prevented.

Alkali metal compounds and alkaline earth metal compounds may be used alone or in combination of two or more compounds.

When the concentration of the aldehyde in the reaction system is high, the reaction can be carried out even at a temperature higher than 100° C. However, a reaction temperature of from 30 to 100° C. is preferred, and a reaction temperature of from 60 to 90° C. is more preferred. The reaction time varies depending on the reaction conditions, but is generally in the range of from 1 hour to 20 hours.

V. Continuous Production of a Carboxylic Ester by Using a Catalyst and Stabilization of the Catalyst In a method for producing a carboxylic ester from an aldehyde, an alcohol and molecular oxygen, also a stabilization of the catalyst is achieved simultaneously with the reaction for producing a carboxylic ester (the simultaneous stabilization of the catalyst has become possible for the first time by the use of the catalyst of the present invention), and a desired carboxylic ester can be produced continuously and efficiently.

Hereinbelow, an explanation is made on an advantageous method for continuously producing a carboxylic ester by using a catalyst of the present invention, wherein the reaction is performed while effecting a stabilization of the catalyst.

In a method for producing a carboxylic ester from an aldehyde, an alcohol and molecular oxygen by using a catalyst comprising a carrier having palladium and lead supported thereon, the performance of the catalyst is likely to be lowered with the lapse of production operation time. The present inventors have analyzed the catalyst which has deteriorated during the reaction, and have made investigations with a view toward finding a cause for the lowering of the performance of the catalyst. As a result, it has been found that the lead content of the deteriorated catalyst has become lowered and, accordingly, the reaction system has been caused to contain lead ions in a concentration of from about 0.1 to several ppm. On the other hand, in Example 10 of Examined Japanese Patent Application Publication No. 62-007902, a reaction for producing a carboxylic ester is conducted in a trickle bed reactor. In this Example, it is disclosed that no change is observed with respect to the results of the reaction even at a point in time of 2,000 hours after the start of the reaction. The present inventors have examined the catalyst used in this reaction, and found that the lead content of the catalyst was stably maintained at an almost satisfactory level. The above-mentioned two facts suggest that, as explained below in detail, the degrees of dissolution-out of lead from the catalyst and lowering of the performance of the catalyst largely vary depending on the reaction conditions and the mode of reaction. In these situations, the present inventors have made intensive studies on the mechanism of the dissolution-out of lead from the catalyst (which leads to a lowering of the performance of the catalyst). As a result, it has been found that, when the reaction is conducted in a reactor while adding to the reactor a lead-containing substance in a small amount, without withdrawing the catalyst from the reactor, the lead values of the lead-containing substance, which are present in the reaction system in the form of lead ions, are taken into the catalyst so that deterioration of the catalyst can be suppressed. The reason why the lead values of the lead-containing substance are taken into the catalyst resides in that even under reaction conditions such that the lead in the catalyst is likely to dissolve out in the form of lead ions, the lead ions of the lead-containing substance are reduced and taken into the catalyst. This is unexpected and surprising. Although it is conceivable that when the lead-containing substance is contained in the reaction system in the form of lead ions, the dissolution equilibrium of lead in the reaction system shifts to the side of non-dissolution, a phenomenon that a part of the lead ions in the reaction system is reduced to metallic lead and taken into the catalyst is unexpected and cannot be explained simply, based on the dissolution equilibrium. The present inventors have also found that when the oxygen concentration of the reaction system is within a specific range, the deterioration of the catalyst during the reaction can be suppressed even when the amount of lead added as the lead-containing substance to the reactor is small.

The lead concentration of the reaction system, which is employable for stabilizing the catalyst, is not specifically limited, but generally in the range of from 1 to 2,000 ppm by weight. However, it is generally preferred that the lead concentration of the reaction system be low. As mentioned below, the lead concentration can be lowered to a level as low as 200 ppm or less, preferably 100 ppm or less, by controlling the oxygen concentration of the reaction system.

As mentioned above, in the method of the present invention for continuously producing a carboxylic ester, which comprises continuously reacting an aldehyde, an alcohol and molecular oxygen in a reactor in the presence of the catalyst comprising a carrier having supported thereon palladium and lead, wherein the reaction is performed while adding a lead-containing substance to the reactor, the deterioration of the catalyst can be suppressed, so that a desired carboxylic ester can be continuously and stably produced. By maintaining the partial pressure of oxygen at the outlet of the reactor at 0.8 kg/cm$^2$ or less, the deterioration of the catalyst can be suppressed even when the lead concentration of the reaction system is further lowered.

It can be said that the above-mentioned effect of suppression of the deterioration of the catalyst during the reaction has been achieved, based on the following two findings: (1) a lowering of the performance of the catalyst can be suppressed when the reaction is conducted while adding a lead-containing substance to the reaction system; and (2) the amount of lead-containing substance necessary for stabilizing the catalyst can be reduced when the oxygen concentration of the reaction system is maintained at a certain level. The mechanism of suppression of the deterioration of the catalyst is explained below in more detail.

In the present invention, when the reaction for producing a carboxylic ester is conducted at a high aldehyde concentration and at a high reaction temperature, the oxidation of the aldehyde is likely to occur markedly, so that the by-production of water is sharply increased and the formation of an undesired carboxylic acid, such as methacrylic acid, is likely to occur rather than the formation of a desired carboxylic ester, such as methyl methacrylate (MMA). In addition, it is believed that the dissolution-out of lead from the catalyst is accelerated by the presence of such an undesired carboxylic acid that is formed, and that, therefore, the deterioration of the catalyst occurs vigorously at high aldehyde concentration and high reaction temperature conditions. However, according to the above-mentioned preferred mode of the method of the present invention, the deterioration of the catalyst can be effectively suppressed even without selecting special reaction modes or reaction conditions for suppressing the formation of a carboxylic acid as a by-product, so that the method for continuously producing a carboxylic ester can be advantageously practiced.

In the above-mentioned method for suppressing the deterioration of the catalyst used while producing a carboxylic ester, wherein the reaction is conducted in a reactor while adding to the reactor a lead-containing substance in a small amount, even under reaction conditions such that the dissolution-out of lead from the catalyst is likely to occur, the lead values of the lead-containing substance are effectively taken into the catalyst, thereby stabilizing the catalyst. However, the mechanism of this has not yet been elucidated. It is presumed that, under the reaction conditions for producing a carboxylic ester, activated hydrogen which is formed on the catalyst containing palladium serves to reduce lead ions to metallic lead, which in turn is taken into the catalyst.

As mentioned above, according to this preferred mode of the method of the present invention, it has for the first time been realized to produce a desired carboxylic ester continuously and efficiently without suffering from deterioration of the catalyst by a simple method, i.e., by adding a lead-containing substance to feedstocks fed to the reactor.

Further, with a view that, in the method of producing a carboxylic ester while stabilizing the catalyst, activated hydrogen formed on the catalyst containing palladium plays an important role in stabilization of the catalyst, the present inventors have attempted to control the amount of oxygen fed to the reactor so that the oxygen partial pressure at the outlet of the reactor does not exceed a certain level. As a result, the present inventors have succeeded in enhancing the activity of the activated hydrogen, so that the lead of the lead-containing substance can be effectively taken into the catalyst, even when the lead-containing substance is added to the reactor in a small amount When the oxygen partial pressure at the outlet of the reactor is 0.8 kg/cm$^2$ or less, the amount of lead-containing substance added to the reactor can be reduced. When the oxygen partial pressure at the outlet of the reactor is 0.4 kg/cm$^2$ or less, the lead concentration of the reaction system can be advantageously lowered to 1 to 200 ppm.

The type of lead-containing substance to be added to the reaction system according to the above-mentioned stabilization of the catalyst is not specifically limited as long as it can be dissolved in the reaction system in the form of lead ions.

Examples of lead-containing substances include lead salts of organic acids, such as formic acid and acetic acid; lead salts of inorganic acids, such as sulfuric acid, hydrochloric acid and nitric acid, and also include lead oxide and lead hydroxide. Among them, lead nitrate and lead acetate are preferred because these lead salts have high solubility. When the amount of lead-containing substance added is large, there are disadvantages such that the treatment cost for detoxifying the lead contained in the waste water from the process for production of carboxylic esters becomes high and the by-production of methyl formate is increased. For obviating such disadvantages, it is preferred to reduce the amount of lead-containing substance by lowering the oxygen partial pressure at the outlet of the reactor to 0.4 kg/cm$^2$ or less, more preferably 0.2 kg/cm$^2$ or less. However, it is preferred to choose an oxygen partial pressure such that the amount of oxygen necessary for conducting the carboxylic ester-forming reaction can be secured. When the amount of oxygen is too small, there are adverse effects, such as low conversion of an aldehyde as a starting material and formation of an undesired by-product. Therefore, it is preferred to choose an oxygen partial pressure from the range such that the above-mentioned adverse effects due to lack of oxygen can be avoided.

By stabilizing the catalyst of the present invention comprising a carrier having palladium and lead supported thereon in such a manner as mentioned above, the catalyst can be maintained at a state which is essential to the catalyst of the present invention, i.e., a state satisfying requirements such that the catalyst has a Pd/Pb atomic ratio of 3/0.7 to 3/1.3 and exhibits a maximum intensity peak at a diffraction angle (2θ) in the range of from 38.55° to 38.70° in a powder X-ray diffraction pattern thereof, wherein the peak is ascribed to the (111) crystal face diffraction of a Pd—Pb intermetallic compound. Further, by stabilizing the catalyst of the present invention in such a manner as mentioned above, the catalyst can be maintained at a state which is more preferable for the catalyst of the present invention, i.e., a state satisfying requirements such that the {(Pd3d(3/2)+Pd3d(5/2)}/ {Pb4f(7/2)×1.75) ratio of the sum of respective intensities of two peaks respectively ascribed to the 3d(3/2) electron and the 3d(5/2) electron of metallic palladium to the intensity of a peak ascribed to the 4f(7/2) electron of metallic lead which is multiplied by 1.75 is 1/0.2 to 1/0.7. Thus, the method for continuously producing the carboxylic ester by using a catalyst of the present invention can be carried out advantageously.

BEST MODE FOR CARRYING OUT THE INVENTION

The present invention will now be further illustrated in more detail with reference to the following Referential Examples, Comparative Referential Examples, Examples and Comparative Examples, which should not be construed as limiting the scope of the present invention.

In the following Referential Examples, Comparative Referential Examples, Examples and Comparative Examples, catalysts and catalyst intermediates were measured with respect to the Pd/Pb atomic ratio, the diffraction angle (2θ) in the powder X-ray diffraction pattern and the X-ray photoelectron spectrum. Also, carriers for catalysts (or catalyst intermediates) were evaluated with respect to the water resistance, and measured with respect to the specific surface area. The above measurements and evaluations were conducted by the following methods:

[Measurement of the Pd/Pb Atomic Ratio of a Catalyst]

The Pd/Pb atomic ratio of a catalyst was measured by inductively coupled plasma emission spectrometry (ICP), using JY-38P2 (manufactured and sold by Seiko Instruments Inc., Japan) as an ICP emission spectrometer.

[Measurement of the Diffraction Angle (2θ) for a Maximum Intensity Peak in the Powder X-ray Diffraction Pattern of a Catalyst, wherein the Peak is Ascribed to the (111) Crystal Face Diffraction of a Pd—Pb Intermetallic Compound]

The diffraction angle (2θ) for a maximum intensity peak in the powder X-ray diffraction pattern of the catalyst, wherein the peak is ascribed to the (111) crystal face diffraction of a Pd—Pb intermetallic compound, was determined as follows. The catalyst was subjected to heat-treatment at 160° C. for 3 hours under evacuation, thereby removing low molecular weight components (mainly hydrogen) adsorbed on and occluded in the catalyst. The heat-treated catalyst was subjected to powder X-ray diffraction using $CuK_{\alpha1}$ ray (1.5405981 Å) by a conventional method. RAD-RA (manufactured and sold by Rigaku Corporation, Japan) was used as an X-ray diffractometer. In the following Referential Examples, Examples and Comparative Examples, the "diffraction angle (2θ) for a maximum intensity peak in the powder X-ray diffraction pattern of the catalyst, wherein the peak is ascribed to the (111) crystal face diffraction of a Pd—Pb intermetallic compound," is frequently referred to simply as "diffraction angle (2θ) for a maximum intensity peak in the powder X-ray diffraction pattern", "diffraction angle (2θ) in the powder X-ray diffraction at which a maximum intensity peak was exhibited" or the like.

The above-mentioned measurement needs to be done with high precision. For example, using a $LaB_6$ compound, which is defined as a standard reference material 660 by the National Institute of Standards & Technology, U.S.A., standardization is conducted so that the diffraction angles (2θ) for maximum intensity peaks which are ascribed to the (111) crystal face diffraction and (200) crystal face diffraction of $LaB_6$ compound become 37.441° and 43.506°, respectively. By virtue of such standardization, a measurement of the diffraction angle (2θ) for a maximum intensity peak in the powder X-ray diffraction pattern can be conducted precisely, so that reproducible results can be obtained.

[Measurement of the X-ray Photoelectron Spectrum of a Catalyst]

Figure 2:
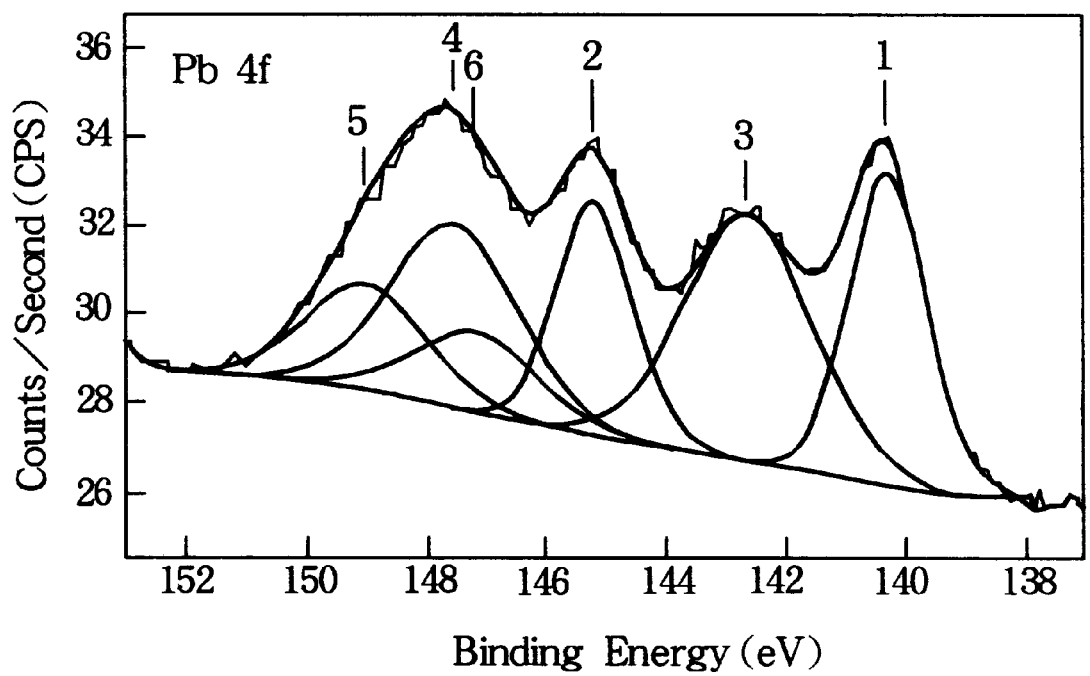
FIG. 2 shows spectra obtained from metallic lead by X-ray photoelectron spectroscopy, showing peaks ascribed to the Pb(4f) electrons of metallic lead, together with the results of the curve fitting the peaks and the resolution of overlapping peaks.

The measurement of the X-ray photoelectron spectrum of a catalyst is conducted using a photoelectric spectrophotometer LAB-200-X (manufactured and sold by Vacuum Generator Science, England). As shown in FIG. 1 and FIG. 2, with respect to the obtained spectrum, a curve fitting of peaks is effected and, in the case of the measurement for obtaining peaks ascribed to lead electrons (see FIG. 2), resolution of overlapping peaks is effected, to obtain peaks. Then, the areas defined by the respective peaks were determined, and the ratio of the total of the areas defined by two peaks ascribed to metallic palladium {(3d(3/2)+3d(5/2)} electrons to the area defined by a peak ascribed to metallic lead {4f(7/2)×1.75} electron was obtained. Also, the ratio of the total of the areas defined by two peaks ascribed to metallic palladium {3d(3/2)+3d(5/2)} electrons to the total of the areas defined by two peaks ascribed to ionic lead {4f(7/2)+4f(5/2)} electrons was obtained. The above-obtained area ratios are defined as the ratios of the intensities of the peaks (hereinafter, the ratio of the total intensity of two peaks ascribed to metallic palladium {(3d(3/2)+3d(5/2)} electrons to the intensity of a peak ascribed to metallic lead (4f(7/2)×1.75} electron and the ratio of the total intensity of two peaks ascribed to metallic palladium {3d(3/2)+3d(5/2)} electrons to the total intensity of two peaks ascribed to ionic lead {4f(7/2)+4f(5/2)} electrons are, respectively, referred ferred to simply as "the ratio of the total intensity of two peaks ascribed to metallic palladium 3d electrons to the intensity of a peak ascribed to metallic lead 4f(7/2) electron which is multiplied by 1.75" and "the ratio of the total intensity of two peaks ascribed to metallic palladium 3d electrons to the total intensity of two peaks ascribed to ionic lead 4f electrons"). A spectrum of palladium (3d) electrons and a spectrum of lead (4f) electrons are shown in FIG. 1 and FIG. 2, respectively.

[Evaluation of the Hydrolysis Resistance of the Carrier for a Catalyst]

The hydrolysis resistance (hereinbelow, referred to simply as "water resistance") of the carrier for a catalyst was evaluated in accordance with the following accelerated test: A concentration of Si ions measured as mentioned below was used as a criterion of water resistance of the carrier. 0.2 g of the carrier was weighed out and charged in a 100-ml stainless container. 20 g of water was added to the carrier to thereby obtain a mixture. The container was sealed and heated at 180° C. for 1 hour, to thereby effect hydrolysis of the carrier. Si ions are dissolved out from the catalyst into the water. The concentration of Si ions dissolved out in the water was measured by ICP emission spectrometry, using the above-mentioned ICP emission spectrometer.

[Measurement of the Specific Surface Area of the Carrier for a Catalyst]

The specific surface area of the carrier was measured by the BET nitrogen adsorption method.

Referential Example 1

Aluminum nitrate and magnesium nitrate were dissolved in an aqueous silica sol {Snowtex N-30 ($SiO_2$ content: 30% by weight), manufactured and sold by Nissan Chemical Industries, Ltd., Japan} so that the Al/(Si+Al) proportion became 10 mol % and the Mg/(Si+Mg) proportion became 10 mol %. The resultant solution was subjected to spray drying by means of a spray dryer at 130° C., thereby obtaining particles having an average particle diameter of 60 μm. The obtained particles were calcined in air at 300° C. for 2 hours and subsequently at 600° C. for 3 hours, thereby obtaining a carrier for a catalyst. To the obtained carrier were added an aqueous solution of palladium chloride (15% by weight) and sodium chloride (10% by weight) and an aqueous solution of lead nitrate (13% by weight) so that the amounts of the palladium chloride and lead nitrate contained in the resultant mixture became 5 parts by weight in terms of Pd and 6.5 parts by weight in terms of Pb, respectively, relative to 100 parts by weight of the carrier. The resultant mixture was stirred at room temperature for 1 hour, thereby obtaining a carrier adsorbing almost all amounts of the palladium chloride and lead nitrate thereon. Thereafter, to the obtained carrier adsorbing the palladium chloride and lead nitrate thereon was dropwise added, while stirring, an aqueous solution containing hydrazine in a molar amount which was 3 times as large as the total molar amount of the Pd and Pb adsorbed on the carrier, thereby reducing the palladium chloride and lead nitrate adsorbed on the carrier. Thus, a composition $Pd^{5.0}Pb^{6.5}/SiO_2—Al_2O_3—MgO$, wherein the superscript numerals at the right-hand of Pd and Pb, respectively, represent parts by weight of Pd and Pb, relative to 100 parts by weight of the carrier, was obtained (hereinafter, the obtained composition was frequently referred to simply as "catalyst intermediate"). The catalyst intermediate was analyzed with respect to the atomic ratio of palladium to lead (Pd/Pb atomic ratio), and to the diffraction angle (2θ) in the powder X-ray diffraction pattern thereof at which the maximum intensity peak was exhibited, by the methods as mentioned above. As a result, it was found that the catalyst intermediate had a Pd/Pb atomic ratio of 3/1.95, and exhibited a maximum intensity peak at a diffraction angle (2θ) of 38.745° in the powder X-ray diffraction pattern thereof and that the ratio of the total intensity of two peaks ascribed to metallic palladium 3d electrons to the intensity of a peak ascribed to metallic lead 4f(7/2) electrons which is multiplied by 1.75 in the X-ray photoelectron spectrum of the catalyst intermediate was 1/1.24.

EXAMPLE 1

A stainless, external circulation type bubble column reactor, which was equipped with a separator for a catalyst and has a volume of 1.2 liters for a liquid phase, was charged with 300 g of the catalyst intermediate prepared in Referential Example 1. Then, the charged catalyst intermediate was activated as follows. A 36.7% by weight solution of methacrolein in methanol and a 2 to 4% by weight solution of NaOH in methanol were continuously fed to the reactor at 0.54 liter/hr and at 0.06 liter/hr, respectively (the methacrolein concentration in the reaction system consisting of the above-mentioned two different solutions was about 33% by weight), while introducing air to the reactor so that the oxygen concentration at the outlet of the reactor became 3.0% by volume (which is equivalent to the oxygen partial pressure of 0.15 kg/cm$^2$), to effect an activation of the catalyst intermediate. The activation was conducted at a temperature of 80° C. under a pressure of 5 kg/cm$^2$ while conducting a reaction for producing MMA. The concentration of NaOH in the above-mentioned methanol solution of NaOH was controlled so that the reaction system had a pH of 7.1. The reaction mixture obtained by the above reaction was continuously withdrawn from the outlet of the reactor at a rate of 0.6 liter/hr. The activation of the catalyst intermediate was completed after 50 hours from the start of the reaction. During the reaction, the reaction mixture fractions continuously withdrawn from the outlet of the reactor contained about 270 ppm of lead on the average. It is assumed that the reason for this is that the lead contained in the catalyst is dissolved out in an ionized form thereof into the reaction system by the action of methacrylic acid produced during the above reaction (the reaction mixture fractions continuously withdrawn from the outlet of the reactor contained 1.1% by weight of methacrylic acid on the average), and the formed lead ions are reduced with active hydrogen which is generated in the reaction between methacrolein and methanol.

After completion of the activation, the resultant activated catalyst was analyzed with respect to the Pd/Pb atomic ratio and to the diffraction angle (2θ) in the powder X-ray diffraction pattern thereof at which a maximum intensity peak was exhibited, by the methods as mentioned above. As a result, it was found that the catalyst had a Pd/Pb atomic ratio of 3/1.24, and exhibited a maximum intensity peak at a diffraction angle (2θ) of 38.652° in the powder X-ray diffraction pattern thereof.

240 g of the above-obtained activated catalyst was charged in the bubble column reactor of the same type as mentioned above, and a reaction for producing methyl methacrylate (MMA) was carried out as follows. A 36.7% by weight solution of methacrolein in methanol and a 2 to 4% by weight solution of NaOH in methanol were continuously fed to the reactor at 0.54 liter/hr and at 0.06 liter/hr, respectively (the methacrolein concentration in the reaction system consisting of the above-mentioned two different solutions was about 33% by weight), while introducing air to the reactor so that the oxygen concentration at the outlet of the reactor became 4.0% by volume (which is equivalent to the oxygen partial pressure of 0.20 kg/cm$^2$), thereby effecting a reaction for producing MMA. The reaction was conducted at a temperature of 80° C. under a pressure of 5 kg/cm$^2$. The concentration of NaOH in the above-mentioned methanol solution of NaOH was controlled so that the reaction system had a pH of 7.1. The reaction mixture obtained by the above reaction was continuously withdrawn by overflowing from the outlet of the reactor. Analysis was made with respect to the reaction mixture which was withdrawn from the outlet of the reactor 10 hours after the start of the reaction. As a result, it was found that the conversion of methacrolein was 57.3%, the selectivity for MMA was 90.7%, and the selectivity for propylene as a by-product was 1.7%, and that methyl formate was by-produced in an amount of 0.085 mol/mol of MMA. It was also found that the productivity of MMA was 0.49 {MMA(g)/g of catalyst·hr}.

Comparative Example 1-1

A catalyst was prepared in substantially the same manner as described in Example 1 of Examined Japanese Patent Application Publication No. 62-7902. Illustratively stated, 176 g of magnesium acetate tetrahydrate and 92 g of lead acetate trihydrate were dissolved in 4,000 ml of water. To the resultant solution was added 1,000 g of a silica gel (Cariact 10, manufactured and sold by Fuji Silysia Chemical, Ltd., Japan), and the silica gel was impregnated with the aqueous solution of magnesium acetate tetrahydrate and lead acetate trihydrate on a boiling water bath with stirring, followed by drying. The dried substance was calcined at 500° C. for 3 hours, and the resultant substance was added to 10 liters of an aqueous diluted hydrochrolic acid solution containing 83 g of palladium chloride, which had been heated to 60° C., so that the substance was impregnated with the palladium chloride-containing aqueous diluted hydrochloric acid solution. Then, to the resultant substance were added 200 ml of a 35% by weight aqueous formaldehyde solution and 200 ml of an aqueous 1N sodium hydroxide solution. The resultant mixture was subjected to filtration to thereby obtain a filter cake, and the filter cake was washed and dried, thereby obtaining a composition Pd$^{5.0}$Pb$^{5.0}$/SiO$_2$ having a Pd/Pb atomic ratio of 3/1.54 (hereinafter, the obtained composition was frequently referred to simply as "catalyst intermediate"). {The thus obtained catalyst intermediate as such was subjected to X-ray diffraction as described in the above-mentioned Examined Japanese Patent Application Publication No. 62-7902. As a result, it was found that the catalyst intermediate exhibited a maximum intensity peak at a diffraction angle (2θ) of 38.631° in the powder X-ray diffraction pattern thereof, as described in the above-mentioned Examined Japanese Patent Application Publication.}

With respect to the above-obtained catalyst intermediate, a heat-treatment was conducted and then, an X-ray diffraction measurement was conducted according to the method specified above. That is, the above-obtained catalyst intermediate was heat-treated at 160° C. for 3 hours under evacuation, thereby removing low molecular weight components adsorbed on and occluded in the catalyst intermediate, and the heat-treated catalyst intermediate was subjected to X-ray diffraction. As a result, it was found that the heat-treated catalyst intermediate exhibited a maximum intensity peak at a diffraction angle (2θ) of 38.786° in the powder X-ray diffraction pattern thereof.

A stainless, external circulation type bubble column reactor, which was equipped with a separator for a catalyst and has a volume of 1.2 liters for a liquid phase, was charged with 240 g of the heat-treated catalyst intermediate. A reaction for producing MMA was carried out in substantially the same manner as in Example 1. Illustratively stated, a 36.7% by weight solution of methacrolein in methanol and a 2 to 4% by weight solution of NaOH in methanol were continuously fed at 0.54 liter/hr and at 0.06 liter/hr, respectively (the methacrolein concentration of the reaction system consisting of the above-mentioned two different solutions was about 33% by weight), while introducing air to the reactor so that the oxygen concentration at the outlet of the reactor became 4.0% by volume (which is equivalent to the oxygen partial pressure of 0.20 kg/cm$^2$), thereby effecting a reaction for producing MMA at a temperature of 80° C. under a pressure of 5 kg/cm$^2$. The concentration of NaOH in the above-mentioned methanol solution of the NaOH was controlled so that the reaction system had a pH of 7.1. The reaction mixture obtained by the above reaction was continuously withdrawn by overflowing from the outlet of the reactor. Analysis was made with respect to the reaction mixture which was withdrawn from the outlet of the reactor 10 hours after the start of the reaction. As a result, it was found that the conversion of methacrolein was 56.3%, the selectivity for MMA was 82.6%, and the selectivity for propylene as a by-product was 6.16%, and that methyl formate was by-produced in an amount of 0.163 mol/mol of MMA. It was also found that the productivity of MMA was 0.44 {MMA(g)/g of catalyst·hr}.

Comparative Example 1-2

Substantially the same procedure as in Comparative Example 1-1 was repeated, except that the reaction for producing MMA was conducted at a methacrolein concentration in the reaction system of 10% by weight, and at a reaction temperature of 40° C. 10 Hours after the start of the reaction, the reaction mixture withdrawn from the outlet of the reactor was analyzed. As a result, it was found that the conversion of methacrolein was 38.6%, the selectivity for MMA was 92.0%, and the selectivity for propylene as a by-product was 0.92%, and that methyl formate was by-produced in an amount of 0.038 mol/mol of MMA. It was also found that the productivity of MMA was 0.11 {MMA (g)/g of catalyst·hr}.

Comparative Example 2

Substantially the same procedure as in Example 1 was repeated, except that the reaction for producing MMA was conducted using the catalyst prepared in Referential Example 1 as such. 10 Hours after the start of the reaction, the reaction mixture withdrawn from the outlet of the reactor was analyzed. As a result, it was found that the conversion of methacrolein was 55.2%, the selectivity for MMA was 84.1%, and the selectivity for propylene as a by-product was 7.9%, and that methyl formate was by-produced in an amount of 0.242 mol/mol of MMA.

EXAMPLES 2 to 6, AND COMPARATIVE EXAMPLES 3-1, 3-2, 4-1, 4-2, 5 AND 6

In each of Examples 2 to 6 and Comparative Examples 3-1, 3-2, 4-1, 4-2, 5 and 6, substantially the same procedure as in Example 1 was repeated using a catalyst intermediate shown in Table 1 below. The catalyst intermediates used in Examples 2 to 6 had been individually subjected to activation treatment in substantially the same manner as in Example 1, whereas the catalyst intermediates used in Comparative Examples 3-1, 4-1, 5 and 6 had not been subjected to activation treatment. In Comparative Examples 3-2 and 4-2, substantially the same procedures as in Comparative Examples 3-1 and 4-1, respectively, were repeated, except that each of the reactions for producing MMA was conducted at a methacrolein concentration of the reaction system of 10% by weight, and at a reaction temperature of 50° C.

The composition of the catalyst intermediate, the Pd/Pb atomic ratio of each of the activated catalyst and catalyst intermediate, and the diffraction angle (2θ) for a maximum intensity peak in the powder X-ray diffraction pattern of each of the activated catalyst and catalyst intermediate in each of Examples 2 to 6, and Comparative Examples 3-1, 3-2, 4-1, 4-2, 5 and 6 are shown in Table 1, together with the respective results of the analyses of the reaction mixtures obtained 10 hours after the start of the MMA-producing reactions.

TABLE 1

| Examples and Comparative Examples (*3) | Composition of catalyst intermediate [catalyst active species (*1) carrier] | Activated catalyst (*4) | | Conversion of methacrolein (%) | Selectivity for MMA (%) | Selectivity for propylene (%) | Amount of methyl formate produced (mol/mol of MMA) |
|---|---|---|---|---|---|---|---|
| | | Pd/Pb atomic ratio | Diffraction angle (2θ) for maximum intensity peak | | | | |
| Example 2 | Pd$^{5.0}$Pb$^{3.08}$/SiO$_2$ | 3/0.95 | 38.621° | 55.8 | 89.7 | 2.34 | 0.025 |
| Example 3 | Pd$^{5.0}$Pb$^{3.28}$Mg$^{5.0}$/SiO$_2$ | 3/1.01 | 38.608° | 56.8 | 90.3 | 1.93 | 0.078 |
| Example 4 | Pd$^{5.0}$Pb$^{3.21}$K$^{2.0}$/Al$_2$O$_3$ | 3/0.99 | 38.595° | 66.9 | 90.9 | 1.12 | 0.124 |
| Example 5 | Pd$^{5.0}$Pb$^{3.89}$Tl$^{0.11}$/SiO$_2$—Al$_2$O$_3$ (*2) | 3/1.20 | 38.562° | 58.8 | 91.3 | 0.58 | 0.129 |
| Example 6 | Pd$^{5.0}$Pb$^{2.63}$Bi$^{0.25}$/SiO$_2$—Al$_2$O$_3$ (*2) | 3/0.81 | 38.649° | 57.3 | 89.9 | 2.57 | 0.026 |
| Comparative Example 3-1 | Pd$^{5.0}$Pb$^{4.95}$/SiO$_2$ | 3/1.52 | 38.753° | 56.9 | 82.5 | 6.32 | 0.15 |
| Comparative Example 3-2 | Pd$^{5.0}$Pb$^{4.95}$/SiO$_2$ | 3/1.52 | 38.753° | 63.2 | 91.5 | 1.21 | 0.042 |
| Comparative Example 4-1 | Pd$^{5.0}$Pb$^{9.67}$/Al$_2$O$_3$ | 3/2.98 | 38.673° | 54.1 | 86.4 | 2.85 | 0.92 |
| Comparative Example 4-2 | Pd$^{5.0}$Pb$^{9.67}$/Al$_2$O$_3$ | 3/2.98 | 38.673° | 58.3 | 92.7 | 0.65 | 0.10 |

TABLE 1-continued

| Examples and Comparative Examples (*3) | Composition of catalyst intermediate [catalyst active species (*1) carrier] | Activated catalyst (*4) | | Conversion of methacrolein (%) | Selectivity for MMA (%) | Selectivity for propylene (%) | Amount of methyl formate produced (mol/mol of MMA) |
|---|---|---|---|---|---|---|---|
| | | Pd/Pb atomic ratio | Diffraction angle (2θ) for maximum intensity peak | | | | |
| Comparative Example 5 | Pd$^{5.0}$Pb$^{1.69}$Mg$^{5.0}$/Al$_2$O$_3$ | 3/0.52 | 38.912° | 58.3 | 78.2 | 12.8 | 0.056 |
| Comparative Example 6 | Pd$^{5.0}$Pb$^{3.51}$/Al$_2$O$_3$ | 3/1.08 | 38.790° | 62.3 | 86.8 | 4.72 | 0.052 |

Note:
*1) The superscript numerals indicated at the right-hand of the elements of each of the catalyst active species of the respective catalyst intermediates represent parts by weight, relative to 100 parts by weight of the carrier.
*2) In the carrier SiO$_2$—Al$_2$O$_3$, the Al/(Al + Si) proportion is 30 mol %.
*3) In each of Examples 2 to 6 and Comparative Examples 3-1, 4-1, 5 and 6, the reaction for producing MMA was conducted at a methacrolein concentration of the reaction system of about 33% by weight and at a temperature of 80° C. In each of Comparative Examples 3-2 and 4-2, the reaction was conducted at a methacrolein concentration of the reaction system of 10% by weight and at a temperature of 50° C.
*4) In each of the Comparative Examples, the data of the Pd/Pb atomic ratio and the diffraction angle (2θ) for maximum intensity peak are those which are obtained with respect to the catalyst intermediate.

Referential Example 2

176 g of magnesium acetate tetrahydrate was dissolved in 1000 ml of water, and to the resultant aqueous magnesium acetate solution was added 1000 g of a silica gel (Cariact 10, manufactured and sold by Fuji Silysia Chemical, Ltd., Japan), followed by stirring on a boiling water bath to thereby impregnate the silica gel with the aqueous magnesium acetate solution. The resultant impregnated substance was evaporated and dried. The dried substance was calcined at 500° C. for 3 hours to thereby obtain a carrier. The obtained carrier was mixed with an aqueous solution obtained by dissolving 83 g of palladium chloride and 28 g of sodium chloride in 500 ml of water, and an aqueous solution obtained by dissolving 52.1 g of lead nitrate in 500 ml of water. To the resultant mixture was added water so that the total volume became 10 liters, and the resultant mixture was allowed to stand for 1 hour to thereby adsorb palladium chloride and lead nitrate on the carrier. Then, a supernatent was removed and decantation was conducted several times, and to the resultant residue was added water so that the total volume of the resultant mixture became 10 liters. An aqueous 10% by weight solution of hydrazine was added to the above-obtained mixture in an amount such that the molar amount of hydrazine was 3 times as large as the total molar amount of palladium and lead, thereby reducing the palladium adsorbed on the carrier, followed by washing with water until no chlorine ions were detected in the washings. Thus, a composition containing the carrier having adsorbed thereon 5.0 parts by weight of palladium and 3.18 parts by weight of lead, relative to 100 parts by weight of the carrier was obtained (hereinafter, the obtained composition was frequently referred to simply as "catalyst intermediate"). The obtained catalyst intermediate was analyzed with respect to the Pd/Pb atomic ratio, the diffraction angle (2θ) in the powder X-ray diffraction pattern thereof at which a maximum intensity peak was exhibited and the ratio of the total intensity of two peaks ascribed to metallic palladium 3d electrons to the intensity of a peak ascribed to metallic lead 4f(7/2) electron which is multiplied by 1.75 in the X-ray photoelectron spectrum thereof, by the methods as mentioned above. As a result, it was found that the catalyst had a Pd/Pb atomic ratio of 3/0.98 and exhibited a maximum intensity peak at a diffraction angle (2θ) of 38.927°, and that the ratio of the total intensity of two peaks ascribed to metallic palladium 3d electrons to the intensity of a peak ascribed to metallic lead 4f(7/2) electron which was multiplied by 1.75 was 1/0.15.

EXAMPLE 7

An agitation type reactor, which had a volume of 6 liters for a liquid phase, was charged with 1 kg of the catalyst intermediate prepared in Referential Example 2, and 5 liters of a solution of 20.9 g of lead acetate trihydrate in methanol, in which the amount of lead acetate corresponds to a supplementary lead amount necessary for changing the Pd/Pb atomic ratio (3/0.98) of the catalyst intermediate prepared in Referential Example 2 to 3/1.3. The charged catalyst intermediate was subjected to activation treatment at a temperature of 90° C. under a pressure of 5 kg/cm$^2$ for 20 hours, while introducing air to the reactor so that the oxygen concentration at the outlet of the reactor became 2.0% by volume (which is equivalent to the oxygen partial pressure of 0.10 kg/cm$^2$). The resultant activated catalyst was analyzed with respect to the Pd/Pb atomic ratio and the diffraction angle (2θ) in the powder X-ray diffraction pattern thereof at which the maximum intensity peak was exhibited, by the methods as mentioned above. As a result, it was found that the catalyst had a Pd/Pb atomic ratio of 3/1.27, and exhibited a maximum intensity peak at a diffraction angle (2θ) of 38.691° in the powder X-ray diffraction pattern thereof.

200 g of the above-obtained catalyst was charged in an agitation type reactor having the same volume for a liquid phase as that of the external circulation type bubble column reactor used in Example 1, and a reaction for producing MMA was carried out as follows. A 36.7% by weight solution of methacrolein in methanol and a 2 to 4% by weight solution of NaOH in methanol was continuously fed to the reactor at 0.54 liter/hr and at 0.06 liter/hr, respectively (the methacrolein concentration of the reaction system consisting of the above-mentioned two different solutions was about 33% by weight), while introducing air to the reactor so that the oxygen concentration at the outlet of the reactor became 4.0% by volume (which is equivalent to the oxygen partial pressure of 0.20 kg/cm$^2$), thereby effecting a reaction for producing MMA. The reaction was conducted at a temperature of 80° C. under pressure of 5 kg/cm$^2$. The concentration of NaOH in the above-mentioned methanol solution of NaOH was controlled so that the reaction system had a pH of 7.1. The reaction mixture obtained by the above reaction was continuously withdrawn by overflowing from the outlet of the reactor. Analysis was made with respect to the reaction mixture which was withdrawn from the outlet of the reactor 10 hours after the start of the reaction. As a result, it was found that the conversion of methacrolein was 57.8%, the selectivity for MMA was 89.9%, and the selectivity for propylene as a by-product was 2.12%, and that methyl formate was by-produced in an amount of 0.103 mol/mol of MMA.

Comparative Example 7

Substantially the same procedure as in Example 7 was repeated, except that the reaction for producing MMA was conducted using the catalyst prepared in Referential Example 2 as such. 10 Hours after the start of the reaction, the reaction mixture withdrawn from the outlet of the reactor was analyzed. As a result, it was found that the conversion of methacrolein was 63.2%, the selectivity for MMA was 84.1%, and the selectivity for propylene as a by-product was 7.9%, and that methyl formate was by-produced in an amount of 0.092 mol/mol of MMA.

EXAMPLE 8

An agitation type reactor was charged with 1 kg of the catalyst intermediate prepared in Referential Example 2 and 5 liters of an aqueous solution of 20.9 g of lead acetate trihydrate, in which the amount of lead acetate corresponds to a supplementary lead amount necessary for changing the Pd/Pb atomic ratio (3/0.98) of the catalyst intermediate prepared in Referential Example 2 to 3/1.3. The resultant mixture was heated to 90° C., and to the thus heated mixture was added an aqueous formaldehyde (formaldehyde content: 37% by weight) so that the molar ratio of the formaldehyde to the palladium of the catalyst intermediate became 10/1. The resultant mixture was stirred at 90° C. for 1 hour, to thereby effect an activation of the catalyst intermediate. The activated catalyst was analyzed by the methods as mentioned above. As a result, it was found that the catalyst had a Pd/Pb atomic ratio of 3/1.27, and exhibited a maximum intensity peak at a diffraction angle ($2\theta$) of 38.642° in the powder X-ray diffraction pattern thereof.

Two stainless, external circulation type bubble column reactors as used in Example 1, each of which was equipped with a separator for a catalyst and had a volume of 1.2 liters for a liquid phase, were connected to provide a first stage reactor and a second stage reactor which were connected in series. Each of the first stage reactor and the second stage reactor was charged with 240 g of the above-obtained catalyst, and a series of reactions for the production of MMA was conducted as follows. A 36.7% by weight solution of methacrolein in methanol and a 2 to 4% by weight solution of NaOH in methanol were continuously fed to the first stage reactor at 0.54 liter/hr and at 0.06 liter/hr, respectively (the methacrolein concentration of the reaction system consisting of the above-mentioned two different solutions was about 33% by weight), while introducing air to the first stage reactor so the oxygen concentration at the outlet of the first stage reactor became 4.0% by volume (which is equivalent to the oxygen partial pressure of 0.20 kg/cm$^2$), to effect a reaction for producing MMA. The reaction was conducted at a temperature of 80° C. under a pressure of 5 kg/cm$^2$. The resultant reaction mixture containing the catalyst was continuously withdrawn by overflowing from the outlet of the first stage reactor and transferred to a liquid phase-solid phase separation zone, where a separation between the catalyst and the reaction mixture was effected. The separated catalyst was returned to the first stage reactor. The separated reaction mixture and a 2 to 4% by weight solution of NaOH in methanol was fed to the second stage reactor at 0.6 liter/hr and 0.06 liter/hr, respectively. A gaseous phase withdrawn from the first stage reactor was fed to the second stage reactor while introducing fresh air to the second stage reactor so that the oxygen concentration at the outlet of the second stage reactor became 2.2% by volume (which is equivalent to the oxygen partial pressure of 0.11 kg/cm$^2$) to effect a reaction for producing MMA. The reaction was conducted at a temperature of 80° C. under a pressure of 5 kg/cm$^2$. The concentration of NaOH in the methanol solution fed to each of the first stage and second stage reactors was controlled so that the reaction system in each reactor had a pH of 7.1. The reaction mixture obtained in the second stage reactor was continuously withdrawn by overflowing from the outlet of the second stage reactor. Analysis was made with respect to the reaction mixture which was withdrawn from the outlet of the second stage reactor 10 hours after the start of the reaction. As a result, it was found that the conversion of methacrolein was 80.2%, the selectivity for MMA was 91.1%, and the selectivity for propylene as a by-product was 1.2%, and that methyl formate was by-produced in an amount of 0.114 mol/mol of MMA.

EXAMPLE 9

Substantially the same procedure as in Example 7 was repeated, except that the activated catalyst prepared in Example 3 was used, and that acrolein was used instead of the methacrolein, to thereby effect a reaction for producing methyl acrylate. Analysis was made with respect to the reaction mixture which was withdrawn from the outlet of the reactor 10 hours after the start of the reaction. As a result, it was found that the conversion of acrolein was 58.2%, the selectivity for MA was 91.3%, and the selectivity for ethylene as a by-product was 1.2%, and that methyl formate was by-produced in an amount of 0.055 mol/mol of MA.

EXAMPLE 10

Substantially the same procedure as in Example 7 was repeated, except that the activated catalyst prepared in Example 4 was used, that benzaldehyde was used instead of the methacrolein, and that ethanol was used instead of the methanol, to thereby effect a reaction for producing methyl benzoate. Analysis was made with respect to the reaction mixture which was withdrawn from the outlet of the reactor 10 hours after the start of the reaction. As a result, it was found that the conversion of benzaldehyde was 76.2%, and the selectivity for methyl benzoate was 93.2%.

EXAMPLE 11

A stainless, external circulation type bubble column reactor, which was equipped with a separator for a catalyst and had a volume of 1.2 liters for a liquid phase, was charged with 300 g of the catalyst intermediate prepared in Referential Example 1. A 36.7% by weight solution of methacrolein in methanol and a 2 to 4% by weight solution of NaOH in methanol were continuously fed to the reactor at 0.54 liter/hr and at 0.06 liter/hr, respectively (the methacrolein concentration of the reaction system consisting of the above mentioned two different solutions was about 33% by weight), while introducing fresh air to the reactor so that the oxygen concentration at the outlet of the reactor became 3.0% by volume (which is equivalent to the oxygen partial pressure of 0.15 kg/cm$^2$), to effect an activation of the catalyst. The activation of the catalyst intermediate was conducted at a temperature of 80° C. under a pressure of 5 kg/cm². The above reaction was continued for 50 hours.

Subsequently, the oxygen concentration at the outlet of the reactor was changed to 4.0% by volume (which is equivalent to the oxygen partial pressure of 0.20 kg/cm²), and lead acetate was added to a 36.7% by weight solution of methacrolein in methanol to be fed to the reactor, so that the lead concentration of the reaction system became 20 ppm, to thereby effect a surface structure-controlling treatment of the activated catalyst. Analysis was made with respect to the reaction mixture which was withdrawn from the outlet of the reactor 100 hours after the start of the activation treatment, with respect to the Pd/Pb atomic ratio and the diffraction angle (2θ) for a maximum intensity peak in the powder X-ray diffraction pattern thereof, and the ratio of the total intensity of two peaks ascribed to metallic palladium 3d electrons to the intensity of a peak ascribed to metallic lead 4f(7/2) electron which is multiplied by 1.75 in the X-ray photoelectron spectrum thereof, by the methods as mentioned above. As a result, it was found that the catalyst had a Pd/Pb atomic ratio of 3/1.08 and exhibited the maximum intensity peak at a diffraction angle (2θ) of 38.612°, and that the ratio of the total intensity of two peaks ascribed to metallic palladium 3d electrons to the intensity of a peak ascribed to metallic lead 4f(7/2) electron which is multiplied by 1.75 was 1/0.49.

A stainless, external circulation type bubble column reactor, which was equipped with a separator for a catalyst and had a volume of 1.2 liters for a liquid phase, was charged with 240 g of the catalyst obtained by the above-mentioned surface structure-controlling treatment, and a reaction for the production of MMA was performed as follows. A 36.7% by weight solution of methacrolein in methanol and a 2 to 4% by weight solution of NaOH in methanol were continuously fed to the reactor at 0.54 liter/hr and at 0.06 liter/hr, respectively (the methacrolein concentration of the reaction system consisting of the above mentioned two different solutions was about 33% by weight), while introducing air to the reactor so that the oxygen concentration at the outlet of the reactor became 4.0% by volume (which is equivalent to the oxygen partial pressure of 0.20 kg/cm²), thereby effecting a reaction for producing MMA. The reaction was conducted at a temperature of 80° C. under a pressure of 5 kg/cm². The concentration of NaOH in the above-mentioned methanol solution of NaOH was controlled so that the reaction system had a pH of 7.1. The reaction mixture was continuously withdrawn by overflowing from the outlet of the reactor. Analysis was made with respect to the reaction mixture which was withdrawn from the outlet of the reactor 10 hours after the start of the reaction. As a result, it was found that the conversion of methacrolein was 61.8%, the selectivity for MMA was 91.6%, and the selectivity for propylene as a by-product was 1.23%, and that methyl formate was by-produced in an amount of 0.045 mol/mol of MMA.

EXAMPLE 12

Substantially the same procedure for the activation treatment of a catalyst intermediate as in Example 11 was repeated, to thereby obtain an activated catalyst. The obtained activated catalyst was analyzed with respect to the Pd/Pb atomic ratio, the diffraction angle (2θ) for a maximum intensity peak in the powder X-ray diffraction pattern thereof, and the ratio of the total intensity of two peaks ascribed to metallic palladium 3d electrons to the intensity of a peak ascribed to metallic lead 4f(7/2) electron which is multiplied by 1.75 in the X-ray photoelectron spectrum thereof, by the methods as mentioned above. As a result, it was found that the catalyst had a Pd/Pb atomic ratio of 3/1.24 and exhibited the maximum intensity peak at a diffraction angle (2θ) of 38.652°, and that the ratio of the total intensity of two peaks ascribed to metallic palladium 3d electrons to the intensity of a peak ascribed to metallic lead 4f(7/2) electron which is multiplied by 1.75 was 1/0.89 thereof.

Using the activated catalyst, substantially the same procedure for producing MMA as in Example 1 was repeated, and analysis was made with respect to the reaction mixture which was withdrawn from the outlet of the reactor 10 hours after the start of the reaction. As a result, it was found that the conversion of methacrolein was 57.3%, the selectivity for MMA was 90.7%, and the selectivity for propylene as a by-product was 1.72%, and that methyl formate was by-produced in an amount of 0.085 mol/mol of MMA.

EXAMPLES 13 to 19 AND COMPARATIVE EXAMPLES 8 to 10

In each of Examples 13 to 19 and Comparative Examples 8 to 10, substantially the same procedure as in Example 11 was repeated using a catalyst intermediate shown in Table 2 below. The catalyst intermediates used in Examples 13 to 19 had been individually subjected to activation treatment and surface structure-controlling treatment in substantially the same manner as in Example 11, whereas the catalyst intermediates used in Comparative Examples 8 to 10 had not been subjected to an activation treatment or surface structure-controlling treatment. The composition of the catalyst intermediate, the Pd/Pb atomic ratio of each of the activated catalyst and catalyst intermediate, the diffraction angle (2θ) for a maximum intensity peak in the powder X-ray diffraction pattern of each of the activated catalyst and catalyst intermediate, and the ratio of the total intensity of two peaks ascribed to metallic palladium 3d electrons to the intensity of a peak ascribed to metallic lead 4f(7/2) electron which is multiplied by 1.75 in the X-ray photoelectron spectrum of each of the activated catalyst and catalyst intermediate in each of Examples 13 to 19 and Comparative Examples 8 to 10 are shown in Table 2, together with the respective results of the analyses of the reaction mixtures obtained 10 hours after the start of the MMA-producing reactions.

TABLE 2

| Examples and Comparative Examples | Composition of catalyst intermediate [catalyst active species (*1)/carrier] | Pd/Pb atomic ratio | Diffraction angle (2θ) for maximum intensity peak | Intensity ratio of peaks (metallic Pd/metallic Pb)*4 | Conversion of methacrolein (%) | Selectivity for MMA (%) | Selectivity for propylene (%) | Amount of methyl formate produced (mol/mol of MMA) |
|---|---|---|---|---|---|---|---|---|
| | | | Activated catalyst (*3) | | | | | |
| Example 13 | $Pd^{5.0}Pb^{3.21}/SiO_2$ | 3/0.99 | 38.602° | 1/0.21 | 62.7 | 89.8 | 2.13 | 0.038 |
| Example 14 | $Pd^{5.0}Pb^{3.41}Mg^{5.0}/SiO_2$ | 3/1.05 | 38.611° | 1/0.43 | 63.8 | 91.1 | 1.21 | 0.043 |
| Example 15 | $Pd^{5.0}Pb^{3.28}K^{2.0}/Al_2O_3$ | 3/1.01 | 38.598° | 1/0.65 | 71.7 | 91.5 | 1.11 | 0.073 |
| Example 16 | $Pd^{5.0}Pb^{3.99}Tl^{0.13}/SiO_2$—$Al_2O_3$ (*2) | 3/1.23 | 38.583° | 1/0.61 | 64.3 | 91.6 | 0.62 | 0.089 |
| Example 17 | $Pd^{5.0}Pb^{2.56}Bi^{0.23}/SiO_2$—$Al_2O_3$ (*2) | 3/0.79 | 38.656° | 1/0.38 | 63.9 | 90.0 | 2.38 | 0.031 |
| Comparative Example 8 | $Pd^{5.0}Pb^{6.91}/Al_2O_3$ | 3/2.13 | 38.753° | 1/0.64 | 56.9 | 85.3 | 6.32 | 0.15 |
| Comparative Example 9 | $Pd^{5.0}Pb^{1.69}Mg^{5.0}/Al_2O_3$ | 3/0.52 | 38.912° | 1/0.32 | 58.3 | 78.2 | 12.8 | 0.056 |
| Comparative Example 10 | $Pd^{5.0}Pb^{3.51}/Al_2O_3$ | 3/1.08 | 38.790° | 1/0.53 | 62.3 | 86.8 | 4.72 | 0.052 |
| Example 18 | $Pd^{5.0}Pb^{3.60}/Al_2O_3$ | 3/1.11 | 38.603° | 1/0.12 | 54.2 | 89.8 | 2.37 | 0.028 |
| Example 19 | $Pd^{5.0}Pb^{3.18}/Al_2O_3$ | 3/0.98 | 38.587° | 1/1.32 | 52.1 | 90.7 | 0.05 | 0.45 |

Note:
*1) The superscript numerals indicated at the right-hand of the elements of each of the catalyst active species of the respective catalyst intermediates represent parts by weight, relative to 100 parts by weight of the carrier.
*2) In the carrier $SiO_2$—$Al_2O_3$, the Al/(Al + Si) proportion is 30 mol %.
*3) In each of the Comparative Examples, the data of the Pd/Pb atomic ratio and the diffraction angle (2θ) for maximum intensity peak are those which are obtained with respect to the catalyst intermediate.
*4) Ratio of the total intensity of two peaks ascribed to metallic palladium 3d electrons to the intensity of a peak ascribed to metallic lead 4f (7/2) electron which is multiplied by 1.75 in the X-ray photoelectron spectrum.

EXAMPLE 20

Two stainless, external circulation type bubble column reactors, each of which was equipped with a separator for a catalyst and had a volume of 1.2 liters for a liquid phase, were connected to provide a first stage reactor and a second stage reactor which were connected in series. Each of the first stage and second stage reactors was charged with 240 g of a catalyst which had been obtained by subjecting the catalyst intermediate prepared in Referential Example 1 to an activation treatment and subsequently subjecting the activated catalyst to a surface structure-controlling treatment in the same manner as in Example 11. Then, a series of reactions for producing MMA was conducted as follows. A 36.7% by weight solution of methacrolein in methanol, in which lead acetate had been dissolved so that the lead concentration of the resultant reaction system became 20 ppm by weight, and a 2 to 4% by weight solution of NaOH in methanol were continuously fed to the first stage reactor at 0.54 liter/hr and at 0.06 liter/hr, respectively (the methacrolein concentration of the reaction system consisting of the above-mentioned two different solutions was about 33% by weight), while introducing air to the first stage reactor so that the oxygen concentration at the outlet of the first stage reactor became 4.0% by volume (which is equivalent to the oxygen partial pressure of 0.20 kg/cm²), to effect a reaction for producing MMA. The reaction was conducted at a temperature of 80° C. under a pressure of 5 kg/cm². The resultant reaction mixture containing the catalyst was continuously withdrawn by overflowing from the outlet of the first stage reactor and transferred to a liquid phase-solid phase separation zone, where a separation between the catalyst and the reaction mixture was effected. The separated catalyst was returned to the first stage reactor. The separated reaction mixture and a 2 to 4% by weight solution of NaOH in methanol were fed to the second stage reactor at 0.6 liter/hr and at 0.06 liter/hr, respectively. A gaseous phase withdrawn from the first stage reactor was fed to the second stage reactor while introducing fresh air to the second stage reactor so that the oxygen concentration at the outlet of the second stage reactor became 2.2% by volume (which is equivalent to the oxygen partial pressure of 0.11 kg/cm²), to effect a reaction for producing MMA. The reaction was conducted at a temperature of 80° C. under a pressure of 4.6 kg/cm². The concentration of NaOH in the methanol solution fed to each of the first stage and second stage reactors was controlled so that the reaction system in each reactor had a pH of 7.1. The reaction mixture obtained in the second stage reactor was continuously withdrawn by overflowing from the outlet of the second stage reactor. Analysis was made with respect to the reaction mixture which was withdrawn from the outlet of the second stage reactor 500 hours after the start of the two-stage reaction. As a result, it was found that the conversion of methacrolein was 81.6%, the selectivity for MMA was 91.5%, and the selectivity for propylene as a by-product was 1.36%, and that methyl formate was by-produced in an amount of 0.049 mol/mol of MMA. Also, a portion of each of the catalysts contained in the first stage reactor and the second stage reactor was taken out from the respective reactors, and analyzed with respect to the Pd/Pb atomic ratio thereof, the diffraction angle (2θ) in the powder X-ray diffraction pattern thereof at which a maximum intensity peak was exhibited, and the ratio of the total intensity of two peaks ascribed to metallic palladium 3d electrons to the intensity of a peak ascribed to metallic lead 4f(7/2) electron which is multiplied by 1.75 in the X-ray photoelectron spectrum thereof, by the methods as mentioned above. As a result, it was found that the catalyst taken out from the first stage reactor had a Pd/Pb atomic ratio of 3/1.05 and exhibited a maximum intensity peak at a diffraction angle (2θ) of 38.602°, and that the ratio of the total intensity of two peaks ascribed to metallic palladium 3d electrons to the intensity of a peak ascribed to metallic lead 4f(7/2) electron which is multiplied by 1.75 was 1/0.45. It was also found that the catalyst taken out from the second stage reactor had a Pd/Pb atomic ratio of 3/0.98 and exhibited a maximum intensity peak at a diffraction angle (2θ) of 38.612°, and that the ratio of the total intensity of two peaks ascribed to metallic palladium 3d electrons to the intensity of a peak ascribed to metallic lead 4f(7/2) electron which is multiplied by 1.75 was 1/0.45.

Thereafter, the two-stage reaction for producing MMA was further conducted for 500 hours under the same reaction conditions as described above (That is, the reaction for producing MMA was conducted for 1000 hours in total). After that period of time, analyses were made with respect to the reaction mixture withdrawn from the outlet of the second stage reactor and to the catalyst contained in each of the first stage and second stage reactors, and the results of the analyses were compared with the results of the analyses of the reaction mixture and the catalysts, which were obtained 500 hours after the start of the two-stage reaction. As a result, it was found that no significant change was observed with respect to the results of the MMA-producing reaction, except that the amount of the by-produced methyl formate was reduced to 0.039 mol/mol of MMA. Also, there was no significant change in the catalyst contained in each of the first stage and second stage reactors by the further 500-hour reaction, with respect to the Pd/Pb atomic ratio, the diffraction angle (2θ) for a maximum intensity peak in the powder X-ray diffraction pattern, and the ratio of the total intensity of two peaks ascribed to metallic palladium 3d electrons to the intensity of a peak ascribed to metallic lead 4f(7/2) electron which is multiplied by 1.75 in the X-ray photoelectron spectrum.

EXAMPLE 21

An agitation type reactor, which had a volume of 6 liters for a liquid phase, was charged with 1 kg of the catalyst intermediate prepared in Referential Example 2, and 5 liters of a solution of 20.9 g of lead acetate trihydrate in methanol, in which the amount of lead acetate corresponds to a supplementary lead amount necessary for changing the Pd/Pb atomic ratio (3/0.98) of the catalyst intermediate prepared in Referential Example 2 to 3/1.3. An activation of the catalyst intermediate was effected at a temperature of 90° C. under a pressure of 5 kg/cm$^2$ for 20 hours, while introducing air to the reactor so that the oxygen concentration at the outlet of the reactor became 2.0% by volume (which is equivalent to the oxygen partial pressure of 0.10 kg/cm$^2$). 200 g of the resultant activated catalyst was charged in an agitation type reactor having the same volume for a liquid phase as that of the reactor used in Example 11, and a reaction for controlling the surface structure of the activated catalyst was carried out as follows. A 36.7% by weight solution of methacrolein in methanol, in which lead acetate had been dissolved so that the lead concentration of the resultant reaction system became 20 ppm by weight, and a 2 to 4% by weight solution of NaOH in methanol were fed to the reactor at 0.54 liter/hr and 0.06 liter/hr, respectively (the methacrolein concentration of the reaction system consisting of the above-mentioned two different solutions was about 33% by weight), while introducing air to the reactor so that the oxygen concentration at the outlet of the reactor became 4.0% by volume (which is equivalent to the oxygen partial pressure of 0.20 kg/cm$^2$), thereby effecting a reaction for controlling the surface structure of the catalyst. The reaction was conducted at a temperature of 80° C. under a pressure of 5 kg/cm$^2$. The concentration of NaOH was controlled so that the reaction system had a pH of 7.1. The reaction mixture obtained by the above reaction was continuously withdrawn by overflowing from the outlet of the reactor. The reaction for controlling the surface structure of the catalyst was conducted for 50 hours. After that period of time, analysis was made with respect to a portion of the catalyst taken out from the outlet of the reactor. As a result, it was found that the catalyst had a Pd/Pb atomic ratio of 3/1.10 and exhibited a maximum intensity peak at a diffraction angle (2θ) of 38.611° in the powder X-ray diffraction pattern thereof, and that the ratio of the total intensity of two peaks ascribed to metallic palladium 3d electrons to the intensity of a peak ascribed to metallic lead 4f(7/2) electron which is multiplied by 1.75 in the X-ray photoelectron spectrum was 1/0.428. The reaction for controlling the surface structure of the catalyst was further conducted for 10 hours under the same conditions as described above. After that period of time, analysis was made with respect to the reaction mixture withdrawn from the outlet of the reactor. As a result, it was found that the conversion of methacrolein was 63.2%, the selectivity for MMA was 91.3%, and the selectivity for propylene as a by-product was 1.1%, and that methyl formate was by-produced in an amount of 0.052 mol/mol of MMA.

EXAMPLE 22

The catalyst intermediate prepared in Referential Example 2 was subjected to activation treatment in substantially the same manner as in Example 21. The resultant activated catalyst was analyzed by the methods as mentioned above. As a result, it was found that the catalyst had a Pd/Pb atomic ratio of 3/1.27 and exhibited a maximum intensity peak at a diffraction angle (2θ) of 38.691° in the powder X-ray diffraction pattern thereof, and that the ratio of the total intensity of two peaks ascribed to metallic palladium 3d electrons to a peak ascribed to metallic lead 4f(7/2) electron which is multiplied by 1.75 in the X-ray photoelectron spectrum was 1/0.763. 200 g of the activated catalyst was charged in an agitation type reactor having the same volume for a liquid phase as that of the bubble column reactor used in Example 1. A 36.7% by weight solution of methacrolein in methanol, in which lead acetate had been dissolved so that the lead concentration of the resultant reaction system became 20 ppm by weight, and a 2 to 4% by weight solution of NaOH in methanol were fed to the reactor at 0.54 liter/hr and 0.06 liter/hr, respectively (the methacrolein concentration of the reaction system consisting of the above-mentioned two different solutions was about 33% by weight), while introducing air to the reactor so that the oxygen concentration at the outlet of the reactor became 4.0% by volume (which is equivalent to the oxygen partial pressure of 0.20 kg/cm$^2$), thereby effecting a reaction for producing MMA. The reaction was conducted at a temperature of 80° C. under a pressure of 5 kg/cm$^2$. The concentration of NaOH was controlled so that the reaction system had a pH of 7.1. The reaction mixture obtained by the above reaction was continuously withdrawn by overflowing from the outlet of the reactor. 10 Hours after the start of the reaction, analysis was made with respect to the reaction mixture withdrawn from the outlet of the reactor. As a result, it was found that the conversion of methacrolein was 57.2%, the selectivity for MMA was 89.3%, and the selectivity for propylene as a by-product was 2.03%, and that methyl formate was by-produced in an amount of 0.152 mol/mol of MMA.

EXAMPLE 23

An agitation type reactor, which had a volume of 6 liters for a liquid phase, was charged with 1 kg of the catalyst intermediate prepared in Referential Example 2, and 5 liters of an aqueous solution of 20.9 g of lead acetate trihydrate, in which the amount of lead acetate corresponds to a supplementary lead amount necessary for changing the Pd/Pb atomic ratio (3/0.98) of the catalyst intermediate prepared in Referential Example 2 to 3/1.3. The resultant mixture was heated to 90° C. To the heated mixture was added an aqueous 3% by weight solution of formaldehyde in an amount such that the molar ratio of the formaldehyde to the palladium of the catalyst intermediate became 10/1. The resultant mixture was stirred for 1 hour while maintaining the temperature of the mixture at 90° C., to thereby effect an activation of the catalyst intermediate. The resultant activated catalyst was analyzed by the methods as mentioned above. As a result, it was found that the catalyst had a Pd/Pb atomic ratio of 3/1.27 and exhibited a maximum intensity peak at a diffraction angle (2θ) of 38.642° in the powder X-ray diffraction pattern thereof, and that the ratio of the total intensity of two peaks ascribed to metallic palladium 3d electrons to the intensity of a peak ascribed to metallic lead 4f(7/2) electron which is multiplied by 1.75 in the X-ray photoelectron spectrum was 1/0.953.

240 g of the activated catalyst was charged in a stainless, external circulation type bubble column reactor, which was equipped with a separator for a catalyst and had a volume of 1.2 liters for a liquid phase. Then, a 36.7% by weight solution of methacrolein in methanol, in which lead acetate had been dissolved so that the lead concentration of the resultant reaction system became 20 ppm by weight, and a 2 to 4% by weight solution of NaOH in methanol were fed to the reactor at 0.54 liter/hr and 0.06 liter/hr, respectively (the methacrolein concentration of the reaction system consisting of the above-mentioned two different solutions was about 33% by weight), while introducing air to the reactor so that the oxygen concentration at the outlet of the reactor became 4.0% by volume (which is equivalent to the oxygen partial pressure of 0.20 kg/cm$^2$), thereby effecting a reaction for producing MMA. The reaction was conducted at a temperature of 80° C. under a pressure of 5 kg/cm$^2$. The concentration of NaOH was controlled so that the reaction system had a pH of 7.1. The reaction mixture obtained by the above reaction was continuously withdrawn by overflowing from the outlet of the reactor. The reaction was conducted for 10 hours. After that period of time, analysis was made with respect to the reaction mixture withdrawn from the outlet of the reactor. As a result, it was found that the conversion of methacrolein was 56.8%, the selectivity for MMA was 91.2%, and the selectivity for propylene as a by-product was 1.03%, and that methyl formate was by-produced in an amount of 0.178 mol/mol of MMA.

EXAMPLE 24

The reaction for producing MMA conducted in Example 11 was further continued. 500 Hours after the start of the reaction, analysis was made with respect to the reaction mixture withdrawn from the outlet of the reactor, and the results of the analysis were compared with the results of the analysis of the reaction mixture which was obtained 100 hours after the start of the reaction. As a result, it was found that no significant change was observed with respect to the results of the MMA-producing reaction, except that the amount of the by-produced methyl formate was reduced from 0.045 mol/mol of MMA to 0.032 mol/mol of MMA. Analysis was also made with respect to a portion of the catalyst taken out from the outlet of the reactor, and the results of the analysis were compared with the results of the analysis conducted with respect to the catalysts at the time of 100 hours after the start of the reaction. As a result, it was found that no significant change was observed in the catalyst with respect to the Pd/Pb atomic ratio, the diffraction angle (2θ) for a maximum intensity peak in the powder X-ray diffraction pattern, and the ratio of the total intensity of two peaks ascribed to metallic palladium 3d electrons to the intensity of a peak ascribed to metallic lead 4f(7/2) electron which is multiplied by 1.75 in the X-ray photoelectron spectrum. However, the ratio of the total intensity of two peaks ascribed to metallic palladium 3d electrons to the total intensity of two peaks ascribed to ionic lead 4f electrons in the X-ray photoelectron spectrum of the catalyst was reduced from 1/0.11 to 1/0. {With respect to the catalyst intermediate used in Example 11, which had been prepared in Referential Example 1, the ratio of the total intensity of two peaks ascribed to metallic palladium 3d electrons to the total intensity of two peaks ascribed to ionic lead 4f electrons in the X-ray photoelectron spectrum thereof was 1/0.35.}

EXAMPLE 25

A reaction for producing methyl acrylate (MA) was conducted in substantially the same manner as in Example 21, except that the catalyst which was obtained in Example 14 was used and that acrolein was used instead of the methacrolein. The reaction mixture withdrawn from the outlet of the reactor 10 hours after the start of the reaction was analyzed. As a result, it was found that the conversion of acrolein was 61.2%, the selectivity for MA was 91.3%, and the selectivity for ethylene as a by-product was 1.2%, and that methyl formate was by-produced in an amount of 0.055 mol/mol of MA.

Referential Example 3

Aluminum nitrate and magnesium nitrate were dissolved in an aqueous silica sol {Snowtex N-30 (SiO$_2$ content: 30% by weight), manufactured and sold by Nissan Chemical Industries, Ltd., Japan} so that the Al/(Si+Al) proportion became 10 mol % and the Mg/(Si+Mg) proportion became 10 mol %. The resultant solution was subjected to spray drying by means of a spray dryer at 130° C., thereby obtaining particles having an average particle diameter of 60 μm. The obtained particles were calcined in air at 300° C. for 2 hours and subsequently at 600° C. for 3 hours, thereby obtaining a carrier for a catalyst. To the obtained carrier were added an aqueous solution of palladium chloride (15% by weight) and sodium chloride (10% by weight) and an aqueous solution of lead nitrate (13% by weight) so that the amounts of the palladium chloride and lead nitrate contained in the resultant mixture became 5.0 parts by weight in terms of Pd and 2.3 parts by weight in terms of Pb, respectively, relative to 100 parts by weight of the carrier. The resultant mixture was stirred at room temperature for 1 hour, thereby obtaining a carrier which adsorbs almost all of the palladium chloride and lead nitrate thereon. Thereafter, to the obtained carrier having adsorbed thereon the palladium chloride and lead nitrate was dropwise added, while stirring, an aqueous solution containing hydrazine in a molar amount which was 3 times as large as the total molar amount of the Pd and Pb adsorbed on the carrier, thereby reducing the palladium chloride and lead nitrate adsorbed on the carrier. Thus, a composition Pd$^{5.0}$Pb$^{2.3}$/SiO$_2$—Al$_2$O$_3$—MgO was obtained (hereinafter, the obtained composition is referred to as "catalyst intermediate"). The catalyst intermediate was analyzed with respect to the Pd/Pb atomic ratio, to the diffraction angle (2θ) in the powder X-ray diffraction pattern thereof at which the maximum intensity peak was exhibited, and to the ratio of the total intensity of two peaks ascribed to metallic palladium 3d electrons to the intensity of a peak ascribed to metallic lead 4f(7/2) electron which is multiplied by 1.75 in the X-ray photoelectron spectrum thereof, by the methods as mentioned above. As a result, it was found that the catalyst intermediate had a Pd/Pb atomic ratio of 3/0.70, and exhibited a maximum intensity peak at a diffraction angle (2θ) of 39.102° in the powder X-ray diffraction pattern thereof, and that the ratio of the total intensities of two peaks ascribed to metallic palladium 3d electrons to the intensity of a peak ascribed to metallic lead 4f(7/2) electron which is multiplied by 1.75 was 1/0.19.

EXAMPLE 26

An autoclave, which had a volume of 30 liters for a liquid phase, was charged with 2 kg of the catalyst intermediate prepared in Referential Example 3, 20 liters of an aqueous 6% by weight solution of sodium acetate monohydrate, 500 ml of an aqueous solution containing 55.8 g of lead acetate (this amount of lead acetate corresponds to a lead amount satisfying the Pd/Pb atomic ratio of 3/0.4 in terms of the ratio of the amount of palladium in the catalyst intermediate to the amount of lead charged above as the lead acetate), and an aqueous formaldehyde in an amount such that the molar ratio of the formaldehyde to the palladium of the catalyst intermediate became 10/1. The resultant mixture was stirred at 90° C. for 1 hour, to thereby effect an activation of the catalyst intermediate. The resultant activated catalyst was analyzed by the methods as mentioned above. As a result, it was found that the catalyst had a Pd/Pb atomic ratio of 3/1.07 and exhibited a maximum intensity peak at a diffraction angle (2θ) of 38.582° in the powder X-ray diffraction pattern thereof, and that the ratio of the total intensity of two peaks ascribed to metallic palladium 3d electrons to the intensity of a peak ascribed to metallic lead 4f(7/2) electron which is multiplied by 1.75 in the X-ray photoelectron spectrum was 1/0.48.

240 g of the activated catalyst was charged in a stainless, external circulation type bubble column reactor, which was equipped with a separator for a catalyst and had a volume of 1.2 liters for a liquid phase. Then, a 36.7% by weight solution of methacrolein in methanol, in which lead acetate had been dissolved so that the lead concentration of the resultant reaction system became 20 ppm by weight, and a 20 to 48% by weight aqueous NaOH solution were fed to the reactor at 0.54 liter/hr and 0.006 liter/hr, respectively (the methacrolein concentration of the reaction system consisting of the above-mentioned two different solutions was about 36% by weight), while introducing air to the reactor so that the oxygen concentration at the outlet of the reactor became 4.0% by volume (which is equivalent to the oxygen partial pressure of 0.20 kg/cm$^2$), thereby effecting a reaction for producing MMA. The reaction was conducted at a temperature of 80° C. under a pressure of 5 kg/cm$^2$. The concentration of NaOH was controlled so that the reaction system had a pH of 7.1. The reaction mixture obtained by the above reaction was continuously withdrawn by overflowing from the outlet of the reactor. The reaction was conducted for 10 hours. After that period of time, analysis was made with respect to the reaction mixture withdrawn from the outlet of the reactor. As a result, it was found that the conversion of methacrolein was 61.8%, the selectivity for MMA was 91.9%, and the selectivity for propylene as a by-product was 1.1%, and that methyl formate was by-produced in an amount of 0.045 mol/mol of MMA.

EXAMPLE 27

An autoclave, which had a volume of 30 liters for a liquid phase, was charged with 2 kg of the catalyst intermediate prepared in Referential Example 3 and 20 liters of an aqueous solution containing 57.3 g of lead nitrate (this amount of lead nitrate corresponds to a lead amount satisfying the Pd/Pb atomic ratio of 3/0.60 in terms of the ratio of the amount of palladium in the catalyst intermediate to the amount of lead charged above as the lead nitrate). The resultant mixture was stirred at 90° C. for 1 hour, while introducing a nitrogen gas containing 2% by volume of hydrogen to the autoclave at 5N liters/min, to thereby effect an activation of the catalyst intermediate. The resultant activated catalyst was analyzed by the methods as mentioned above. As a result, it was found that the catalyst had a Pd/Pb atomic ratio of 3/1.26 and exhibited a maximum intensity peak at a diffraction angle (2θ) of 38.698° in the powder X-ray diffraction pattern thereof, and that the ratio of the total intensity of two peaks ascribed to metallic palladium 3d electrons to the intensity of a peak ascribed to metallic lead 4f(7/2) electron which is multiplied by 1.75 in the X-ray photoelectron spectrum was 1/0.73. Using the activated catalyst, a reaction for producing MMA was conducted in substantially the same manner as in Example 26. The reaction mixture withdrawn from the outlet of the reactor was analyzed. As a result, it was found that the conversion of methacrolein was 57.2%, the selectivity for MMA was 88.7%, and the selectivity for propylene as a by-product was 2.2%, and that methyl formate was by-produced in an amount of 0.115 mol/mol of MMA.

EXAMPLE 28

An autoclave, which had a volume of 30 liters for a liquid phase, was charged with 20 liters of methanol. 28.1 g of lead acetate trihydrate (this amount of lead acetate trihydrate corresponds to a lead amount satisfying the Pd/Pb atomic ratio of 3/0.30 in terms of the ratio of the amount of palladium in the catalyst intermediate prepared in Referential Example 3 to the amount of lead charged above as the lead acetate trihydrate) was dissolved in the methanol to thereby obtain a solution. To the obtained solution was added 2 kg of the catalyst intermediate prepared in Referential Example 3. To the resultant mixture was dropwise added an aqueous 10% by weight solution of formaldehyde in an amount such that the molar ratio of the formaldehyde to the palladium of the catalyst intermediate became 10/1. The addition of the aqueous solution of formaldehyde was conducted for 1 hour. The resultant mixture was stirred at 90° C. for 3 hours, to thereby effect an activation of the catalyst intermediate. The resultant activated catalyst was analyzed by the methods as mentioned above. As a result, it was found that the catalyst had a Pd/Pb atomic ratio of 3/0.97 and exhibited a maximum intensity peak at a diffraction angle (2θ) of 38.676° in the powder X-ray diffraction pattern thereof, and that the ratio of the total intensity of two peaks ascribed to metallic palladium 3d electrons to the intensity of a peak ascribed to metallic lead 4f(7/2) electron which is multiplied by 1.75 in the X-ray photoelectron spectrum was 1/0.36. Using the activated catalyst, a reaction for producing MMA was conducted in substantially the same manner as in Example 26. The reaction mixture withdrawn from the outlet of the reactor 10 hours after the start of the reaction was analyzed. As a result, it was found that the conversion of methacrolein was 61.0%, the selectivity for MMA was 89.6%, and the selectivity for propylene as a by-product was 2.3%, and that methyl formate was by-produced in an amount of 0.043 mol/mol of MMA.

Comparative Example 11

A reaction for producing MMA was conducted in substantially the same manner as in Example 1, except that the catalyst intermediate prepared in Referential Example 3 was used as such. The reaction mixture withdrawn from the outlet of the reactor 10 hours after the start of the reaction was analyzed. As a result, it was found that the conversion of methacrolein was 57.8%, the selectivity for MMA was 84.3%, and the selectivity for propylene as a by-product was 7.3%, and that methyl formate was by-produced in an amount of 0.039 mol/mol of MMA.

Referential Example 4

Substantially the same procedure as in Referential Example 2 was repeated, except that 50.1 g of potassium acetate was used instead of the magnesium acetate, and that the amount of lead nitrate was changed to 37.9 g. As a result, a catalyst intermediate comprising a carrier having supported thereon 5.0 parts by weight of palladium, 2.37 parts by weight of lead and 2.0 parts by weight of potassium, relative to 100 parts by weight of the carrier, was obtained. The obtained catalyst intermediate was analyzed by the methods as mentioned above. As a result, it was found that the catalyst intermediate had a Pd/Pb atomic ratio of 3/0.73 and exhibited a maximum intensity peak at a diffraction angle (2θ) of 39.112° in the powder X-ray diffraction pattern thereof, and that the ratio of the total intensity of two peaks ascribed to metallic palladium 3d electrons to the intensity of a peak ascribed to metallic lead 4f(7/2) electron which is multiplied by 1.75 in the X-ray photoelectron spectrum was 1/0.18.

EXAMPLES 29 to 33

In Examples 29 to 33, catalyst intermediates which were prepared in the same manner as in Referential Example 4 were individually subjected to activation treatment in substantially the same manner as in Example 26, except that the activation conditions were changed as indicated in Table 3. The resultant activated catalysts were analyzed by the methods as mentioned above. Using the activated catalysts, reactions for producing MMA were individually conducted in substantially the same manner as in Example 26. The Pd/Pb atomic ratio of the activated catalyst, the diffraction angle (2θ) for a maximum intensity peak in the powder X-ray diffraction pattern of the activated catalyst, and the ratio of the total intensity of two peaks ascribed to metallic palladium 3d electrons to the intensity of a peak ascribed to metallic lead 4f(7/2) electron which is multiplied by 1.75 in the X-ray photoelectron spectrum of the activated catalyst in each of Examples 29 to 33 are shown in Table 3, together with the respective results of the analyses of the reaction mixtures obtained 10 hours after the start of the MMA-producing reactions.

TABLE 3

| | Conditions for activation | | | | | | Activated catalyst | | | | | |
|---|---|---|---|---|---|---|---|---|---|---|---|---|
| | Reducing agent/ solvent | Reducing agent/ Pd molar ratio | Pd/Pb (lead added) atomic ratio (1*) | Temperature (° C.) | Period (hr) | Fatty acid | | Pd/Pb atomic ratio | Diffraction angle (2θ) for maximum intensity peak | Intensity ratio of peaks (metallic Pd/metallic Pb)*2 | Conversion of methacrolein (%) | Selectivity for MMA (%) | Selectivity for propylene (%) | Amount of methyl formate produced (mol/mol of MMA) |
| Examples | | | | | | Type | Amount (% by weight) | | | | | | | |
| Example 29 | hydrazine/ water | 3.0 | 3/1.18 | 60 | 5 | — | — | 3/1.90 | 38.659° | 1/0.65 | 60.9 | 90.8 | 1.4 | 0.053 |
| Example 30 | sodium formate/ water | 5.0 | 3/0.49 | 90 | 1 | — | — | 3/1.21 | 38.582° | 1/0.51 | 61.1 | 91.3 | 1.1 | 0.044 |
| Example 31 | aqueous formaldehyde/ water | 2.1 | 3/0.43 | 90 | 2 | propionic acid | 5 | 3/1.14 | 38.621° | 1/0.42 | 62.3 | 90.9 | 1.3 | 0.038 |
| Example 32 | aqueous formaldehyde/ methanol | 1.0 | 3/0.36 | 160 | 0.5 | acetic acid | 4 | 3/1.09 | 38.614° | 1/0.39 | 61.8 | 91.5 | 0.82 | 0.039 |
| Example 33 | aqueous formaldehyde/ water | 10.0 | 3/0.51 | 90 | 1 | magnesium acetate | 4 | 3/1.22 | 38.592° | 1/0.41 | 62.9 | 91.0 | 1.0 | 0.031 |

Note:
*1) The Pd/Pb atomic ratio represents an atomic ratio of the palladium of the catalyst intermediate to the lead of the lead acetate monohydrate added to the reaction system.
*2) Ratio of the total intensity of two peaks ascribed to metallic palladium 3d electrons to the intensity of a peak ascribed to metallic lead 4f (7/2) electron which is multiplied by 1.75 in the X-ray photoelectron spectrum.

EXAMPLE 34

An agitation type reactor, which had a volume of 6 liters for a liquid phase, was charged with 1 kg of the catalyst intermediate prepared in Referential Example 3 and 5 liters of an aqueous solution containing 41.8 g of lead acetate trihydrate (this amount of lead acetate trihydrate corresponds to a supplementary lead amount necessary for changing the Pd/Pb atomic ratio of the catalyst to 3/1.3). The resultant solution was heated to 90° C., and to the heated solution was added an aqueous formaldehyde (formaldehyde content: 37% by weight) in an amount such that the molar ratio of the formaldehyde to the palladium of the catalyst intermediate became 10/1. The resultant mixture was stirred for 1 hour while maintaining the temperature of the mixture at 90° C., to thereby effect an activation of the catalyst intermediate. The resultant activated catalyst had a Pd/Pb atomic ratio of 3/1.27 and exhibited a maximum intensity peak at a diffraction angle (2θ) of 38.642° in the powder X-ray diffraction pattern thereof, and the ratio of the total intensity of two peaks ascribed to metallic palladium 3d electrons to the intensity of a peak ascribed to metallic lead 4f(7/2) electron which is multiplied by 1.75 in the X-ray photoelectron spectrum of the activated catalyst was 1/0.753.

Using 240 g of the activated catalyst, a reaction for producing MMA was conducted in substantially the same manner as in Example 26. Analysis was made with respect to the reaction mixture. As a result, it was found that the conversion of methacrolein was 56.8%, the selectivity for MMA was 91.2%, and the selectivity for propylene as a by-product was 1.43%, and that methyl formate was by-produced in an amount of 0.138 mol/mol of MMA.

EXAMPLE 35

Substantially the same procedure as in Referential Example 3 was repeated, except that the amount of the aqueous solution of lead nitrate added to the carrier was changed so that the amount of the lead nitrate contained in the resultant mixture became 4.2 parts by weight in terms of Pb, relative to 100 parts by weight of the carrier, to thereby obtain a composition ($Pd^{5.0}Pb^{4.2}/SiO_2$—$Al_2O_3$—$MgO$) (hereinafter, frequently referred to as "catalyst intermediate"). The catalyst intermediate had a Pd/Pb atomic ratio of 3/1.29 and exhibited a maximum intensity peak at a diffraction angle (2θ) of 38.913° in the powder X-ray diffraction pattern thereof, and the ratio of the total intensity of two peaks ascribed to metallic palladium 3d electrons to the intensity of a peak ascribed to metallic lead 4f(7/2) electron which is multiplied by 1.75 in the X-ray photoelectron spectrum of the catalyst intermediate was 1/0.18.

2 kg of the above-obtained catalyst intermediate and 3 liters of an aqueous 10% by weight solution of acetic acid were charged in an autoclave, which had a volume of 30 liters for a liquid phase, and was stirred at 90° C. for 1 hour. The resultant mixture was analyzed, and found to contain lead ions in a concentration of 750 ppm by weight. Thereafter, an aqueous formaldehyde was added to the above-obtained mixture in an amount such that the molar ratio of the formaldehyde to the palladium of the catalyst intermediate became 5/1. The resultant mixture was stirred at 90° C. for 1 hour to thereby effect an activation of the catalyst intermediate. The resultant activated catalyst had a Pd/Pb atomic ratio of 3/1.28 and exhibited a maximum intensity peak at a diffraction angle (2θ) of 38.611° in the powder X-ray diffraction pattern thereof, and the ratio of the total intensity of two peaks ascribed to metallic palladium 3d electrons to the intensity of a peak ascribed to metallic lead 4f(7/2) electron which is multiplied by 1.75 in the X-ray photoelectron spectrum of the activated catalyst was 1/0.38.

Two stainless, external circulation type bubble column reactors as used in Example 26, each of which was equipped with a separator for a catalyst and had a volume of 1.2 liters for a liquid phase, were connected to provide a first stage reactor and a second stage reactor which were connected in series. Each of the first stage and second stage reactors was charged with 240 g of the activated catalyst. Then, a series of reactions for producing MMA was conducted as follows. A 36.7% by weight solution of methacrolein in methanol, in which lead acetate had been dissolved so that the lead concentration of the resultant reaction system became 20 ppm by weight, and a 2 to 4% by weight solution of NaOH in methanol were continuously fed to the first stage reactor at 0.54 liter/hr and at 0.06 liter/hr, respectively (the methacrolein concentration of the reaction system consisting of the above-mentioned two different solutions was about 33% by weight), while introducing air to the first stage reactor so that the oxygen concentration at the outlet of the first stage reactor became 4.0% by volume (which is equivalent to the oxygen partial pressure of 0.20 kg/cm$^2$), to effect a reaction for producing MMA. The reaction was conducted at a temperature of 80° C. under a pressure of 5 kg/cm$^2$. The resultant reaction mixture containing the catalyst was continuously withdrawn by overflowing from the outlet of the first stage reactor and transferred to a liquid phase-solid phase separation zone, where a separation between the catalyst and the reaction mixture was effected. The separated catalyst was returned to the first stage reactor. The separated reaction mixture and a 2 to 4% by weight solution of NaOH in methanol were fed to the second stage reactor at 0.6 liter/hr and at 0.06 liter/hr, respectively. A gaseous phase withdrawn from the first stage reactor was fed to the second stage reactor while introducing fresh air to the second stage reactor so that the oxygen concentration at the outlet of the second stage reactor became 2.2% by volume (which is equivalent to the oxygen partial pressure of 0.11 kg/cm$^2$), to effect a reaction for producing MMA. The reaction was conducted at a temperature of 80° C. under a pressure of 4.6 kg/cm$^2$. The concentration of NaOH in the methanol solution fed to each of the first stage and second stage reactors was controlled so that the reaction system in each reactor had a pH of 7.1. The reaction mixture obtained in the second stage reactor was continuously withdrawn by overflowing from the outlet of the second stage reactor. Analysis was made with respect to the reaction mixture which was withdrawn from the outlet of the second stage reactor 10 hours after the start of the two-stage reaction. As a result, it was found that the conversion of methacrolein was 85.9%, the selectivity for MMA was 91.5%, and the selectivity for propylene as a by-product was 1.0%, and that methyl formate was by-produced in an amount of 0.046 mol/mol of MMA.

EXAMPLE 36

100 parts by weight of a silica gel (Cariact 10, manufactured and sold by Fuji Sylysia Chemical, Ltd., Japan) was impregnated with 1000 parts by weight of an aqueous 0.1 N ammonia, and allowed to stand for 2 days. After that period of time, the resultant mixture was subjected to filtration to thereby obtain a carrier in the form of a filter cake. 1000 parts by weight of water was added to the obtained carrier. To the resultant mixture was added an aqueous 0.01 M solution of {Pd(NH$_3$)$_4$}Cl$_2$ in an amount of 5 parts by weight in terms of Pd, while stirring at 60° C. The resultant mixture was allowed to stand overnight to thereby adsorb the {Pd(NH$_3$)$_4$}Cl$_2$ on the carrier. The resultant carrier adsorbing the {Pd(NH$_3$)$_4$}Cl$_2$ thereon was dried at 80° C. for 6 hours in vacuo. The dried substance was impregnated, with stirring, with an aqueous solution of 3.96 parts by weight of lead acetate and 0.11 parts by weight of thallium acetate, relative to 100 parts by weight of water, followed by drying on a boiling water bath, to thereby obtain a carrier adsorbing {Pd(NH$_3$)$_4$}Cl$_2$, lead acetate and thallium acetate thereon. The obtained carrier was added to 1000 parts by weight of an aqueous formaldehyde (which had been heated at 60° C.) so that the molar ratio of the formaldehyde to the {Pd(NH$_3$)$_4$}Cl$_2$ (in terms of palladium) adsorbed on the carrier became 3/1. The resultant mixture was allowed to stand at 60° C. for 3 hours to thereby reduce the {Pd(NH$_3$)$_4$}Cl$_2$, lead acetate and thallium acetate adsorbed on the carrier, followed by washing with water. Thus, a composition ($Pd^{5.0}Pb^{3.96}Ti^{0.11}/SiO_2$) (hereinafter, the obtained composition is referred to as "catalyst intermediate") was obtained. The catalyst intermediate was subjected to activation treatment in substantially the same manner as in Example 26. The activated catalyst had a Pd/Pb atomic ratio of 3/1.22 and exhibited a maximum intensity peak at a diffraction angle (2θ) of 38.621° in the powder X-ray diffraction pattern thereof, and the ratio of the total intensity of two peaks ascribed to metallic palladium 3d electrons to the intensity of a peak ascribed to metallic lead 4f(7/2) electron which is multiplied by 1.75 in the X-ray photoelectron spectrum of the activated catalyst was 1/0.49.

An agitation type reactor, which had the same volume for a liquid phase as that of the bubble column reactor as used in Example 26, was charged with 200 g of the activated catalyst. A reaction for producing MMA was conducted in substantially the same manner as in Example 35, except that the amount of the lead acetate added to the 36.7% by weight solution of methacrolein in methanol was changed so that the lead concentration of the reaction system was 10 ppm by weight. Analysis was made with respect to the reaction mixture withdrawn from the outlet of the reactor 10 hours after the start of the reaction. As a result, it was found that the conversion of methacrolein was 62.1%, the selectivity for MMA was 91.4%, and the selectivity for propylene as a by-product was 1.1%, and that methyl formate was by-produced in an amount of 0.044 mol/mol of MMA.

EXAMPLE 37

100 Parts by weight of an alumina carrier {AF (particle diameter: 10–150 μm), manufactured and sold by Sumitomo Co., Ltd., Japan} was added to 200 parts by weight of an aqueous solution containing lead nitrate, bismuth nitrate and magnesium nitrate in amounts of 4.02 parts by weight (in terms of lead), 0.23 parts by weight (in terms of bismuth) and 2.0 parts by weight (in terms of magnesium), respectively, to thereby impregnate the alumina with the aqueous solution. The impregnation was effected on a boiling water bath to thereby adsorb the lead nitrate, bismuth nitrate and magnesium nitrate on the carrier, followed by drying. The resultant dried substance was calcined in air at 500° C. for 3 hours and then, added to an aqueous solution of palladium chloride (15% by weight) and sodium chloride (10% by weight) being employed in an amount such that the amount of the palladium chloride became 5 parts by weight, relative to 100 parts by weight of the carrier. The resultant mixture was stirred at room temperature for 1 hour, thereby adsorbing the palladium chloride on the carrier. Thereafter, to the resultant carrier adsorbing palladium chloride, lead nitrate, bismuth nitrate and magnesium nitrate thereon was dropwise added, while stirring, an aqueous solution of hydrazine in an amount which was 3 times as large as the molar amount of the palladium chloride, thereby reducing the palladium chloride, lead nitrate, bismuth nitrate and magnesium nitrate adsorbed on the carrier. Thus, a composition $Pd^{5.0}Pb^{4.02}Bi^{0.22}Mg^{2.0}/Al_2O_3$ was obtained (hereinafter, the obtained composition is referred to as "catalyst intermediate").

The catalyst intermediate was subjected to activation treatment in substantially the same manner as in Example 26, to thereby obtain an activated catalyst. The obtained activated catalyst had a Pd/Pb atomic ratio of 3/1.24 and exhibited a maximum intensity peak at a diffraction angle (2θ) of 38.611° in the powder X-ray diffraction pattern thereof, and the ratio of the total intensity of two peaks ascribed to metallic palladium 3d electrons to the intensity of a peak ascribed to metallic lead 4f(7/2) electron which is multiplied by 1.75 in the X-ray photoelectron spectrum of the catalyst intermediate was 1/0.51.

Using the above-obtained activated catalyst, a reaction for producing MMA was conducted in substantially the same manner as in Example 36 obtained 10 hours after the start of the reaction. Analysis was made with respect to the reaction mixture. As a result, it was found that the conversion of methacrolein was 61.3%, the selectivity for MMA was 90.8%, and the selectivity for propylene as a by-product was 1.3%, and that methyl formate was by-produced in an amount of 0.052 mol/mol of MMA.

EXAMPLE 38

Using the activated catalyst obtained in Example 37, a reaction for producing methyl acrylate (MA) was conducted in substantially the same manner as in Example 36, except that acrolein was used instead of the methacrolein.

Analysis was made with respect to the obtained reaction mixture obtained 10 hours after the start of the reaction. As a result, it was found that the conversion of acrolein was 57.8%, the selectivity for MA was 92.1%, and the selectivity for ethylene as a by-product was 1.1%, and that methyl formate was by-produced in an amount of 0.039 mol/mol of MA.

Referential Example 5

Aluminum nitrate and magnesium nitrate were dissolved in an aqueous silica sol {Snowtex N-30 ($SiO_2$ content: 30% by weight), manufactured and sold by Nissan Chemical Industries, Ltd., Japan} so that the Al/(Si+Al) proportion became 10 mol % and the Mg/(Si+Mg) proportion became 10 mol %. The resultant solution was subjected to spray drying by means of a spray dryer at 130° C., thereby obtaining particles having an average particle diameter of 60 μm. The obtained particles were calcined in air at 300° C. for 2 hours and subsequently at 600° C. for 3 hours, thereby obtaining a carrier for a catalyst. To the obtained carrier were added an aqueous solution of palladium chloride (15% by weight) and sodium chloride (10% by weight) and an aqueous solution of lead nitrate (13% by weight) so that the amounts of the palladium chloride and lead nitrate contained in the resultant mixture became 5 parts by weight in terms of Pd and 4.2 parts by weight in terms of Pb, respectively, relative to 100 parts by weight of the carrier. The resultant mixture was stirred at room temperature for 1 hour, thereby obtaining a carrier adsorbing almost all of the palladium chloride and lead nitrate thereon. Thereafter, to the obtained carrier which adsorbed the palladium chloride and lead nitrate thereon was dropwise added, while stirring, an aqueous solution containing hydrazine in a molar amount which was 3 times as large as the total molar amount of the Pd and Pb adsorbed on the carrier, thereby reducing the palladium chloride and lead nitrate adsorbed on the carrier. Thus, a composition ($Pd^{5.0}Pb^{4.2}/SiO_2—Al_2O_3—MgO$) was obtained (hereinafter, the obtained composition is frequently referred to simply as "catalyst intermediate"). The catalyst intermediate was analyzed by the methods as mentioned above. As a result, it was found that the catalyst intermediate had a Pd/Pb atomic ratio of 3/1.29 and exhibited a maximum intensity peak at a diffraction angle (2θ) of 38.913° in the powder X-ray diffraction pattern thereof, and that the ratio of the total intensity of two peaks ascribed to metallic palladium 3d electrons to the intensity of a peak ascribed to metallic lead 4f(7/2) electron which is multiplied by 1.75 in the X-ray photoelectron spectrum of the catalyst intermediate was 1/0.187.

EXAMPLE 39

The catalyst intermediate prepared in Referential Example 5 was subjected to activation treatment as follows. 500 g of the catalyst intermediate prepared in Referential Example 5 was charged in a 10 cm φ×1 m quartz glass cylindrical reactor. A nitrogen gas containing 2% by volume of oxygen was flowed through the reactor at 650 N liters/hr. While flowing the oxygen-containing nitrogen gas, the temperature of the reactor was elevated at a rate of 50° C./hr until the temperature reached 400° C. and then, the temperature of the reactor was maintained at 400° C. for 5 hours to thereby effect oxidation of the catalyst intermediate, followed by cooling to room temperature under flowing of a nitrogen gas. Subsequently, a nitrogen gas containing 8% by volume of methanol gas was flowed through the reactor at 650 N liters/hr instead of the above-mentioned oxygen-containing nitrogen gas. While flowing the methanol gas-containing nitrogen gas, the temperature of the reactor was elevated at a rate of 50° C./hr until the temperature reached 400° C., and the temperature of the reactor was maintained at 400° C. for 4 hours to thereby effect reduction of the catalyst intermediate, followed by cooling to room temperature under flowing of a nitrogen gas. Thereafter, while flowing a hydrogen gas through the reactor at 50 N liters/hr instead of the nitrogen gas, the temperature of the reactor was elevated at a rate of 50° C./hr until the temperature reached 300° C., and maintained at 300° C. for 5 hours to thereby effect a further reduction of the catalyst intermediate. Then, the reactor was cooled under flowing of a nitrogen gas. Thus, an activation of the catalyst intermediate was completed. Analysis was made with respect to the resultant activated catalyst. As a result, it was found that the activated catalyst had a Pd/Pb atomic ratio of 3/1.28 and exhibited a maximum intensity peak at a diffraction angle (2θ) of 38.621° in the powder X-ray diffraction pattern thereof, and that the ratio of the total intensity of two peaks ascribed to metallic palladium 3d electrons to the intensity of a peak ascribed to metallic lead 4f(7/2) electron which is multiplied by 1.75 in the X-ray photoelectron spectrum of the activated catalyst was 1/0.354.

240 g of the activated catalyst was charged in an external circulation type bubble column reactor, which was equipped with a separator for a catalyst and had a volume of 1.2 liters for a liquid phase, and a reaction for producing MMA was carried out as follows. A 36.7% by weight solution of methacrolein in methanol, in which lead acetate had been dissolved so that the lead concentration of the resultant reaction system became 20 ppm by weight, and a 2 to 4% by weight solution of NaOH in methanol were continuously fed to the reactor at 0.54 liter/hr and at 0.06 liter/hr, respectively (the methacrolein concentration of the reaction system consisting of the above-mentioned two different solutions was about 33% by weight), while introducing air to the reactor so that the oxygen concentration at the outlet of the reactor became 4.0% by volume (which is equivalent to the oxygen partial pressure of 0.20 kg/cm$^2$), to effect a reaction for producing MMA. The reaction was conducted at a temperature of 80° C. under a pressure of 5 kg/cm$^2$. The concentration of NaOH in the above-mentioned methanol solution of NaOH was controlled so that the reaction system had a pH of 7.1. The reaction mixture obtained by the above reaction was continuously withdrawn by overflowing from the outlet of the reactor. Analysis was made with respect to the reaction mixture which was withdrawn from the outlet of the reactor 10 hours after the start of the reaction. As a result, it was found that the conversion of methacrolein was 61.3%, the selectivity for MMA was 90.8%, and the selectivity for propylene as a by-product was 1.3%, and that methyl formate was by-produced in an amount of 0.051 mol/mol of MMA.

Comparative Example 12

Substantially the same procedure as conducted for activating the catalyst intermediate in Example 39 was repeated, except that the oxidation with the oxygen-containing nitrogen gas was not conducted.

The resultant catalyst intermediate had a Pd/Pb atomic ratio of 3/1.28 and exhibited a maximum intensity peak at a diffraction angle (2θ) of 38.832° in the powder X-ray diffraction pattern thereof, and the ratio of the total intensity of two peaks ascribed to metallic palladium 3d electrons to the intensity of a peak ascribed to metallic lead 4f(7/2) electron which is multiplied by 1.75 in the X-ray photoelectron spectrum of the catalyst intermediate was 1/0.261.

Using the catalyst intermediate, a reaction for producing MMA was conducted in substantially the same manner as in Example 39. Analysis was made with respect to the reaction mixture withdrawn from the outlet of the reactor 10 hours after the start of the reaction. As a result, it was found that the conversion of methacrolein was 59.1%, the selectivity for MMA was 85.2%, and the selectivity for propylene as a by-product was 5.7%, and that methyl formate was by-produced in an amount of 0.132 mol/mol of MMA.

EXAMPLE 40

Substantially the same procedure as conducted for activating the catalyst intermediate in Example 39 was repeated with respect to the catalyst intermediate prepared in Referential Example 5, except that a sequence of the oxidation with the oxygen-containing nitrogen gas and the reduction with the methanol gas-containing nitrogen gas was conducted twice, followed by reduction with a hydrogen gas, to thereby obtain an activated catalyst. The obtained activated catalyst had a Pd/Pb atomic ratio of 3/1.28 and exhibited a maximum intensity peak at a diffraction angle (2θ) of 38.605° in the powder X-ray diffraction pattern thereof, and the ratio of the total intensity of two peaks ascribed to metallic palladium 3d electrons to the intensity of a peak ascribed to metallic lead 4f(7/2) electron which is multiplied by 1.75 in the X-ray photoelectron spectrum of the activated catalyst was 1/0.412.

Using the activated catalyst, a reaction for producing MMA was conducted in substantially the same manner as in Example 39. Analysis was made with respect to the reaction mixture withdrawn from the outlet of the reactor 10 hours after the start of the reaction. As a result, it was found that the conversion of methacrolein was 61.8%, the selectivity for MMA was 91.8%, and the selectivity for propylene as a by-product was 1.1%, and that methyl formate was by-produced in an amount of 0.043 mol/mol of MMA.

EXAMPLE 41

Substantially the same procedure as conducted for activating the catalyst intermediate in Example 39 was repeated with respect to the catalyst intermediate prepared in Referential Example 5, except that the reduction with the methanol gas-containing nitrogen gas was not conducted. Analysis was made with respect to the resultant activated catalyst. As a result, it was found that the activated catalyst had a Pd/Pb atomic ratio of 3/1.28 and exhibited a maximum intensity peak at a diffraction angle (2θ) of 38.685° in the powder X-ray diffraction pattern thereof, and that the ratio of the total intensity of two peaks ascribed to metallic palladium 3d electrons to the intensity of a peak ascribed to metallic lead 4f(7/2) electron which is multiplied by 1.75 in the X-ray photoelectron spectrum of the activated catalyst was 1/0.378.

Using the activated catalyst, a reaction for producing MMA was conducted in substantially the same manner as in Example 39. Analysis was made with respect to the reaction mixture withdrawn from the outlet of the reactor 10 hours after the start of the reaction. As a result, it was found that the conversion of methacrolein was 61.4%, the selectivity for MMA was 89.9%, and the selectivity for propylene as a by-product was 1.9 A, and that methyl formate was by-produced in an amount of 0.053 mol/mol of MMA.

EXAMPLE 42

Substantially the same procedure as conducted for activating the catalyst intermediate in Example 39 was repeated, except that the catalyst intermediate prepared in Referential Example 2 was used.

The resultant activated catalyst had a Pd/Pb atomic ratio of 3/0.98 and exhibited a maximum intensity peak at a diffraction angle (2θ) of 38.697° in the powder X-ray diffraction pattern thereof, and the ratio of the total intensity of two peaks ascribed to metallic palladium 3d electrons to the intensity of a peak ascribed to metallic lead 4f(7/2) electron which is multiplied by 1.75 in the X-ray photoelectron spectrum of the activated catalyst was 1/0.245.

200 g of the activated catalyst was charged in an agitation type reactor which had the same volume for a liquid phase as that of the bubble column reactor as used in Example 39, and a reaction for producing MMA was carried out as follows. A 36.7% by weight solution of methacrolein in methanol, in which lead acetate had been dissolved so that the lead concentration of the resultant reaction system became 50 ppm by weight, and a 2 to 4% by weight solution of NaOH in methanol were continuously fed to the reactor at 0.54 liter/hr and at 0.06 liter/hr, respectively (the methacrolein concentration of the reaction system consisting of the above-mentioned two different solutions was about 33% by weight), while introducing air to the reactor so that the oxygen concentration at the outlet of the reactor became 4.0% by volume (which is equivalent to the oxygen partial pressure of 0.20 kg/cm$^2$), thereby effecting a reaction for producing MMA. The reaction was conducted at a temperature of 80° C. under a pressure of 5 kg/cm$^2$. The concentration of NaOH in the above-mentioned methanol solution of NaOH was controlled so that the reaction system had a pH of 7.1. The reaction mixture obtained by the above reaction was continuously withdrawn by overflowing from the outlet of the reactor. Analysis was made with respect to the reaction mixture which was withdrawn from the outlet of the reactor 10 hours after the start of the reaction. As a result, it was found that the conversion of methacrolein was 59.8%, the selectivity for MMA was 89.7%, and the selectivity for propylene as a by-product was 2.08%, and that methyl formate was by-produced in an amount of 0.071 mol/mol of MMA.

EXAMPLE 43

Substantially the same procedure as in Referential Example 5 was repeated, except that the amount of the aqueous solution of lead nitrate added to the carrier was changed so that the amount of the lead nitrate contained in the resultant mixture became 6.5 parts by weight in terms of Pb, relative to 100 parts by weight of the carrier, to thereby obtain a catalyst intermediate (Pd$^{5.0}$Pb$^{6.5}$/SiO$_2$—Al$_2$O$_3$—MgO). The obtained catalyst intermediate had a Pd/Pb atomic ratio of 3/1.95 and exhibited a maximum intensity peak at a diffraction angle (2θ) of 38.745° in the powder X-ray diffraction pattern thereof, and the ratio of the total intensity of two peaks ascribed to metallic palladium 3d electrons to the intensity of a peak ascribed to metallic lead 4f(7/2) electron which is multiplied by 1.75 in the X-ray photoelectron spectrum of the catalyst intermediate was 1/1.24.

The above-obtained catalyst intermediate was subjected to activation treatment in substantially the same manner as in Example 39. 300 g of the activated catalyst and 3 liters of an aqueous 10% by weight acetic acid solution were charged in an autoclave which had a volume of 30 liters for a liquid phase. An aqueous 10% by weight acetic acid solution was continuously fed to the autoclave at 1 liter/hr while stirring, to thereby effect an activation of the catalyst intermediate. The activation was conducted at 90° C. for 10 hours. The resultant activated catalyst had a Pd/Pb atomic ratio of 3/1.25 and exhibited a maximum intensity peak at a diffraction angle (2θ) of 38.611° in the powder X-ray diffraction pattern thereof, and the ratio of the total intensity of two peaks ascribed to metallic palladium 3d electrons to the intensity of a peak ascribed to metallic lead 4f(7/2) electron which is multiplied by 1.75 in the X-ray photoelectron spectrum of the activated catalyst was 1/0.212.

A reaction for producing MMA was carried out in substantially the same manner as in Example 42. Analysis was made with respect to the reaction mixture withdrawn from the outlet of the reactor 10 hours after the start of the reaction. As a result, it was found that the conversion of methacrolein was 62.3%, the selectivity for MMA was 90.2%, and the selectivity for propylene as a by-product was 1.3%, and that methyl formate was by-produced in an amount of 0.049 mol/mol of MMA.

EXAMPLES 44 to 47

In each of Examples 44 to 47, a catalyst intermediate shown in Table 4 was subjected to activation treatment in substantially the same manner as in Example 39, and a reaction for producing MMA was carried out in substantially the same manner as in Example 42. The composition of the catalyst intermediate, the Pd/Pb atomic ratio of the activated catalyst, the diffraction angle (2θ) for a maximum intensity peak in the powder X-ray diffraction pattern of the activated catalyst, and the ratio of the total intensity of two peaks ascribed to metallic palladium 3d electrons to the intensity of a peak ascribed to metallic lead 4f(7/2) electron which is multiplied by 1.75 in the X-ray photoelectron spectrum of the activated catalyst in each of Examples 44 to 47 are shown in Table 4, together with the respective results of the analyses of the reaction mixtures obtained by the MMA-producing reactions.

TABLE 4

| | | | | Activated catalyst | | | | |
|---|---|---|---|---|---|---|---|---|
| Examples | Composition of catalyst intermediate [catalyst active species (*1)/carrier] | Pd/Pb atomic ratio | Diffraction angle (2θ) for maximum intensity peak | Intensity ratio of peaks (metallic Pd/metallic Pb)*3 | Conversion of methacrolein (%) | Selectivity for MMA (%) | Selectivity for propylene (%) | Amount of methyl formate produced (mol/mol of MMA) |
| Example 44 | $Pd^{5.0}Pb^{2.89}Mg^{5.0}/SiO_2$ | 3/0.89 | 38.679° | 1/0.23 | 62.4 | 89.4 | 2.12 | 0.044 |
| Example 45 | $Pd^{5.0}Pb^{3.63}K^{2.0}/Al_2O_3$ | 3/1.12 | 38.656° | 1/0.44 | 69.4 | 90.3 | 1.65 | 0.065 |
| Example 46 | $Pd^{5.0}Pb^{4.06}Tl^{0.13}/SiO_2$—$Al_2O_3$ (*2) | 3/1.25 | 38.633° | 1/0.45 | 63.5 | 91.2 | 1.24 | 0.074 |
| Example 47 | $Pd^{5.0}Pb^{3.31}Bi^{0.23}/SiO_2$—$Al_2O_3$ (*2) | 3/1.02 | 38.655° | 1/0.34 | 64.3 | 90.7 | 1.87 | 0.061 |

Note:
*1) The superscript numerals indicated at the right-hand of the elements of each of the catalyst active species of the respective catalyst intermediates represent parts by weight, relative to 100 parts by weight of the carrier.
*2) In the carrier $SiO_2$—$Al_2O_3$, the Al/(Al + Si) proportion is 30 mol %.
*3) Ratio of the total intensity of two peaks ascribed to metallic palladium 3d electrons to the intensity of a peak ascribed to metallic lead 4f (7/2) electron which is multiplied by 1.75 in the X-ray photoelectron spectrum.

EXAMPLE 48

Using the activated catalyst obtained in Example 43, a reaction for producing methyl acrylate (MA) was conducted in substantially the same manner as in Example 47, except that acrolein was used instead of the methacrolein. Analysis was made with respect to the reaction mixture obtained 10 hours after the start of the reaction. As a result, it was found that the conversion of acrolein was 61.9%, the selectivity for MA was 90.5%, and the selectivity for propylene as a by-product was 1.45%, and that methyl formate was by-produced in an amount of 0.065 mol/mol of MA.

Referential Example 6

Aluminum nitrate and magnesium nitrate were dissolved in an aqueous silica sol {Snowtex N-30 ($SiO_2$ content: 30% by weight), manufactured and sold by Nissan Chemical Industries, Ltd., Japan} so that the Al/(Si+Al) proportion became 10 mol % and the Mg/(Si+Mg) proportion became 10 mol %. The resultant solution was subjected to spray drying by means of a spray dryer at 130° C., thereby obtaining particles having an average particle diameter of 60 μm. The obtained particles were calcined in air at 300° C. for 2 hours and subsequently at 600° C. for 3 hours, thereby obtaining a carrier for a catalyst. To the obtained carrier were added an aqueous solution of palladium chloride (15% by weight) and sodium chloride (10% by weight) and an aqueous solution of lead nitrate (13% by weight) so that the amounts of the palladium chloride and lead nitrate contained in the resultant mixture became 5 parts by weight in terms of Pd and 9.7 parts by weight in terms of Pb, respectively, relative to 100 parts by weight of the carrier. The resultant mixture was stirred at room temperature for 1 hour, thereby obtaining carrier adsorbing almost all of the palladium chloride and lead nitrate thereon. Thereafter, to the obtained carrier which adsorbed the palladium chloride and lead nitrate thereon was dropwise added, while stirring, an aqueous solution containing hydrazine in a molar amount which was 3 times as large as the total molar amount of the Pd and Pb adsorbed on the carrier, thereby reducing the palladium chloride and lead nitrate adsorbed on the carrier. Thus, a composition $Pd^{5.0}Pb^{9.7}/SiO_2$—$Al_2O_3$—MgO was obtained (hereinafter, the obtained composition is frequently referred to simply as "catalyst intermediate"). The obtained catalyst intermediate was analyzed with respect to the Pd/Pb atomic ratio, to the maximum intensity peak at a diffraction angle (2θ) in the powder X-ray diffraction pattern thereof, and to the ratio of the total intensity of two peaks ascribed to metallic palladium 3d electrons to the intensity of a peak ascribed to metallic lead 4f(7/2) electron which is multiplied by 1.75 in the X-ray photoelectron spectrum thereof, by the methods as mentioned above. As a result, it was found that the catalyst had a Pd/Pb atomic ratio of 3/2.98 and exhibited a maximum intensity peak at a diffraction angle (2θ) of 38.685° in the powder X-ray diffraction pattern thereof, and that the ratio of the total intensity of two peaks ascribed to metallic palladium 3d electrons to the intensity of a peak ascribed to metallic lead 4f(7/2) electron which is multiplied by 1.75 was 1/1.94.

EXAMPLE 49

A 30-liter autoclave was charged with 2 kg of the catalyst intermediate prepared in Referential Example 6. An activation treatment of the catalyst intermediate was conducted at 80° C. for 15 hours, while continuously feeding an aqueous 10% by weight solution of acetic acid to the reactor at 10 liters/hr. The resultant activated catalyst had a Pd/Pb atomic ratio of 3/1.03 and exhibited a maximum intensity peak at a diffraction angle (2θ) of 38.678° in the powder X-ray diffraction pattern thereof, and the ratio of the total intensity of two peaks ascribed to metallic palladium 3d electrons to the intensity of a peak ascribed to metallic lead 4f(7/2) electron which is multiplied by 1.75 in the X-ray photoelectron spectrum of the activated catalyst was 1/0.234.

240 g of the activated catalyst was charged in a stainless, external circulation type bubble column reactor which was equipped with a separator for a catalyst and had a volume of 1.2 liters for a liquid phase, and a reaction for producing MMA was carried out as follows. A 36.7% by weight solution of methacrolein in methanol, in which lead acetate had been dissolved so that the lead concentration of the resultant reaction system became 50 ppm by weight, and a 2 to 4% by weight solution of NaOH in methanol were continuously fed to the reactor at 0.54 liter/hr and at 0.06 liter/hr, respectively (the methacrolein concentration of the reaction system consisting of the above-mentioned two different solutions was about 33% by weight), while introducing air to the reactor so that the oxygen concentration at the outlet of the reactor became 4.0% by volume (which is equivalent to the oxygen partial pressure of 0.20 kg/cm²), thereby effecting a reaction for producing MMA. The reaction was conducted at a temperature of 80° C. under a pressure of 5 kg/cm². The concentration of NaOH in the above-mentioned methanol solution of NaOH was controlled so that the reaction system had a pH of 7.1. The reaction mixture obtained by the above reaction was continuously withdrawn by overflowing from the outlet of the reactor. Analysis was made with respect to the reaction mixture which was withdrawn from the outlet of the reactor 10 hours after the start of the reaction. As a result, it was found that the conversion of methacrolein was 61.1%, the selectivity for MMA was 89.7%, and the selectivity for propylene as a by-product was 2.5%, and that methyl formate was by-produced in an amount of 0.032 mol/mol of MMA.

Comparative Example 13

The catalyst intermediate prepared in Referential Example 6 was subjected to activation treatment in substantially the same manner as in Example 49, except that an aqueous 5% by weight solution of hydrochloric acid was used instead of the aqueous solution of acetic acid. The resultant activated catalyst was analyzed by the methods as mentioned above. As a result, it was found that the activated catalyst had a Pd/Pb atomic ratio of 3/0.74 and exhibited a maximum intensity peak at a diffraction angle (2θ) of 38.743° in the powder X-ray diffraction pattern thereof, and the ratio of the total intensity of two peaks ascribed to metallic palladium 3d electrons to the intensity of a peak ascribed to metallic lead 4f(7/2) electron which is multiplied by 1.75 in the X-ray photoelectron spectrum of the activated catalyst was 1/0.185.

thereby obtain a catalyst intermediate ($Pd^{5.0}Pb^{11.5}Tl^{0.11}/SiO_2$). The obtained catalyst intermediate had a Pd/Pb atomic ratio of 3/3.54 and exhibited a maximum intensity peak at a diffraction angle (2θ) of 38.688° in the powder X-ray diffraction pattern thereof, and the ratio of the total intensity of two peaks ascribed to metallic palladium 3d electrons to a peak ascribed to metallic lead 4f(7/2) electron which is multiplied by 1.75 in the X-ray photoelectron spectrum of the catalyst intermediate was 1/1.21.

EXAMPLES 50 to 54

In each of Examples 50 to 54, substantially the same procedure as in Example 49 was repeated, except that the catalyst intermediate prepared in Referential Example 7 was used instead of the catalyst intermediate prepared in Referential Example 6 and that a fatty acid shown in Table 5 was used for activating the catalyst intermediate instead of the acetic acid. The Pd/Pb atomic ratio of the activated catalyst, the diffraction angle (2θ) for a maximum intensity peak in the powder X-ray diffraction pattern of the activated catalyst and the ratio of the total intensity of two peaks ascribed to metallic palladium 3d electrons to the intensity of a peak ascribed to metallic lead 4f(7/2) electron which is multiplied by 1.75 in the X-ray photoelectron spectrum of the activated catalyst are shown in Table 5, together with the respective results of the analyses of the reaction mixtures obtained 10 hours after the start of the reactions.

TABLE 5

| | Lower fatty acid | | Activated catalyst | | | | | |
|---|---|---|---|---|---|---|---|---|
| Examples | Type | Amount (% by weight) | Pd/Pb atomic ratio | Diffraction angle (2θ) for maximum intensity peak | Intensity ratio of peaks (metallic Pd/metallic Pb)*1 | Conversion of methacrolein (%) | Selectivity for MMA (%) | Selectivity for propylene (%) | Amount of methyl formate produced (mol/mol of MMA) |
| Example 50 | formic acid | 10.0 | 3/1.02 | 38.679° | 1/0.26 | 61.9 | 89.3 | 2.34 | 0.045 |
| Example 51 | acetic acid | 5.0 | 3/1.13 | 38.691° | 1/0.42 | 62.2 | 89.1 | 2.43 | 0.058 |
| Example 52 | propionic | 10.0 | 3/1.04 | 38.682° | 1/0.28 | 63.2 | 90.1 | 2.11 | 0.044 |
| Example 53 | methacrylic acid | 10.0 | 3/0.98 | 38.677° | 1/0.25 | 64.3 | 89.5 | 2.36 | 0.039 |
| Example 54 | maleic acid | 5.0 | 3/0.89 | 38.691° | 1/0.17 | 58.1 | 88.6 | 3.11 | 0.035 |

Note:
*1) Ratio of the total intensity of two peaks ascribed to metallic palladium 3d electrons to the intensity of a peak ascribed to metallic lead 4f (7/2) electron which is multiplied by 1.75 in the X-ray photoelectron spectrum.

Using the activated catalyst, substantially the same procedure for producing MMA as in Example 49 was repeated. Analysis was made with respect to the reaction mixture which was withdrawn from the outlet of the reactor 10 hours after the start of the reaction. As a result, it was found that the conversion of methacrolein was 56.8%, the selectivity for MMA was 86.4%, and the selectivity for propylene as a by-product was 4.8%, and that methyl formate was by-produced in an amount of 0.043 mol/mol of MMA.

Referential Example 7

Substantially the same procedure for preparing the catalyst intermediate as in Example 36 was repeated, except that the lead acetate was used in an amount of 11.5 parts by weight, relative to 100 parts by weight of the carrier, to

EXAMPLE 55

Substantially the same procedure as in Example 37 was repeated, except that potassium nitrate was used instead of the magnesium nitrate, to thereby obtain a catalyst intermediate having a composition of $Pd^{5.0}Pb^{8.6}B_i^{0.23}K^{2.0}/Al_2O_3$ (the Pd/Pb atomic ratio: 3/2.65). The obtained catalyst intermediate was subjected to activation treatment in substantially the same manner as in Example 1. The resultant activated catalyst had a Pd/Pb atomic ratio of 3/0.98 and exhibited a maximum intensity peak at a diffraction angle (2θ) of 38.691° in the powder X-ray diffraction pattern thereof, and the ratio of the total intensity of two peaks ascribed to metallic palladium 3d electrons to the intensity of a peak ascribed to metallic lead 4f(7/2) electron which is multiplied by 1.75 in the X-ray photoelectron spectrum of the activated catalyst was 1/0.232.

200 g of the activated catalyst was charged in an agitation type reactor which had the same volume for a liquid phase as that of the bubble column reactor as used in Example 49. A 36.7% by weight solution of acrolein in methanol, in which lead acetate had been dissolved so that the lead concentration of the resultant reaction system became 50 ppm by weight, and a 2 to 4% by weight solution of NaOH in methanol were continuously fed to the reactor at 0.54 liter/hr and at 0.06 liter/hr, respectively (the acrolein concentration of the reaction system consisting of the above-mentioned two different solutions was about 33% by weight), while introducing air to the reactor so that the oxygen concentration at the outlet of the reactor became 4.0% by volume (which is equivalent to the oxygen partial pressure of 0.20 kg/cm$^2$), to thereby effect a reaction for producing methyl acrylate (MA). The reaction was conducted at a temperature of 80° C. under a pressure of 5 kg/cm$^2$. The concentration of NaOH in the above-mentioned methanol solution of NaOH was controlled so that the reaction system had a pH of 7.1. The reaction mixture obtained by the above reaction was continuously withdrawn by overflowing from the outlet of the reactor. Analysis was made with respect to the reaction mixture which was withdrawn from the outlet of the reactor 10 hours after the start of the reaction. As a result, it was found that the conversion of acrolein was 58.3%, the selectivity for MA was 88.8%, and the selectivity for ethylene as a by-product was 2.6%, and that methyl formate was by-produced in an amount of 0.035 mol/mol of MA.

EXAMPLE 56

Substantially the same procedure for activating the catalyst intermediate as in Example 49 was repeated, except that the activation was conducted for 30 hours. The resultant activated catalyst had a Pd/Pb atomic ratio of 3/0.95 and exhibited a maximum intensity peak at a diffraction angle (2θ) of 38.682° in the powder X-ray diffraction pattern thereof, and the ratio of the total intensity of two peaks ascribed to metallic palladium 3d electrons to the intensity of a peak ascribed to metallic lead 4f(7/2) electron which is multiplied by 1.75 in the X-ray photoelectron spectrum of the activated catalyst was 1/0.183.

Using 240 g of the activated catalyst, a reaction for producing MMA was conducted in substantially the same manner as in Example 49. Analysis was made with respect to the reaction mixture which was withdrawn from the outlet of the reactor 10 hours after the start of the reaction. As a result, it was found that the conversion of methacrolein was 57.3%, the selectivity for MMA was 87.9%, and the selectivity for propylene as a by-product was 3.1%, and that methyl formate was by-produced in an amount of 0.031 mol/mol of MMA.

EXAMPLE 57

300 g of the catalyst intermediate prepared in Referential Example 1 was charged in a stainless, external circulation type bubble column reactor, which was equipped with a separator for a catalyst and had a volume of 1.2 liters for a liquid phase. An activation treatment of the catalyst intermediate was conducted as follows. A 36.7% by weight solution of methacrolein in methanol, in which lead acetate had been dissolved so that the lead concentration of the resultant reaction system became 100 ppm by weight, and a 2 to 4% by weight solution of NaOH in methanol were continuously fed to the reactor at 0.54 liter/hr and at 0.06 liter/hr, respectively (the methacrolein concentration of the reaction system consisting of the above-mentioned two different solutions was about 33% by weight), while introducing air to the reactor so that the oxygen concentration at the outlet of the reactor became 3.5% by volume (which is equivalent to the oxygen partial pressure of 0.175 kg/cm$^2$), thereby effecting an activation of the catalyst intermediate. The reaction was conducted at a temperature of 80° C. under a pressure of 5 kg/cm$^2$. The concentration of NaOH in the above-mentioned methanol solution of NaOH was controlled so that the reaction system had a pH of 7.1. The reaction mixture obtained by the above reaction was continuously withdrawn by overflowing from the outlet of the reactor. The reaction was conducted for 50 hours. The resultant activated catalyst had a Pd/Pb atomic ratio of 3/1.09 and exhibited a maximum intensity peak at a diffraction angle (2θ) of 38.634° in the powder X-ray diffraction pattern thereof, and the ratio of the total intensity of two peaks ascribed to metallic palladium 3d electrons to the intensity of a peak ascribed to metallic lead 4f(7/2) electron which is multiplied by 1.75 in the X-ray photoelectron spectrum of the activated catalyst was 1/0.597.

240 g of the activated catalyst was charged in a stainless, external circulation type bubble column reactor, which was equipped with a separator for a catalyst and had a volume of 1.2 liters for a liquid phase. A 36.7% by weight solution of methacrolein in methanol and a 2 to 4% by weight solution of NaOH in methanol were continuously fed to the reactor at 0.54 liter/hr and at 0.06 liter/hr, respectively (the methacrolein concentration of the reaction system consisting of the above-mentioned two different solutions was about 33% by weight), while introducing air to the reactor so that the oxygen concentration at the outlet of the reactor became 4.0% by volume (which is equivalent to the oxygen partial pressure of 0.20 kg/cm$^2$), to thereby effect a reaction for producing MMA. The reaction was conducted at 80° C. under a pressure of 5 kg/cm$^2$. The concentration of NaOH in the above-mentioned methanol solution of NaOH was controlled so that the reaction system had a pH of 7.1. The reaction mixture obtained by the above reaction was continuously withdrawn by overflowing from the outlet of the reactor. Analysis was made with respect to the reaction mixture which was withdrawn from the outlet of the reactor 10 hours after the start of the reaction. As a result, it was found that the conversion of methacrolein was 60.8%, the selectivity for MMA was 91.2 A, and the selectivity for propylene as a by-product was 1.4%, and that methyl formate was by-produced in an amount of 0.062 mol/mol of MMA.

Comparative Example 14

The catalyst intermediate prepared in Referential Example 1 was subjected to treatment for activating a catalyst intermediate in substantially the same manner as in Example 1, except that the activation treatment was conducted under a pressure of 8.3 kg/cm$^2$ and that the oxygen concentration at the outlet of the reactor was increased to 6.0% by volume (which is equivalent to the oxygen partial pressure of 0.50 kg/cm$^2$), so that activation of the catalyst intermediate was not sufficiently effected. After that period of time, the resultant catalyst intermediate was analyzed by the methods as mentioned above. As a result, it was found that the catalyst intermediate had a Pd/Pb atomic ratio of 3/1.03 and exhibited a maximum intensity peak at a diffraction angle (2θ) of 38.739° in the powder X-ray diffraction pattern thereof, and that the ratio of the total intensity of two peaks ascribed to metallic palladium 3d electrons to the intensity of a peak ascribed to metallic lead 4f(7/2) electron which is multiplied by 1.75 in the X-ray photoelectron spectrum of the catalyst intermediate was 1/0.453.

Using the catalyst intermediate, a reaction for producing MMA was conducted in substantially the same manner as in Example 57. 10 Hours after the start of the reaction, the reaction mixture withdrawn from the outlet of the reactor was analyzed. As a result, it was found that the conversion of methacrolein was 60.2%, the selectivity for MMA was 87.4 A, and the selectivity for propylene as a by-product was 4.3%, and that methyl formate was by-produced in an amount of 0.072 mol/mol of MMA.

EXAMPLE 58

An agitation type reactor which had a volume of 6 liters for a liquid phase was charged with 1 kg of the catalyst intermediate prepared in Referential Example 2 and 5 liters of a solution of 20.9 g of lead acetate trihydrate in methanol, in which the amount of lead acetate corresponds to a supplementary lead amount necessary for changing the Pd/Pb atomic ratio (3/0.98) of the catalyst intermediate to 3/1.3. An activation of the catalyst intermediate was conducted at a temperature of 90° C. under a pressure of 5 kg/cm$^2$, while introducing air to the reactor so that the oxygen concentration at the outlet of the reactor became 2.0% by volume (which is equivalent to the oxygen partial pressure of 0.10 kg/cm$^2$). 20 Hours after the start of the reaction, the resultant activated catalyst was analyzed by the methods as mentioned above. As a result, it was found that the activated catalyst had a Pd/Pb atomic ratio of 3/1.27 and exhibited a maximum intensity peak at a diffraction angle (2θ) of 38.691° in the powder X-ray diffraction pattern thereof, and that the ratio of the total intensity of two peaks ascribed to metallic palladium 3d electrons to the intensity of a peak ascribed to metallic lead 4f(7/2) electron which is multiplied by 1.75 in the X-ray photoelectron spectrum of the activated catalyst was 1/0.763.

200 g of the activated catalyst was charged in an agitation type reactor which had the same volume for a liquid phase as that of the bubble column reactor as used in Example 57. A 36.7% by weight solution of methacrolein in methanol and a 2 to 4% by weight solution of NaOH in methanol were continuously fed to the reactor at 0.54 liter/hr and at 0.06 liter/hr, respectively (the methacrolein concentration of the reaction system consisting of the above-mentioned two different solutions was about 33% by weight), while introducing air to the reactor so that the oxygen concentration at the outlet of the reactor became 4.0% by volume (which is equivalent to the oxygen partial pressure of 0.20 kg/cm$^2$), thereby effecting a reaction for producing MMA. The reaction was conducted at a temperature of 80° C. under a pressure of 5 kg/cm$^2$. The concentration of NaOH in the above-mentioned methanol solution of NaOH was controlled so that the reaction system had a pH of 7.1. The reaction mixture obtained by the above reaction was withdrawn by overflowing from the outlet of the reactor. Analysis was made with respect to the reaction mixture which was withdrawn from the outlet of the reactor 10 hours after the start of the reaction. As a result, it was found that the conversion of methacrolein was 57.8%, the selectivity for MMA was 89.9%, and the selectivity for propylene as a by-product was 2.12%, and that methyl formate was by-produced in an amount of 0.103 mol/mol of MMA.

EXAMPLE 59

Substantially the same procedure as in Referential Example 1 was repeated, except that the amount of the aqueous solution of lead nitrate added to the carrier was changed so that the amount of lead nitrate contained in the resultant mixture became 4.2 parts by weight, relative to 100 parts by weight of the carrier, to thereby obtain a composition (Pd$^{5.0}$Pb$^{4.2}$/SiO$_2$—Al$_2$O$_3$—MgO) (hereinafter, frequently referred to as "catalyst intermediate"). The obtained catalyst intermediate had a Pd/Pb atomic ratio of 3/1.29 and exhibited a maximum intensity peak at a diffraction angle (2θ) of 38.913° in the powder X-ray diffraction pattern thereof, and the ratio of the total intensity of two peaks ascribed to metallic palladium 3d electrons to the intensity of a peak ascribed to metallic lead 4f(7/2) electron which is multiplied by 1.75 in the X-ray photoelectron spectrum of the catalyst intermediate was 1/0.187.

2 kg of the catalyst intermediate and an acetic acid solution in methanol, which had been obtained by dissolving 2.5 kg of acetic acid in 25 kg of methanol, were charged in a 30-liter autoclave, and stirred at 90° C. for 1 hour. The resultant mixture was analyzed, and found to contain lead ions in a concentration of 720 ppm by weight. Thereafter, an activation of the catalyst intermediate was effected, while introducing air to the reactor so that the oxygen concentration at the outlet of the reactor became 2.0% by volume (which is equivalent to the oxygen partial pressure of 0.10 kg/cm$^2$). The activation was conducted at a temperature of 90° C. under a pressure of 5 kg/cm$^2$ for 50 hours. The resultant activated catalyst had a Pd/Pb atomic ratio of 3/1.27 and exhibited a maximum intensity peak at a diffraction angle (2θ) of 38.685° in the powder X-ray diffraction pattern thereof, and the ratio of the total intensity of two peaks ascribed to metallic palladium 3d electrons to the intensity of a peak ascribed to metallic lead 4f(7/2) electron which is multiplied by 1.75 in the X-ray photoelectron spectrum was 1/0.65.

Two stainless, external circulation type bubble column reactors as used in Example 57, each of which was equipped with a separator for a catalyst and had a volume of 1.2 liters for a liquid phase, were connected to provide a first stage reactor and a second stage reactor which were connected in series. Each of the first stage and second stage reactors was charged with 240 g of the activated catalyst. Then, a series of reactions for producing MMA was conducted as follows. A 36.7% by weight solution of methacrolein in methanol, in which lead acetate had been dissolved so that the lead concentration of the resultant reaction system became 20 ppm by weight, and a 2 to 4% by weight solution of NaOH in methanol were continuously fed to the first stage reactor at 0.54 liter/hr and at 0.06 liter/hr, respectively (the methacrolein concentration of the reaction system consisting of the above-mentioned two different solutions was about 33% by weight), while introducing air to the first stage reactor so that the oxygen concentration at the outlet of the first stage reactor became 4.0% by volume (which is equivalent to the oxygen partial pressure of 0.20 kg/cm$^2$), to effect a reaction for producing MMA. The reaction was conducted at a temperature of 80° C. under a pressure of 5 kg/cm$^2$. The resultant reaction mixture containing the catalyst was continuously withdrawn by overflowing from the outlet of the first stage reactor and transferred to a liquid phase-solid phase separation zone, where a separation between the catalyst and the reaction mixture was effected. The separated catalyst was returned to the first stage reactor. The separated reaction mixture and a 2 to 4% by weight solution of NaOH in methanol were fed to the second stage reactor at 0.6 liter/hr and at 0.06 liter/hr, respectively. A gaseous phase withdrawn from the first stage reactor was fed to the second stage reactor while introducing fresh air to the second stage reactor so that the oxygen concentration at the outlet of the second stage reactor became 2.2% by volume (which is equivalent to the oxygen partial pressure of 0.11 kg/cm$^2$), to effect a reaction for producing MMA. The reaction was conducted at a temperature of 80° C. under a pressure of 4.6 kg/cm$^2$. The concentration of NaOH in the methanol solution fed to each of the first stage and second stage reactors was controlled so that the reaction system in each reactor had a pH of 7.1. The reaction mixture obtained in the second stage reactor was continuously withdrawn by overflowing from the outlet of the second stage reactor. Analysis was made with respect to the reaction mixture which was withdrawn from the outlet of the second stage reactor 10 hours after the start of the two-stage reaction. As a result, it was found that the conversion of methacrolein was 84.7%, the selectivity for MMA was 90.1%, and the selectivity for propylene as a by-product was 2.4%, and that methyl formate was by-produced in an amount of 0.073 mol/mol of MMA.

EXAMPLE 60

1 kg of the catalyst intermediate prepared in Referential Example 1 was charged in an agitation type reactor which had a volume of 6 liters for a liquid phase. An activation of the catalyst intermediate was conducted as follows. A 36.7% by weight solution of methacrolein in methanol and a 30% by weight solution of sodium acetate trihydrate in methanol were continuously fed to the reactor at 0.54 liter/hr and at 0.06 liter/hr, respectively (the methacrolein concentration and the concentration of sodium acetate trihydrate in the reaction system consisting of the above-mentioned two different solutions were about 33% by weight and about 3% by weight, respectively), while introducing air to the reactor so that the oxygen concentration at the outlet of the reactor became 2.0% by volume (which is equivalent to the oxygen partial pressure of 0.10 kg/cm$^2$), to effect an activation of the catalyst intermediate. The activation was conducted at a temperature of 90° C. under a pressure of 5 kg/cm$^2$ for 50 hours. The resultant activated catalyst was analyzed, and it was found that the activated catalyst had a Pd/Pb atomic ratio of 3/1.10, and exhibited a maximum intensity peak at a diffraction angle (2θ) of 38.632° in the powder X-ray diffraction pattern thereof, and that the ratio of the total intensity of two peaks ascribed to metallic palladium 3d electrons to the intensity of a peak ascribed to metallic lead 4f(7/2) electron which is multiplied by 1.75 in the X-ray photoelectron spectrum was 1/0.614.

Using the activated catalyst, a reaction for producing MMA was conducted in substantially the same manner as in Example 57. Analysis was made with respect to the reaction mixture which was withdrawn from the outlet of the reactor 10 hours after the start of the reaction. As a result, it was found that the conversion of methacrolein was 59.8%, the selectivity for MMA was 90.9%, and the selectivity for propylene as a by-product was 1.4%, and that methyl formate was by-produced in an amount of 0.053 mol/mol of MMA.

EXAMPLES 61 to 63

In Examples 61 to 63, the catalyst intermediates prepared in Referential Example 1 were individually subjected to activation treatment and, using the resultant activated catalysts, MMA-producing reactions were individually conducted in substantially the same manner as in Example 60, except that the conditions for the activation were changed as indicated in Table 6. The Pd/Pb atomic ratio of the activated catalyst, the diffraction angle (2θ) for a maximum intensity peak in the powder X-ray diffraction pattern of the activated catalyst, and the ratio of the total intensity of two peaks ascribed to metallic palladium 3d electrons to the intensity of a peak ascribed to metallic lead 4f(7/2) electron which is multiplied by 1.75 in the X-ray photoelectron spectrum of the activated catalyst in each of Examples 61 to 63 are shown in Table 6, together with the respective results of the analyses of the reaction mixtures obtained 10 hours after the start of the MMA producing reactions.

TABLE 6

| | | Conditions for activation | | | | | | Activated catalyst | | | Selectivity for carboxylic ester (%) | Selectivity for by-product (%) | Amount of methyl formate produce (mol/mol of MMA) |
|---|---|---|---|---|---|---|---|---|---|---|---|---|---|
| | | Aldehyde (% by weight) (*1) | Additional lead (ppm) (*2) | Oxygen partial pressure (kg/cm$^2$) | Fatty acid | | Temperature (° C.) | Pd/Pb atomic ratio | Diffraction angle (2θ) for maximum intensity peak | Intensity ratio of peaks (metallic Pd/metallic Pb) | Conversion of aldehyde (%) | | | |
| Examples | Aldehyde/alcohol | | | | Type | Amount (% by weight) (*1) | | | | | | | | |
| Example 61 | benzaldehyde/methanol | 33 | — | 0.15 | acetic acid | 3 | 90 | 3/1.19 | 38.662° | 1/0.54 | 60.7 | 90.5 (for methyl benzoate) | 1.7 (for benzene) | 0.071 |
| Example 62 | acrolein/methanol | 33 | 50 | 0.20 | magnesium acetate | 3 | 90 | 3/1.08 | 38.673° | 1/0.43 | 59.5 | 90.9 (for methyl acrylate) | 1.6 (for ethylene) | 0.043 |
| Example 63 | isobutyl aldehyde/methanol | 33 | 50 | 0.15 | sodium acetate | 3 | 90 | 3/1.21 | 38.654° | 1/0.56 | 61.9 | 89.7 (for methyl isobutyrate) | 1.6 (for propane) | 0.063 |

Note:
*1) The amounts of aldehyde, additional lead and fatty acid are expressed in terms of the concentrations in the reaction system.
*2) Lead acetate trihydrate was used as the source of the additional lead.

EXAMPLE 64

A catalyst intermediate (Pd$^{5.0}$Pb$^{3.96}$Tl$^{0.11}$/SiO$_2$) was obtained in the same manner as Example 36. The obtained catalyst intermediate was subjected to activation treatment in substantially the same manner as in Example 58, except that air was introduced to the reactor so that the oxygen concentration at the outlet of the reactor became 3.0% by volume (which is equivalent to the oxygen partial pressure of 0.15 kg/cm$^2$). The resultant activated catalyst had a Pd/Pb atomic ratio of 3/1.20, and exhibited a maximum intensity peak at a diffraction angle (2θ) of 38.682° in the powder X-ray diffraction pattern thereof, and the ratio of the total intensity of two peaks ascribed to metallic palladium 3d electrons to the intensity of a peak ascribed to metallic lead 4f(7/2) electron which is multiplied by 1.75 in the X-ray photoelectron spectrum of the activated catalyst was 1/0.643.

200 g of the activated catalyst was charged in an agitation type reactor which had the same volume for a liquid phase as that of the bubble column reactor as used in Example 57, and a reaction for producing MMA was performed in substantially the same manner as in Example 57, except that lead acetate was dissolved in the solution of methacrolein in methanol so that the lead concentration of the reaction system became 100 ppm by weight. Analysis was made with respect to the reaction mixture which was withdrawn from the outlet of the reactor 10 hours after the start of the reaction. As a result, it was found that the conversion of methacrolein was 62.1%, the selectivity for MMA was 90.42%, and the selectivity for propylene as a by-product was 1.77%, and that methyl formate was by-produced in an amount of 0.085 mol/mol of MMA.

EXAMPLE 65

With respect to the catalyst intermediate prepared in Example 37, an activation treatment was conducted in substantially the same manner as described in Example 64. The resultant activated catalyst was analyzed with respect to the Pd/Pb atomic ratio thereof, the diffraction angle (2θ) in the powder X-ray diffraction pattern thereof at which the maximum intensity peak was exhibited, and the ratio of the total intensity of two peaks ascribed to metallic palladium 3d electrons to the intensity of a peak ascribed to metallic lead 4f(7/2) electron which is multiplied by 1.75 in the X-ray photoelectron spectrum thereof, by the methods as mentioned above. As a result, it was found that the catalyst had a Pd/Pb atomic ratio of 3/1.24 and exhibited a maximum intensity peak at a diffraction angle (2θ) of 38.6730, and that the ratio of the total intensity of two peaks ascribed to metallic palladium 3d electrons to the intensity of a peak ascribed to metallic lead 4f(7/2) electron which is multiplied by 1.75 was 1/0.595.

Substantially the same procedure for producing MMA as in Example 64 was repeated, and the reaction mixture obtained 10 hours after the start of the reaction was analyzed. As a result, it was found that the conversion of methacrolein was 60.4%, the selectivity for MMA was 90.5%, and the selectivity for propylene as a by-product was 1.96% and that methyl formate was by-produced in an amount of 0.075 mol/mol of MMA.

EXAMPLE 66

Substantially the same procedure for producing MMA as described in Example 64 was repeated, except that the activated catalyst obtained in Example 62 was used, and that acrolein was used instead of the methacrolein. The reaction mixture obtained 10 hours after the start of the reaction was analyzed. As a result, it was found that the conversion of acrolein was 59.3%, the selectivity for methyl acrylate (MA) was 90.1%, and the selectivity for ethylene as a by-product was 1.83%, and that methyl formate was by-produced in an amount of 0.086 mol/mol of MA.

EXAMPLE 67

The catalyst intermediate prepared in Referential Example 1 was activated in substantially the same manner as described in Example 60, except that air was not fed to the reactor, to thereby obtain an activated catalyst. The activated catalyst was analyzed by the methods as mentioned above. As a result, it was found that the activated catalyst had a Pd/Pb atomic ratio of 3/1.28 and exhibited a maximum intensity peak at a diffraction angle (2θ) of 38.675° in the powder X-ray diffraction pattern thereof, and that the ratio of the total intensity of two peaks ascribed to metallic palladium 3d electrons to the intensity of a peak ascribed to metallic lead 4f(7/2) electron which is multiplied by 1.75 in the X-ray photoelectron spectrum of the activated catalyst was 1/0.914.

Substantially the same procedure for producing MMA as in Example 58 was repeated, except that the above-obtained activated catalyst was used. The reaction mixture obtained 10 hours after the start of the reaction was analyzed. As a result, it was found that the conversion of methacrolein was 56.3%, the selectivity for MMA was 90.2%. and the selectivity for propylene as a by-product was 1.95%, and that methyl formate was by-produced in an amount of 0.132 mol/mol of MMA.

Referential Example 8

A stainless container which had a volume of 40 liters was charged with 10 kg of an aqueous silica sol {Snowtex N-30 ($SiO_2$ content: 30% by weight), manufactured and sold by Nissan Chemical Industries, Ltd., Japan}. The silica sol was stirred, and 2.05 kg of aluminum nitrate nonahydrate was gradually added to the silica sol with stirring, to completely dissolve the aluminum nitrate nonahydrate in the silica sol. The resultant solution was subjected to spray drying by means of a spray dryer at 130° C., thereby obtaining a solid substance. The obtained solid substance was spread over the bottom of a stainless container (having its top opened) in a thickness of about 1 cm. The container was placed in an electric furnace. The temperature of the container was elevated to 300° C. over 2 hours and maintained at 300° C. for 3 hours and then, further elevated to 600° C. over 2 hours and maintained at 600° C. for 3 hours to effect a calcination of the solid substance. Thereafter, the container was gradually cooled to thereby obtain a carrier. The Al/(Al+Si) proportion of the obtained carrier was 10 mol %, and the specific surface area of the carrier was 145 m$^2$/g as measured by the BET nitrogen adsorption method. The carrier was observed by means of a microscope. As a result, it was found that the carrier was almost spherical, and had an average particle diameter of 60 μm. From the results of the grindability test of the carrier as evaluated using a mortar, it was found that the obtained carrier was harder than a commercially available silica gel.

The water resistance of the carrier was evaluated in accordance with the accelerated test as mentioned above. As a result, the carrier was found to have a water resistance such that the concentration of Si ions dissolved out in water by hydrolysis was only 40 ppm.

Comparative Referential Example 1

Substantially the same procedure as in Referential Example 8 was repeated, except that the aluminum nitrate was not added to the silica sol, thereby obtaining a carrier having a specific surface area of 188 m$^2$/g. The water resistance of the obtained carrier was evaluated in accordance with the accelerated test as mentioned above. As a result, the carrier was found to have a water resistance such that the concentration of Si ions dissolved out in water by hydrolysis was 210 ppm.

Comparative Referential Example 2

A commercially available silica gel (Cariact 10, manufactured and sold by Fuji Silysia Chemical, Ltd., Japan) was calcined at 600° C. for 3 hours. The specific surface area of the obtained silica was 300 m$^2$/g as measured by the BET nitrogen adsorption method. The water resistance of the obtained silica was evaluated in accordance with the accelerated test as mentioned above. As a result, the carrier was found to have a water resistance such that the concentration of Si ions dissolved out in water by hydrolysis was 244 ppm.

Referential Example 9

Substantially the same procedure as in Referential Example 8 was repeated, except that the aluminum nitrate nonahydrate was added to the silica sol so that the aluminum proportion became 5 mol %, based on the total molar amount of silicon and aluminum, and that the temperature for calcination was changed to 750° C., to thereby obtaining a carrier having a specific surface area of 53 m$^2$/g. The water resistance of the obtained carrier was evaluated in accordance with the accelerated test as mentioned above. As a result, the carrier was found to have a water resistance such that the concentration of Si ions dissolved out in water by hydrolysis was only 90 ppm.

Referential Example 10

Substantially the same procedure as in Referential Example 8 was repeated, except that the aluminum nitrate and magnesium nitrate were added to the silica sol so that the aluminum proportion and the magnesium proportion became 20 mol % and 5 mol %, respectively, based on the total molar amount of silicon, aluminum and magnesium. Thus, a carrier having a specific surface area of 123 m$^2$/g was obtained. The water resistance of the obtained carrier was evaluated in accordance with the accelerated test as mentioned above. As a result, the carrier was found to have a water resistance such that the concentration of Si ions dissolved out in water by hydrolysis was only 35 ppm.

Referential Example 11

Substantially the same procedure as in Referential Example 8 was repeated, except that aluminum nitrate and sodium acetate were added to the silica sol so that the aluminum proportion and the sodium proportion became 30 mol % and 1 mol %, respectively, based on the total molar amount of silicon, aluminum and sodium. Thus, a carrier having a specific surface area of 98 m$^2$/g was obtained. The obtained water resistance of the carrier was evaluated in accordance with the accelerated test as mentioned above. As a result, the carrier was found to have a water resistance such that the concentration of Si ions dissolved out in water by hydrolysis was only 43 ppm.

Referential Example 12

A commercially available silica-alumina composition {N631HN, wherein the Al/(Al+Si) proportion was 10 mol %, manufactured and sold by NIKKI Chemical Co., Ltd., Japan} was spread over the bottom of a stainless container (having its top opened) in a thickness of about 1 cm. The container was placed in an electric furnace. The temperature of the container was elevated to 300° C. over 2 hours and maintained at 300° C. for 3 hours and then, further elevated to 800° C. over 2 hours and maintained at 800° C. for 3 hours to effect a calcination of the silica alumina compound. Thereafter, the container was gradually cooled to thereby obtain a carrier. The specific surface area of the carrier was 348 m$^2$/g as measured by the BET nitrogen adsorption method. The water resistance of the obtained carrier was evaluated in accordance with the accelerated test as mentioned above. As a result, the carrier was found to have a water resistance such that the concentration of Si ions dissolved out in water by hydrolysis was only 87 ppm.

Referential Example 13

Substantially the same procedure as in Referential Example 12 was repeated, except that another commercially available silica-alumina composition {N631HN, wherein the Al/(Al+Si) proportion was 15 mol %, manufactured and sold by NIKKI Chemical Co., Ltd., Japan} was used, thereby obtaining a carrier. The specific surface area of the obtained carrier was 346 m$^2$/g as measured by the BET nitrogen adsorption method. The water resistance of the obtained carrier was evaluated in accordance with the accelerated test as mentioned above. As a result, the carrier was found to have a water resistance such that the concentration of Si ions dissolved out in water by hydrolysis was only 98 ppm.

Referential Example 14

A beaker having a volume of 2 liters was charged with 150 g of a commercially available silica gel (Cariact 10, manufactured and sold by Fuji Silysia Chemical, Ltd., Japan) and 200 ml of distilled water, thereby obtaining an aqueous silica sol. 97.1 g of aluminum nitrate nonahydrate was gradually dissolved in the obtained aqueous silica sol. The resultant solution was evaporated on a boiling water bath. The resultant solid substance was spread over the bottom of a stainless container (having its top opened) in a thickness of about 1 cm. The container was placed in an electric furnace. The temperature of the container was elevated to 300° C. over 2 hours, and maintained at 300° C. for 3 hours and then, further elevated to 600° C. over 2 hours and maintained at 600° C. for 3 hours to effect a calcination of the solid substance. Thereafter, the container was gradually cooled. The cooled substance was washed 3 times with hot water (60° C.), and dried at 110° C. for 12 hours, thereby obtaining a carrier. The Al/(Al+Si) proportion of the obtained carrier was 4.5 mol %, and the specific surface area of the obtained carrier was 183 m$^2$/g as measured by the BET nitrogen adsorption method. The water resistance of the carrier was evaluated in accordance with the accelerated test as mentioned above. As a result, the carrier was found to have a water resistance such that the concentration of Si ions dissolved out in water by hydrolysis was only 82 ppm.

The Al/(Al+Si) proportions, the specific surface areas, and the concentrations of Si ions dissolved out in water by hydrolysis measured in Referential Examples 8 to 14 and Comparative Referential Examples 1 and 2 are shown in Table 7, together with the materials for the respective carriers and the temperatures for calcination.

TABLE 7

| Referential Examples and Comparative Referential Examples | Materials for carrier | | Temperature for calcination (° C.) | Al/(Al + Si) proportion (mol %) | Specific surface area (m$^2$/g) | Water resistance: [concentration of Si ion (ppm)] |
|---|---|---|---|---|---|---|
| | Source of silica | Source of alumina, other materials | | | | |
| Referential Example 8 | silica sol | aluminum nitrate | 600 | 10 | 145 | 40 |

TABLE 7-continued

| Referential Examples and Comparative Referential Examples | Materials for carrier | | Temperature for calcination (° C.) | Al/(Al + Si) proportion (mol %) | Specific surface area (m²/g) | Water resistance: [concentration of Si ion (ppm)] |
|---|---|---|---|---|---|---|
| | Source of silica | Source of alumina, other materials | | | | |
| Comparative Referential Example 1 | silica sol | — | 600 | 0 | 188 | 210 |
| Comparative Referential Example 2 | silica gel (Cariact 10) | — | 600 | 0 | 300 | 244 |
| Referential Example 9 | silica sol | aluminum nitrate | 750 | 5 | 53 | 90 |
| Referential Example 10 | silica sol | aluminum nitrate, magnesium nitrate | 600 | 20(Al), 5(Mg)*1 | 123 | 35 |
| Referential Example 11 | silica sol | aluminum nitrate, sodium acetate | 600 | 30(Al), 1(Na)*2 | 98 | 43 |
| Referential Example 12 | commercially available silica-alumina N631HN | | 800 | 30 | 348 | 87 |
| Referential Example 13 | commercially available silica-alumina N632L | | 800 | 15 | 346 | 98 |
| Referential Example 14 | silica gel (Cariact 10) | aluminum nitrate | 600 | 4.5 | 183 | 82 |

Note:
*1) Mg/(Mg + Si) proportion (mol %)
*2) Na/(Na + Si) proportion (mol %)

EXAMPLE 68

Substantially the same procedure for producing MMA as in Example 20 (in which use was made of an activated catalyst containing an $SiO_2$—$Al_2O_3$—MgO carrier) was conducted, except that the reaction for producing MMA was performed for 1000 hours.

Analysis was made with respect to the reaction mixtures which were withdrawn from the outlet of the first stage and second stage reactors 500 hours and 1000 hours after the start of the reaction. Each of the reaction mixtures was analyzed by ICP. As a result, it was found that no Pd ions were detected (that is, the concentration of Pd ions were below the detection limit) in each of the reaction mixtures, and that each of the concentrations of Si ions and Al ions was 1 ppm or less. After completion of the 1000-hour reaction, a portion of the catalyst was taken out from each of the first stage and second stage reactors, and observed under a scanning electron microscope (SEM). As a result, either cracking or chipping was hardly observed in each of the catalysts taken out from both of the first stage and second stage reactors.

Comparative Example 15

Substantially the same procedure for producing MMA as in Example 20 was conducted, except that the same catalyst (which contains an $SiO_2$ carrier) as used in Example 2 was used. Analysis was made with respect to the reaction mixture which was withdrawn from the outlet of the first stage reactor 1000 hours after the start of the reaction. As a result, it was found that the conversion of methacrolein was 55.1%, the selectivity for MMA was 90.2%, and the selectivity for propylene as a by-product was 1.51% and that methyl formate was by-produced in an amount of 0.046 mol/mol of MMA. Also, each of the reaction mixtures which were withdrawn from the outlet of the first stage and second stage reactors 1000 hours after the start of the reaction was analyzed by ICP. As a result, it was found that Pd ions were detected in the reaction mixtures from the first stage and second stage reactors in concentrations of 0.3 ppm and 0.5 ppm, respectively, and Si ions were detected in the reaction mixtures from the first stage and second stage reactors in concentrations of 8 ppm and 12 ppm, respectively. After completion of the 1000-hour reaction, a portion of the catalyst was taken out from each of the first stage and second stage reactors, and observed under SEM. As a result, cracking and chipping were observed in some portions of both of the catalysts obtained from the first stage and second stage reactors.

Comparative Example 16

Substantially the same procedure for producing MMA as in Example 20 was conducted, except that the same catalyst (which contains an $Al_2O_3$ carrier) as used in Example 4 was used. Analysis was made with respect to the reaction mixture which was withdrawn from the outlet of the first stage reactor 1000 hours after the start of the reaction. As a result, it was found that the conversion of methacrolein was 65.2%, the selectivity for MMA was 90.7%, and the selectivity for propylene as a by-product was 1.31% and that methyl formate was by-produced in an amount of 0.053 mol/mol of MMA. Also, each of the reaction mixtures which were withdrawn from the outlet of the first stage and second stage reactors 1000 hours after the start of the reaction was analyzed by ICP. As a result, it was found that Pd ions were detected in the reaction mixtures from the first stage and second stage reactors in concentrations of 0.5 ppm and 0.8 ppm, respectively, and Al ions were detected in the reaction mixtures from the first stage and second stage reactors in concentrations of 12 ppm and 18 ppm, respectively. After completion of the 1000-hour reaction, a portion of the catalyst was taken out from each of the first stage and second stage reactors, and observed under SEM. As a result, cracking and chipping were observed in some portions of both of the catalysts obtained from the first stage and second stage reactors.

EXAMPLE 69

Substantially the same procedure for preparing a catalyst intermediate as in Example 36 was repeated, except that the type of the carrier was changed to $Al_2O_3$—$SiO_2$, to thereby obtain a catalyst intermediate ($Pd^{5.0}Pb^{2.76}Tl^{0.11}/Al_2O_3$—$SiO_2$).

The obtained catalyst intermediate was subjected to activation treatment in substantially the same manner as in Example 26. The resultant activated catalyst had a Pd/Pb atomic ratio of 3/1.20 and exhibited a maximum intensity peak at a diffraction angle ($2\theta$) of 38.626°, and the ratio of the total intensity of two peaks ascribed to metallic palladium 3d electrons to the intensity of a peak ascribed to metallic lead 4f(7/2) electron which is multiplied by 1.75 was 1/0.46.

Substantially the same procedure for producing MMA as in Example 42 was repeated using the above-obtained activated catalyst. Analysis was made with respect to the reaction mixture which was withdrawn from the outlet of the reactor 1000 hours after the start of the reaction. As a result, it was found that the conversion of methacrolein was 61.5%, the selectivity for MMA was 90.9%, and the selectivity for propylene as a by-product was 1.16%, and that methyl formate was by-produced in an amount of 0.045 mol/mol of MMA. The reaction mixture was also analyzed by ICP. As a result, it was found that no Pd ions were detected (that is, the concentration of Pd ions was below the detection limit), and that each of the concentrations of Si ion and Al ion was 1 ppm or less. After completion of the 1000-hour reaction, a portion of the catalyst was taken out from the reactor, and observed under SEM. As a result, there was almost no change in the catalyst.

Referential Example 15

3.5 kg of aluminum nitrate nonahydrate, 2.56 kg of magnesium nitrate hexahydrate, 540 g of 60% nitric acid and 4.67 kg of water were charged in a stainless container which had a volume of 50 liters, and mixed with each other. To the resultant mixture was gradually added 20.0 kg of an aqueous silica sol {Snowtex N-30 ($SiO_2$ content: 30% by weight), manufactured and sold by Nissan Chemical Industries, Ltd., Japan} with stirring. After mixing well, the resultant mixture was subjected to spray drying by means of a spray dryer at 130° C., thereby obtaining a solid substance. The obtained solid substance was spread over the bottom of a stainless container (having its top opened) in a thickness of about 1 cm. The container was placed in an electric furnace. The temperature of the container was elevated to 300° C. over 2 hours, and maintained at 300° C. for 3 hours and then, further elevated to 600° C. over 2 hours and maintained at 600° C. for 3 hours. Thereafter, the container was gradually cooled to thereby obtain a carrier. The obtained carrier contained a silica-alumina-magnesia composition having silicon, aluminum and magnesium proportions of 83.3 mol %, 8.4 mol % and 8.3 mol % respectively, based on the total molar amount of silicon, aluminum and magnesium. The specific surface area of the carrier was 148 $m^2$ as measured by the BET nitrogen adsorption method. The carrier was observed by means of a microscope. As a result, it was found that the carrier was almost spherical, and had an average particle diameter of about 60 $\mu$m. From the results of the grindability test of the carrier as evaluated using a mortar, it was found that the obtained carrier was harder than a commercially available silica gel.

The water resistance of the obtained carrier was evaluated in accordance with the accelerated test as mentioned above. As a result, the carrier was found to have a water resistance such that the concentration of Si ions dissolved out in water by hydrolysis was only 42 ppm.

Referential Example 16

Substantially the same procedure as in Referential Example 15 was repeated, except that magnesium nitrate and aluminum nitrate were added to the aqueous silica sol so that the magnesium and aluminum proportions became 4.3 mol % and 13.6 mol %, respectively, based on the total molar amount of the silicon, the aluminum and the magnesium, and that the temperature for calcination was changed to 700° C., to thereby obtain a carrier. The obtained carrier had a specific surface area of 155 $m^2/g$. The water resistance of the obtained carrier was evaluated in accordance with the accelerated test as mentioned above. As a result, the carrier was found to have a water resistance such that the concentration of Si ions dissolved out in water by hydrolysis was only 39 ppm.

Referential Example 17

Substantially the same procedures as in Referential Example 15 was repeated, except that magnesium nitrate and aluminum nitrate were added to the aqueous silica sol so that the magnesium and aluminum proportions became 5.6 mol % and 22.3 mol %, respectively, based on the total molar amount of silicon, aluminum and magnesium, and that the temperature for calcination was changed to 800° C., to thereby obtain a carrier. The obtained carrier had a specific surface area of 138 $m^2/g$. The water resistance of the obtained carrier was evaluated in accordance with the accelerated test as mentioned above. As a result, the carrier was found have a water resistance such that the concentration of Si ions dissolved out in water by hydrolysis was only 40 ppm.

Referential Example 18

Substantially the same procedure as in Example 15 was repeated, except that magnesium nitrate and aluminum nitrate were added to the aqueous silica sol so that the magnesium and aluminum proportions became 17.2 mol % and 36.6 mol %, respectively, based on the total molar amount of silicon, aluminum and magnesium, and that the temperature for calcination was changed to 800° C., to thereby obtain a carrier. The obtained carrier had a specific surface area of 123 $m^2/g$. The water resistance of the obtained carrier was evaluated in accordance with the accelerated test as mentioned above. As a result, the carrier was found to have a water resistance such that the concentration of Si ions dissolved out in water by hydrolysis was only 45 ppm.

Referential Example 19

Sulfuric acid was added to 10 kg of a water glass (sodium silicate) {JIS K1408, No. 3 ($SiO_2$ content: 28 to 30 wt %, $Na_2O$ content: 9 to 10 wt %)} until the pH of the resultant mixture became 9. Then, to the resultant mixture was added $Al_2(SO_4)_3$ until the pH became 2. Further, to the resultant mixture was added sodium aluminate until the pH became 5 to 5.5. The resultant mixture was partially dehydrated to thereby obtain a hydrogel containing about 10% by weight of silica-alumina. The obtained hydrogel was subjected to spray drying by means of a spray dryer at 130° C. to thereby obtain a solid substance. The obtained solid substance was washed with water until the $NaO_2$ content and $SO_4$ content of the resultant slurry became 0.02% or less and 0.5% or less, respectively. The resultant slurry was mixed with 200 g of magnesium oxide, and heated at 80° C. for 3 hours, followed by filtration to obtain a filter cake. The obtained filter cake was dried at 110° C. for 6 hours. The resultant dried substance was heated to a temperature of 700° C. over 3 hours and maintained at 700° C. for 3 hours to thereby calcine the dried substance. The calcined substance was gradually cooled to thereby obtain a carrier. The obtained carrier had the magnesium and aluminum proportions of 6.3 mol % and 14.6 mol %, respectively, based on the total molar amount of silicon, aluminum and magnesium. The specific surface area of the carrier was 223 $m^2/g$ as measured by the BET nitrogen adsorption method. The water resistance of the carrier was evaluated in accordance with the accelerated test as mentioned above. As a result, the carrier

Referential Example 21

Substantially the same procedure as in Referential Example 15 was repeated, except that magnesium nitrate and aluminum nitrate were added to the aqueous silica sol so that the magnesium and aluminum proportions became 38.1 mol % and 15 mol %, respectively, based on the total molar amount of silicon, aluminum and magnesium, and that the temperature for calcination was changed to 800° C., to thereby obtain a carrier. The obtained carrier had a specific surface area of 134 $m^2/g$. The water resistance of the obtained carrier was evaluated in accordance with the accelerated test as mentioned above. As a result, the carrier was found to have a water resistance such that the concentration of Si ions dissolved out in water by hydrolysis was only 43 ppm.

The composition and specific surface area of the carrier, the temperature for calcination, and the concentration of Si ions dissolved out from the carrier in water by hydrolysis in each of Referential Examples 15 to 21 are shown in Table 8.

TABLE 8

| Referential Examples | Materials for carrier | | | Temperature for calcination (° C.) | Silicon (mol %) | Aluminum (mol %) | Magnesium (mol %) | Specific surface area ($m^2/g$) | Water resistance: [concentration of Si ion (ppm)] |
|---|---|---|---|---|---|---|---|---|---|
| | Source of silica | Source of alumina | Source of magnesia | | | | | | |
| Referential Example 15 | silica sol | aluminum nitrate | magnesium nitrate | 600 | 83.3 | 8.4 | 8.3 | 148 | 42 |
| Referential Example 16 | silica sol | aluminum nitrate | magnesium nitrate | 700 | 82.1 | 13.6 | 4.3 | 155 | 39 |
| Referential Example 17 | silica sol | aluminum nitrate | magnesium nitrate | 800 | 72.1 | 22.3 | 5.6 | 138 | 40 |
| Referential Example 18 | silica sol | aluminum nitrate | magnesium nitrate | 800 | 46.2 | 36.6 | 17.2 | 123 | 45 |
| Referential Example 19 | water-glass | aluminum sulfate, sodium aluminate | magnesium oxide | 700 | 79.1 | 14.6 | 6.3 | 223 | 88 |
| Referential Example 20 | silica sol | aluminum nitrate | magnesium hydroxide | 600 | 82.6 | 10.2 | 7.2 | 123 | 48 |
| Referential Example 21 | silica sol | aluminum nitrate | magnesium nitrate | 650 | 46.9 | 15 | 38.1 | 134 | 43 | was found to have a water resistance such that the concentration of Si ions dissolved out in water by hydrolysis was only 88 ppm.

Referential Example 20

Substantially the same procedure as in Referential Example 15 was repeated, except that magnesium hydroxide and aluminum nitrate were added to the aqueous silica sol so that the magnesium and aluminum proportions became 7.2 mol % and 10.2 mol %, respectively, based on the total molar amount of silicon, aluminum and magnesium, and that the temperature for calcination was changed to 600° C., to thereby obtain a carrier. The obtained carrier had a specific surface area of 123 $m^2/g$. The water resistance of the obtained carrier was evaluated in accordance with the accelerated test as mentioned above. As a result, the carrier was found to have a water resistance such that the concentration of Si ions dissolved out in water by hydrolysis was only 48 ppm.

Referential Example 22

128 g of a water glass (sodium silicate) {JIS K1408, No. 3 ($SiO_2$ content: 28 to 30% by weight, $Na_2O$ content: 9 to 10% by weight)} was dissolved in 120 g of water to thereby obtain a solution (this solution is referred to as "solution A"). 3.9 g of aluminum sulfate octadecahydrate and 4 g of sulfuric acid were dissolved in 40 g of water to thereby obtain a solution (this solution is referred to as "solution B"). 20 g of 1,3-dimethyl urea was dissolved in 80 g of water to thereby obtain a solution (this solution is referred to as "solution C"). Solutions B and C were mixed with solution A while vigorously agitating solution A using a homogenizer, and the agitation was conducted for 1 hour to thereby obtain a gel. The obtained gel was heated at 150° C. for 40 hours while agitating at a circumferential speed of 2 m/sec, to thereby crystallize the gel.

The resultant crystallized substance was subjected to filtration, followed by washing with water. The washed substance was dried at 120° C. for 5 hours, and calcined in air at 500° C. for 5 hours to thereby remove organic substances. Subsequently, the calcined substance was subjected to ion exchange in an aqueous 1N nitric acid solution for 8 hours, and subjected to filtration, followed by washing with water. The washed substance was dried at 120° C. for 6 hours to thereby obtain a crystalline aluminosilicate in a proton form.

The obtained crystalline aluminosilicate was analyzed with respect to the X-ray diffraction pattern thereof and, as a result, it was identified as ZSM-5 zeolite. Also, the crystalline aluminosilicate was subjected to X-ray fluorescence analysis, and the acid content thereof was measured by the pyridine adsorption method. From the results of the X-ray fluorescence analysis and the measured acid content, it was found that the crystalline aluminosilicate in an oxidized form thereof had a composition represented by the following formula: $0.32H_2O.10SiO_2.Al_{2/3}O$.

The water resistance of the crystalline aluminosilicate was evaluated in accordance with the accelerated test as mentioned above. As a result, the crystalline aluminosilicate was found to have a water resistance such that the concentration of Si ions dissolved out in water by hydrolysis was only 38 ppm.

Referential Example 23

128 g of water glass (sodium silicate) {JIS K1408, No. 3 ($SiO_2$ content: 28 to 30% by weight, $Na_2O$ content: 9 to 10% by weight)} was dissolved in 120 g of water to thereby obtain a solution (this solution is referred to as "solution A"). 3.9 g of aluminum sulfate octadecahydrate and 4 g of sulfuric acid were dissolved in 40 g of water to thereby obtain a solution (this solution is referred to as "solution B"). 20 g of 1,3-dimethylurea was dissolved in 80 g of water to thereby obtain a solution (this solution is referred to as "solution C"). 1.2 mmol of boron trioxide was dissolved in 20 g of water to thereby obtain a solution (this solution is referred to as "solution D"). Solutions B, C and D were mixed with solution A while vigorously agitating solution A using a homogenizer, and the agitation was conducted for 1 hour to thereby obtain a gel. The obtained gel was heated at 150° C. for 40 hours while agitating at a circumferential speed of 2 m/sec, to thereby crystallize the gel.

The resultant crystallized substance was subjected to filtration, followed by washing with water. The washed substance was dried at 120° C. for 5 hours, and calcined in air at 500° C. for 5 hours to thereby remove organic substances. Subsequently, the calcined substance was subjected to ion exchange in an aqueous 1N nitric acid solution for 8 hours, and subjected to filtration, followed by washing with water. The washed substance was dried at 120° C. for 6 hours to thereby obtain a crystalline aluminoborosilicate in a proton form.

The obtained crystalline aluminoborosilicate was analyzed with respect to the X-ray diffraction pattern thereof and, as a result, it was identified as a ZSM-5 zeolite analogue. Also, the crystalline aluminoborosilicate was subjected to X-ray fluorescence analysis, and the acid content thereof was measured by the piridine adsorption method. From the results of the X-ray fluorescence analysis and the measured acid content, it was found that the crystalline aluminoborosilicate in a oxidized form thereof has a composition represented by the following formula: $0.32H_2O.10SiO_2.Al_{2/3}O.0.16B_{2/3}O$.

The water resistance of crystalline aluminoborosilicate was evaluated in accordance with the accelerated test as mentioned above. As a result, the crystalline aluminoborosilicate was found to have a water resistance such that the concentration of Si ions dissolved out in water by hydrolysis was only 32 ppm.

Referential Example 24

AZ-1 zeolite in a proton form was obtained in substantially the same manner as described in Unexamined Japanese Patent Application Laid-Open Specification No. 59-128210 (composition formula: $0.3H_2O.10SiO_2.Al_{2/3}O$; and specific surface area: 331 m²/g). The water resistance of the resultant AZ-1 zeolite was evaluated in accordance with the accelerated test as mentioned above. As a result, the zeolite was found to have a water resistance such that the concentration of Si ions dissolved out in water by hydrolysis was only 40 ppm.

Referential Example 25

The water resistance of Y type zeolite (HSZ-320HOA, manufactured and sold by Tosoh Corp., Japan; composition formula: $0.32Na_2O.1.6SiO2.Al_{2/3}O$; and specific surface area: 613 m²/g) was evaluated in accordance with the accelerated test as mentioned above. As a result, the Y type zeolite was found to have a water resistance such that the concentration of Si ions dissolved out in water by hydrolysis was only 43 ppm.

Referential Example 26

ZSM-11 zeolite in a proton form was obtained in substantially the same manner as described in U.S. Pat. No. 3,709,979 (composition formula: $0.3H_2O.7SiO_2.Al_{2/3}O$; and specific surface area: 325 m²/g). The water resistance of the resultant ZSM-11 zeolite was evaluated in accordance with the accelerated test as mentioned above. As a result, the zeolite was found to have a water resistance such that the concentration of Si ions dissolved out in water by hydrolysis was only 87 ppm.

Referential Example 27

β zeolite (C-806β, manufactured and sold by PQ Corporation, U.S.A.) was subjected to ion exchange to thereby obtain a zeolite in a proton form (composition formula: $0.3H_2O.10SiO_2.Al_{2/3}O$; and specific surface area: 515 m²/g). The water resistance of the resultant β zeolite was evaluated in accordance with the accelerated test as mentioned above. As a result, the zeolite was found to have a water resistance such that the concentration of Si ions dissolved out in water by hydrolysis was only 48 ppm.

Referential Example 28

The water resistance of mordenite type zeolite (HSZ-630HOA, manufactured and sold by Tosoh Corp., Japan; composition formula: $0.3H_2O.5SiO_2.Al_{2/3}O$; and specific surface area: 613 m²/g) was evaluated in accordance with the accelerated test as mentioned above. As a result, the zeolite was found to have a water resistance out in water by hydrolysis was only 43 ppm.

EXAMPLE 70

Substantially the same procedure for preparing a catalyst intermediate as in Example 36 was repeated, except that ZSM-5 zeolite was used as a carrier, that bismuth nitrate pentahydrate was used instead of the thallium acetate, and that the lead nitrate was used in an amount of 4.09 parts by weight (i.e., 2.56 parts by weight in terms of lead) and the bismuth nitrate pentahydrate was used in an amount of 0.53 parts by weight (i.e., 0.23 parts by weight in terms of lead), to thereby obtain a catalyst intermediate $Pd^{5.0}Pb^{2.56}Bi^{0.23}$/ZSM-5. The obtained catalyst intermediate was subjected to activation treatment and a treatment for controlling the surface structure in substantially the same manner as in Example 11. The resultant catalyst was analyzed with respect to the Pd/Pb atomic ratio thereof, the diffraction angle ($2\theta$) in the powder X-ray diffraction pattern thereof at which the maximum intensity peak was exhibited, and the ratio of the total intensity of two peaks ascribed to metallic palladium 3d electrons to the intensity of a peak ascribed to metallic lead 4f(7/2) electron which is multiplied by 1.75 in the X-ray photoelectron spectrum thereof, by the methods as mentioned above. As a result, it was found that the catalyst had a Pd/Pb atomic ratio of 3/1.03 and exhibited a maximum intensity peak at a diffraction angle ($2\theta$) of 38.613°, and that the ratio of the total intensity of two peaks ascribed to metallic palladium 3d electrons to the intensity of a peak ascribed to metallic lead 4f(7/2) electron which is multiplied by 1.75 of the catalyst was 1/0.51.

Substantially the same procedure for producing MMA as in Example 11 was repeated except that the above-obtained catalyst was used, and analysis was made with respect to the reaction mixture which was withdrawn from the outlet of the reactor 1,000 hours after the start of the reaction. As a result, it was found that the conversion of methacrolein was 62.6%, the selectivity for MMA was 90.9%, and the selectivity for propylene as a by-product was 1.16%, and that methyl formate was by-produced in an amount of 0.038 mol/mol of MMA. The reaction mixture was also analyzed by ICP and, as a result, it was found that no Pd ions were detected (that is, the concentration of Pd ions was below the detection limit) and each of the concentrations of Si ions and Al ions was 1 ppm or less. After completion of the 1,000-hour reaction, a portion of the catalyst was taken out from the reactor, and observed under SEM. As a result, almost no change in the catalyst was observed.

EXAMPLE 71

A reaction for producing MMA was continuously conducted for 1,000 hours in substantially the same manner as in Example 11 using the catalyst obtained in Example 11 {the Pd/Pb atomic ratio: 3/1.08; the diffraction angle ($2\theta$) for the maximum intensity peak: 38.612°; and the ratio of the total intensity of two peaks ascribed to metallic palladium 3d electrons to the intensity of a peak ascribed to metallic lead 4f(7/2) electron which is multiplied by 1.75: 1/0.49}, except that the lead acetate was added to the reaction system so that the lead concentration of the reaction system became 20 ppm. After a 1,000-hour reaction, analysis was made with respect to the reaction mixture withdrawn from the outlet of the reactor, and the results of the analysis were compared with the results of the analysis of the reaction mixture which was obtained 200 hours after the start of the reaction. As a result, it was found that there was no significant change with respect to the results of the MMA-producing reaction. With respect to the reaction mixture which was obtained 1,000 hours after the start of the reaction, the conversion of methacrolein was 61.7%, the selectivity for MMA was 91.5%, and the selectivity for propylene as a by-product was 1.31%, and that methyl formate was by-produced in an amount of 0.043 mol/mol of MMA. The reaction mixture obtained 1,000 hours after the start of the reaction was also analyzed by ICP and, as a result, it was found that no Pd ions were detected (that is, the concentration of Pd ions was below the detection limit) and each of the concentrations of Si ions and Al ions was 1 ppm or less. Further, after completion of the 1,000-hour reaction, a portion of the catalyst was taken out from the reactor, and observed under SEM. As a result, almost no change in the catalyst was observed.

Comparative Example 17

Substantially the same procedure as in Example 71 was repeated, except that the lead acetate was not added to the reaction system. After a 1,000-hour reaction, analysis was made with respect to the reaction mixture withdrawn from the outlet of the reactor, and the results of the analysis were compared with the results of the analysis of the reaction mixture which was obtained 200 hours after the start of the reaction. As a result, it was found that, with respect to the reaction mixture which was obtained 200 hours after the start of the reaction, the conversion of methacrolein was 60.3%, the selectivity for MMA was 88.6%, and the selectivity for propylene as a by-product was 3.15%, and that methyl formate was by-produced in an amount of 0.038 mol/mol of MMA. It was also found that, with respect to the reaction mixture which was obtained 1,000 hours after the start of the reaction, the conversion of methacrolein was 54.8%, the selectivity for MMA was 83.2%, and the selectivity for propylene as a by-product was 7.80%, and that methyl formate was by-produced in an amount of 0.029 mol/mol of MMA. The reaction mixture obtained 1,000 hours after the start of the reaction was also analyzed by ICP and, as a result, it was found that no Pd ions were detected (that is, the concentration of Pd ions was below the detection limit) and each of the concentrations of Si ion and Al ion was 1 ppm or less. Further, after completion of the 1,000-hour reaction, a portion of the catalyst was taken out from the reactor, and observed under SEM. As a result, almost no change in the catalyst was observed.

EXAMPLES 72 to 76

In Examples 72 to 76, reactions for producing MMA were individually conducted in substantially the same manner as in Example 71, wherein the catalysts shown in Table 9, and conditions for achieving the oxygen partial pressures at the outlets of the reactors and Pb concentrations of the reaction system shown in Table 9, were individually employed. Results of the MMA-producing reactions are also shown in Table 9.

TABLE 9

| Examples | Catalyst | Carrier | Oxygen partial pressure (kg/cm$^2$) | Pb concentration of the reaction system (ppm) | Reaction period (hr) | | | | Amount of methyl formate produced (mol/mol of MMA) | Pd ion concentration of reaction mixture (ppm) | Si ion concentration of reaction mixture (ppm) | Al ion concentration of reaction mixture (ppm) | Result of the observation by SEM |
|---|---|---|---|---|---|---|---|---|---|---|---|---|---|
| | | | | | | Conversion of methacrolein (%) | Selectivity for MMA (%) | Selectivity for propylene (%) | | | | | |
| Example 72 | Catalyst obtained in Example 16 | SiO$_2$—Al$_2$O$_3$ | 0.38 | 100 | 1,000 | 63.5 | 91.6 | 0.96 | 0.077 | 0.1 or less | 1 or less | 1 or less | excellent |
| Example 73 | Catalyst obtained in Example 14 | SiO$_2$ | 0.1 | 2 | 2,000 | 63.9 | 91.2 | 1.29 | 0.044 | 0.1 or less | 6 | | partial cracking and chipping |
| Example 74 | Catalyst obtained in Example 15 | Al$_2$O$_3$ | 0.77 | 200 | 500 | 70.8 | 90.6 | 1.76 | 0.066 | 0.6 | | 5 | partial cracking and chipping |
| | | | | | | Conversion of benzaldehyde (%) | Selectivity for methyl benzoate (%) | | | | | | |
| Example 75 | Catalyst obtained in Example 7 | SiO$_2$—Al$_2$O$_3$—MgO | 0.3 | 40 | 1,000 | 62.8 | 91.4 | | 0.051 | 0.1 or less | 1 or less | 1 or less | excellent |
| | | | | | | Conversion of acrolein (%) | Selectivity for methyl acrylate (%) | Selectivity for ethylene (%) | | | | | |
| Example 76 | Catalyst obtained in Example 8 | SiO$_2$—Al$_2$O$_3$—MgO | 0.9 | 350 | 100 | 68.3 | 90.7 | 1.88 | 0.11 | 0.1 or less | 0.1 or less | 1 or less | excellent |

EXAMPLE 77

Substantially the same procedure for effecting the activation treatment and surface structure-controlling treatment of the catalyst intermediate as in Example 1 was repeated, except that the reaction for producing MMA was conducted at a methacrolein concentration of the reaction system of 10% by weight, and at a reaction temperature of 40° C. 10 Hours after the start of the reaction, the reaction mixture withdrawn from the outlet of the reactor was analyzed. As a result, it was found that the conversion of methacrolein was 44.8%, the selectivity for MMA was 93.8%, and the selectivity for propylene as a by-product was 0.31%, and that methyl formate was by-produced in an amount of 0.012 mol/mol of MMA. It was also found that the productivity of MMA was 0.132 {MMA(g)/g of catalyst·hr}.

EXAMPLE 78

Substantially the same procedure for effecting the activation treatment and surface structure-controlling treatment of the catalyst intermediate as in Example 11 was repeated, except that the catalyst intermediate obtained in Referential Example 1 was used, and that, in the surface structure-controlling treatment (which was conducted for a period of from 50 hours to 100 hours after the start of the activation treatment), the lead concentration of the reaction system was changed to 10 ppm. After completion of the activation treatment and surface structure-controlling treatment (i.e., 100 hours after the start of the activation of the catalyst intermediate), the resultant catalyst was taken out from the outlet of the reactor and analyzed by the methods as mentioned above. As a result, it was found that the catalyst had a Pd/Pb atomic ratio of 3/1.02 and exhibited a maximum intensity peak at a diffraction angle (2θ) of 38.609° in the powder X-ray diffraction pattern thereof, and that the ratio of the total intensity of two peaks ascribed to metallic palladium 3d electrons to the intensity of a peak ascribed to metallic lead 4f(7/2) electron which is multiplied by 1.75 in the X-ray photoelectron spectrum of the catalyst was 1/0.32. Using the catalyst, a reaction for producing MMA was conducted in substantially the same manner as in Example 11. 10 Hours after the start of the reaction, the resultant reaction mixture withdrawn from the outlet of the reactor was analyzed. As a result, it was found that the conversion of methacrolein was 60.9%, the selectivity for MMA was 90.2%, and the selectivity for propylene as a by-product was 1.93%, and that methyl formate was by-produced in an amount of 0.032 mol/mol of MMA.

Referential Example 29

Aluminum nitrate and magnesium nitrate were dissolved in an aqueous silica sol {Snowtex N-30 ($SiO_2$ content: 30% by weight), manufactured and sold by Nissan Chemical Industries, Ltd., Japan} so that the Al/(Si+Al) proportion became 10 mol % and the Mg/(Si+Mg) proportion became 10 mol %. The resultant solution was subjected to spray drying by means of a spray dryer at 130° C., thereby obtaining particles having an average particle diameter of 60 μm. The obtained particles were calcined in air at 300° C. for 2 hours and subsequently at 600° C. for 3 hours, thereby obtaining a carrier for a catalyst. To the obtained carrier were added an aqueous solution of palladium chloride (15% by weight) and sodium chloride (10% by weight) so that the amount of palladium chloride contained in the resultant mixture became 5 parts by weight in terms of Pd, relative to 100 parts by weight of the carrier. The resultant mixture was stirred at 60° C. for 1 hour, thereby obtaining a carrier which adsorbed almost all of the palladium chloride thereon. Thus, a composition $Pd^{5.0}/SiO_2$—$Al_2O_3$—MgO (hereinafter, frequently referred to as "catalyst precursor") was obtained.

EXAMPLE 79

A 30-liter autoclave was charged with 2 kg of the catalyst precursor prepared in Referential Example 29, 20 liters of an aqueous 6% by weight solution of sodium acetate trihydrate, lead acetate in an amount which corresponds to a lead amount satisfying the Pd/Pb atomic ratio of 3/1.27 in terms of the ratio of the amount of palladium in the catalyst precursor to the amount of lead charged above as the lead acetate, and an aqueous formaldehyde in an amount such that the molar ratio of the formaldehyde to the palladium of the catalyst precursor became 10/1. The resultant mixture was stirred at 90° C. for 1 hour, thereby effecting a reduction treatment of the catalyst precursor under the above conditions. The resultant catalyst was analyzed by the methods as mentioned above. As a result, it was found that the catalyst had a Pd/Pb atomic ratio of 3/1.25 and exhibited a maximum intensity peak at a diffraction angle (2θ) of 38.601° in the powder X-ray diffraction pattern thereof, and that the ratio of the total intensity of two peaks ascribed to metallic palladium 3d electrons to the intensity of a peak ascribed to metallic lead 4f(7/2) electron which is multiplied by 1.75 in the X-ray photoelectron spectrum of the catalyst was 1/0.49.

A stainless, external circulation type bubble column reactor, which was equipped with a separator for a catalyst and had a volume of 1.2 liters for a liquid phase, was charged with 240 g of the catalyst. A reaction for producing MMA was conducted as follows. A 36.7% by weight solution of methacrolein in methanol, in which lead acetate had been dissolved in an amount such that the lead concentration of the resultant reaction system became 20 ppm by weight, and a 2 to 4% by weight solution of NaOH in methanol were continuously fed to the reactor at 0.54 liter/hr and at 0.06 liter/hr, respectively (the methacrolein concentration of the reaction system consisting of the above-mentioned two different solutions was about 33% by weight), while introducing air to the reactor so that the oxygen concentration at the outlet of the reactor became 4.0% by volume (which is equivalent to the oxygen partial pressure of 0.20 kg/cm²), to effect a reaction for producing MMA. The reaction was conducted at a temperature of 80° C. under a pressure of 5 kg/cm² for 10 hours. The concentration of NaOH in the above-mentioned methanol solution was controlled so that the reaction system had a pH of 7.1. The reaction mixture obtained by the above reaction was continuously withdrawn by overflowing from the outlet of the reactor. Analysis was made with respect to the reaction mixture which was withdrawn from the outlet of the reactor 10 hours after the start of the reaction. As a result, it was found that the conversion of methacrolein was 61.8%, the selectivity for MMA was 91.8%, and the selectivity for propylene as a by-product was 1.2%, and that methyl formate was by-produced in an amount of 0.046 mol/mol of MMA.

Comparative Example 18

To the carrier obtained in Referential Example 29 were added an aqueous solution of palladium chloride (15% by weight) and sodium chloride (10% by weight) and an aqueous solution of lead nitrate (13% by weight) so that the amounts of palladium chloride and lead nitrate contained in the resultant mixture became 5.0 parts by weight in terms of Pd and 4.2 parts by weight in terms of Pb, respectively, relative to 100 parts by weight of the carrier. The resultant mixture was stirred at room temperature for 1 hour, thereby obtaining a carrier having almost all of the palladium chloride and lead nitrate adsorbed thereon. Thus, a composition $Pd^{5.0}Pb^{4.2}/SiO_2$—$Al_2O_3$—MgO (hereinafter, frequently referred to as "catalyst precursor") was obtained.

A 30-liter autoclave was charged with 2 kg of the obtained catalyst precursor, and an aqueous formaldehyde in an amount such that the molar ratio of the formaldehyde to the palladium of the catalyst precursor became 10/1. The resultant mixture was stirred at 90° C. for 1 hour, thereby reducing the palladium chloride and lead acetate contained in the catalyst precursor.

The resultant catalyst was analyzed by the methods as mentioned above. As a result, it was found that the catalyst had a Pd/Pb atomic ratio of 3/1.25 and exhibited a maximum intensity peak at a diffraction angle (2θ) of 38.891° in the powder X-ray diffraction pattern thereof, and that the ratio of the total intensity of two peaks ascribed to metallic palladium 3d electrons to the intensity of a peak ascribed to metallic lead 4f(7/2) electron which is multiplied by 1.75 in the X-ray photoelectron spectrum of the catalyst precursor was 1/0.49.

Using this catalyst, a reaction for producing MMA was conducted in substantially the same manner as in Example 79. 10 Hours after the start of the reaction, the reaction mixture withdrawn from the outlet of the reactor was analyzed. As a result, it was found that the conversion of methacrolein was 58.2%, the selectivity for MMA was 84.6%, and the selectivity for propylene as a by-product was 6.3%, and that methyl formate was by-produced in an amount of 0.178 mol/mol of MMA.

Comparative Example 19

A catalyst was obtained from the catalyst precursor prepared in Referential Example 29, in substantially the same manner as in Example 79, except that the lead acetate was used in an amount which corresponds to a lead amount satisfying the Pd/Pb atomic ratio of 3/1.95 in terms of palladium in the catalyst precursor to the amount of lead charged as the lead acetate. The obtained catalyst was analyzed by the methods as mentioned above. As a result, it was found that the catalyst had a Pd/Pb atomic ratio of 3/1.92 and exhibited a maximum intensity peak at a diffraction angle (2θ) of 38.623° in the powder X-ray diffraction pattern thereof, and that the ratio of the total intensity of two peaks ascribed to metallic palladium 3d electrons to the intensity of a peak ascribed to metallic lead 4f(7/2) electron which is multiplied by 1.75 in the X-ray photoelectron spectrum of the catalyst was 1/1.23.

Using this catalyst, a reaction for producing MMA was conducted in substantially the same manner as in Example 79. 10 Hours after the start of the reaction, the reaction mixture withdrawn from the outlet of the reactor was analyzed. As a result, it was found that the conversion of methacrolein was 57.8%, the selectivity for MMA was 87.3% and the selectivity for propylene as a by-product was 1.9%, and that methyl formate was by-produced in an amount of 0.213 mol/mol of MMA.

Comparative Example 20

A catalyst was obtained from the catalyst precursor prepared in Referential Example 29, in substantially the same manner as in Example 79, except that the lead acetate was used in an amount which corresponds to a lead amount satisfying the Pd/Pb atomic ratio of 3/1.55 in terms of the ratio of the amount of palladium in the catalyst precursor to the amount of lead charged as the lead acetate, and that the sodium acetate trihydrate was not used. The obtained catalyst was analyzed by the methods as mentioned above. As a result, it was found that the catalyst had a Pd/Pb atomic ratio of 3/1.58 and exhibited a maximum intensity peak at a diffraction angle (2θ) of 38.750° in the powder X-ray diffraction pattern thereof, and that the ratio of the total intensity of two peaks ascribed to metallic palladium 3d electrons to the intensity of a peak ascribed to metallic lead 4f(7/2) electron which is multiplied by 1.75 in the X-ray photoelectron spectrum of the catalyst was 1/0.75.

Using this catalyst, a reaction for producing MMA was conducted in substantially the same manner as in Example 79. 10 Hours after the start of the reaction, the reaction mixture withdrawn from the outlet of the reactor was analyzed. As a result, it was found that the conversion of methacrolein was 57.8%, the selectivity for MMA was 85.3% and the selectivity for propylene as a by-product was 5.1%, and that methyl formate was by-produced in an amount of 0.129 mol/mol of MMA.

EXAMPLE 80

A 30-liter autoclave was charged with 2 kg of the catalyst precursor prepared in Referential Example 29, 20 liters of an aqueous 6% by weight solution of sodium acetate trihydrate and lead nitrate in an amount which corresponds to a lead amount satisfying the Pd/Pb atomic ratio of 3/1.19 in terms of the ratio of the amount of palladium in the catalyst precursor to the amount of lead charged above as the lead acetate. The resultant mixture was stirred at 200° C. for 1 hour, while feeding a nitrogen gas containing 2% by volume of hydrogen to the reactor at 5 N liters/min, thereby effecting a reduction treatment of the catalyst precursor under these conditions. The resultant catalyst was analyzed by the methods as mentioned above. As a result, it was found that the catalyst had a Pd/Pb atomic ratio of 3/1.18 and exhibited a maximum intensity peak at a diffraction angle (2θ) of 38.697° in the powder X-ray diffraction pattern thereof, and that the ratio of the total intensity of two peaks ascribed to metallic palladium 3d electrons to the intensity of a peak ascribed to metallic lead 4f(7/2) electron which is multiplied by 1.75 in the X-ray photoelectron spectrum of the catalyst was 1/0.72.

Using this catalyst, a reaction for producing MMA was conducted in substantially the same manner as in Example 79. 10 Hours after the start of the reaction, the reaction mixture withdrawn from the outlet of the reactor was analyzed. As a result, it was found that the conversion of methacrolein was 55.2%, the selectivity for MMA was 88.6% and the selectivity for propylene as a by-product was 2.3%, and that methyl formate was by-produced in an amount of 0.104 mol/mol of MMA.

Referential Example 30

1,000 g of a silica gel (Cariact 10, manufactured and sold by Fuji Silysia Chemical, Ltd., Japan) was added to 2,000 ml of an aqueous solution containing 50.3 g of potassium acetate, and the resultant mixture was stirred on a boiling water bath to thereby impregnate the silica gel with the aqueous potassium acetate solution, followed by drying. The resultant dried substance was calcined at 500° C. for 3 hours to thereby obtain a calcined substance. On the other hand, 500 ml of an aqueous solution containing 83 g of palladium chloride and 28 g of sodium chloride was added to an aqueous solution containing 34 g of lead nitrate, and to the resultant mixture was added water in an amount such that the total volume became 10 liters. To the resultant mixture was added the above-obtained calcined substance, and the resultant mixture was stirred at room temperature for 2 hours, thereby obtaining a catalyst precursor having supported thereon palladium chloride, lead nitrate and potassium acetate in amounts of 5.0 parts by weight in terms of Pd, 2.13 parts by weight in terms of Pb and 2.0 parts by weight in terms of K, respectively, relative to 100 parts by weight of the silica gel. The obtained catalyst precursor was analyzed by the method as mentioned above. As a result, it was found that the catalyst precursor had a Pd/Pb atomic ratio of 3/0.66.

EXAMPLES 81 to 85

Catalysts, which were individually obtained by subjecting the catalyst precursor prepared in Referential Example 30 to reduction treatment under reduction conditions indicated in table 10, were analyzed by the methods as mentioned above. Further, using the obtained catalysts, reactions for producing MMA were individually conducted in substantially the same manner as in Example 79. The Pd/Pb atomic ratio of each of the catalysts, the diffraction angle (2θ) for a maximum intensity peak in the powder X-ray diffraction pattern of each of the catalysts, and the ratio of the total intensity of two peaks ascribed to metallic palladium 3d electrons to the intensity of a peak ascribed to metallic lead 4f(7/2) electron which is multiplied by 1.75 in the X-ray photoelectron spectrum of each of the catalysts are shown in Table 10 below, together with the respective results of analyses of the reaction mixtures obtained 10 hours after the start of the MMA-producing reactions.

TABLE 10

| | Conditions for activation | | | | | | Activated catalyst | | | | | | Amount of |
|---|---|---|---|---|---|---|---|---|---|---|---|---|---|
| | | | | | Fatty acid | | | Diffraction angle (2θ) for | Intensity ratio of peaks | Conversion of | Selectivity | Selectivity | methyl formate |
| Examples | Reductant/ solvent | Reductant/Pd molar ratio | Pd/Pb (added lead) atomic ratio (*1) | Temperature (° C.) | Period (hr) | Type | Amount (% by weight) | Pd/Pb atomic ratio | maximum intensity peak | (metallic Pd/metallic Pb)*2 | methacrolein (%) | tivity for MMA (%) | for propylene (%) | produced (mol/mol of MMA) |
| Example 81 | hydrazine/ water | 3.0 | 3/0.20 | 80 | 4 | — | — | 3/0.86 | 38.697° | 1/0.66 | 57.6 | 89.6 | 2.4 | 0.053 |
| Example 82 | sodium formate/ water | 5.0 | 3/0.49 | 90 | 1 | sodium acetate | 10 | 3/1.15 | 38.591° | 1/0.53 | 61.1 | 91.3 | 1.2 | 0.062 |
| Example 83 | aqueous formaldehyde/ water | 2.1 | 3/0.53 | 90 | 2 | propionic acid tate | 5 | 3/1.19 | 38.633° | 1/0.44 | 62.3 | 90.1 | 1.1 | 0.042 |
| Example 84 | aqueous formaldehyde/ methanol | 1.0 | 3/0.46 | 160 | 0.5 | acetic acid | 4 | 3/1.12 | 38.621° | 1/0.37 | 61.8 | 91.1 | 0.9 | 0.044 |
| Example 85 | aqueous formaldehyde/ water | 10.0 | 3/0.61 | 90 | 1 | magnesium acetate | 4 | 3/1.27 | 38.591° | 1/0.42 | 62.9 | 91.2 | 1.1 | 0.051 |

Note:
*1) The Pd/Pb atomic ratio represents an atomic ratio of the palladium of the catalyst intermediate to the lead of the lead acetate monohydrate added to the reaction system.
*2) Ratio of the total intensity of two peaks ascribed to metallic palladium 3d electrons to the intensity of a peak ascribed to metallic lead 4f (7/2) electron which is multiplied by 1.75 in the X-ray photoelectron spectrum.

EXAMPLE 86

A 30-liter autoclave was charged with 2 kg of the catalyst precursor prepared in Referential Example 30 and 20 liters of an aqueous 10% by weight solution of sodium acetate trihydrate. The resultant mixture was stirred at 90° C. for 1 hour. The resultant mixture was analyzed, and found to contain lead ions in a concentration of 750 ppm by weight. Subsequently, to the mixture were further added lead acetate in the amount which corresponds to a supplementary lead amount necessary for changing the Pd/Pb atomic ratio (3/0.66) of the catalyst precursor to 3/1.28 and an aqueous formaldehyde in an amount such that the molar ratio of the formaldehyde to the palladium of the catalyst precursor became 5/1. The resultant mixture was stirred at 90° C. for 1 hour, to thereby effect a reduction treatment of the catalyst precursor under the above conditions. The resultant catalyst was analyzed by the methods as mentioned above. As a result, it was found that the catalyst had a Pd/Pb atomic ratio of 3/1.27 and exhibited a maximum intensity peak at a diffraction angle (2θ) of 38.610° in the powder X-ray diffraction pattern thereof, and that the ratio of the total intensity of two peaks ascribed to metallic palladium 3d electrons to the intensity of a peak ascribed to metallic lead 4f(7/2) electron which is multiplied by 1.75 in the X-ray photoelectron spectrum of the catalyst was 1/0.39.

Two stainless, external circulation type bubble column reactors each as used in Example 79 (each of which reactors was equipped with a separator for a catalyst and had a volume of 1.2 liters for a liquid phase), were connected to provide a first stage reactor and a second stage reactor which were connected in series. Each of the first stage and second stage reactors was charged with 240 g of the above-obtained catalyst. Then, a series of reactions for producing MMA was conducted as follows. A 36.7% by weight solution of methacrolein in methanol, in which lead acetate had been dissolved so that the lead concentration of the resultant reaction system became 20 ppm by weight, and a 2 to 4% by weight solution of NaOH in methanol were continuously fed to the first stage reactor at 0.54 liter/hr and at 0.06 liter/hr, respectively (the methacrolein concentration of the reaction system consisting of the above-mentioned two different solutions was about 33% by weight), while introducing air to the first stage reactor so that the oxygen concentration at the outlet of the first stage reactor became 4.0% by volume (which is equivalent to the oxygen partial pressure of 0.20 kg/cm$^2$), to effect a reaction for producing MMA. The reaction was conducted at a temperature of 80° C. under a pressure of 5 kg/cm$^2$. The resultant reaction mixture containing the catalyst was continuously withdrawn by overflowing from the outlet of the first stage reactor and transferred to a liquid phase-solid phase separation zone, where a separation between the catalyst and the reaction mixture was effected. The separated catalyst was returned to the first stage reactor. The separated reaction mixture and a 2 to 4% by weight solution of NaOH in methanol were fed to the second stage reactor at 0.6 liter/hr and at 0.06 liter/hr, respectively. A gaseous phase withdrawn from the first stage reactor was fed to the second stage reactor while introducing fresh air to the second stage reactor so that the oxygen concentration at the outlet of the second stage reactor became 2.2% by volume (which is equivalent to the oxygen partial pressure of 0.11 kg/cm$^2$), to effect a reaction for producing MMA. The reaction was conducted at a temperature of 80° C. under a pressure of 4.6 kg/cm$^2$. The concentration of NaOH in the methanol solution fed to each of the first stage and second stage reactors was controlled so that the reaction system in each reactor had a pH of 7.1. The reaction mixture obtained in the second stage reactor was continuously withdrawn by overflowing from the outlet of the second stage reactor.

Analysis was made with respect to the reaction mixture which was withdrawn from the outlet of the second stage reactor 10 hours after the start of the two-stage reaction. As a result, it was found that the conversion of methacrolein was 84.9%, the selectivity for MMA was 91.4%, and the selectivity for propylene as a by-product was 1.1%, and that methyl formate was by-produced in an amount of 0.045 mol/mol of MMA.

EXAMPLE 87

A composition comprising a silica gel (Cariact 10, manufactured and sold by Fuji Silysia Chemical, Ltd. Japan) having supported thereon $\{Pd(NH_3)_4\}Cl_2$ in an amount of 5.0 parts by weight in terms of palladium, relative to 100 parts by weight of the silica gel, was obtained in substantially the same manner as in Example 36 (hereinafter, the obtained composition is frequently referred to simply as "catalyst precursor"). The catalyst precursor was subjected to reduction treatment in substantially the same manner as in Example 79, except that the reduction treatment was conducted under conditions such that lead acetate and thallium acetate were present in amounts of 3.96 parts by weight in terms of lead and 0.11 parts by weight in terms of thallium, respectively, based on 105 parts by weight of the catalyst precursor, instead of the lead acetate employed in the amount as described in Example 79. The resultant catalyst ($Pd^{5.0}Pb^{3.96}Tl^{0.11}/SiO_2$) was analyzed by the methods as mentioned above. As a result, it was found that the catalyst obtained had a Pd/Pb atomic ratio of 3/1.21 and exhibited a maximum intensity peak at a diffraction angle (2θ) of 38.620° in the powder X-ray diffraction pattern thereof, and that the ratio of the total intensity of two peaks ascribed to metallic palladium 3d electrons to the intensity of a peak ascribed to metallic lead 4f(7/2) electron which is multiplied by 1.75 in the X-ray photoelectron spectrum of the catalyst was 1/0.47.

Using 200 g of the catalyst, a reaction for producing MMA was conducted in substantially the same manner as in Example 79, except that lead acetate was added to the solution of methacrolein in methanol so that the lead concentration of the resultant reaction system became 10 ppm by weight. Analysis was made with respect to the reaction mixture which was withdrawn from the outlet of the reactor 10 hours after the start of the reaction. As a result, it was found that the conversion of methacrolein was 62.4%, the selectivity for MMA was 91.2%, and the selectivity for propylene as a by-product was 1.2%, and that methyl formate was by-produced in an amount of 0.042 mol/mol of MMA.

EXAMPLE 88

A composition ($Pd^{5.0}Mg^{2.0}/Al_2O_3$) was prepared in substantially the same manner as in Example 37, except that the lead nitrate and the bismuth nitrate were not used (hereinafter, the obtained composition is frequently referred to simply as "catalyst precursor"). The obtained catalyst precursor was subjected to reduction treatment in substantially the same manner as in Example 79, except that lead nitrate and bismuth nitrate were used in amounts which respectively correspond to a lead amount and a bismuth amount which satisfy the Pd/Pb/Bi atomic ratio of 3/2.7/0.23 in terms of the ratio of the amount of palladium in the catalyst precursor to the amounts of lead and bismuth charged as the lead nitrate and bismuth nitrate, respectively, instead of only the lead acetate employed in the amount as described in Example 79. The resultant catalyst had a composition of $Pd^{5.0}Pb^{2.7}Bi^{0.23}Mg^{2.0}/Al_2O_3$. The catalyst was analyzed by the methods as mentioned above. As a result, it was found that the catalyst had a Pd/Pb atomic ratio of 3/1.24 and exhibited a maximum intensity peak at a diffraction angle (2θ) of 38.612° in the powder X-ray diffraction pattern thereof, and that the ratio of the total intensity of two peaks ascribed to metallic palladium 3d electrons to the intensity of a peak ascribed to metallic lead 4f(7/2) electron which is multiplied by 1.75 in the X-ray photoelectron spectrum of the catalyst was 1/0.52.

Using this catalyst, a reaction for producing MMA was conducted in substantially the same manner as in Example 87. Analysis was made with respect to the reaction mixture which was withdrawn from the reactor 10 hours after the start of the reaction. As a result, it was found that the conversion of methacrolein was 60.3%, the selectivity for MMA was 90.5%, and the selectivity for propylene as a by-product was 1.2%, and that methyl formate was by-produced in an amount of 0.052 mol/mol of MMA.

EXAMPLE 89

A reaction for producing methyl acrylate (MA) was conducted in substantially the same manner as described in Example 88, except that the catalyst obtained in Example 86 was used and that acrolein was used instead of the methacrolein. Analysis was made with respect to the reaction mixture which was withdrawn from the outlet of the reactor 10 hours after the start of the reaction. As a result, it was found that the conversion of acrolein was 58.4%, the selectivity for MA was 92.4%, and the selectivity for ethylene as a by-product was 1.0%, and that methyl formate was by-produced in an amount of 0.042 mol/mol of MA.

EXAMPLE 90

Substantially the same procedure as conducted for activating the catalyst intermediate (which had been prepared in Referential Example 5) in Example 39 was repeated, except that a nitrogen gas containing 8% by volume of isobutene gas was used instead of the nitrogen gas containing 8% by volume of methanol gas, and that the reduction treatment under flowing of the isobutene gas-containing nitrogen gas was conducted at 300° C., to thereby obtain an activated catalyst. The obtained activated catalyst had a Pd/Pb atomic ratio of 3/1.28 and exhibited a maximum intensity peak at a diffraction angle (2θ) of 38.618° in the powder X-ray diffraction pattern thereof, and the ratio of the total intensity of two peaks ascribed to metallic palladium 3d electrons to the intensity of a peak ascribed to metallic lead 4f(7/2) electron which is multiplied by 1.75 in the X-ray photoelectron spectrum of the activated catalyst was 1/0.351.

Using the activated catalyst, a reaction for producing MMA was conducted in substantially the same manner as in Example 39. Analysis was made with respect to the reaction mixture withdrawn from the outlet of the reactor 10 hours after the start of the reaction. As a result, it was found that the conversion of methacrolein was 61.0%, the selectivity for MMA was 91.1%, and the selectivity for propylene as a by-product was 1.1%, and that methyl formate was by-produced in an amount of 0.050 mol/mol of MMA.

EXAMPLE 91

Substantially the same procedure as conducted for preparing a catalyst intermediate and activating the prepared catalyst intermediate in Example 43 was repeated, except that a nitrogen gas containing 8% by volume of isobutene gas was used instead of the nitrogen gas containing 8% by volume of methanol gas, and that the reduction treatment under flowing of the isobutene gas-containing nitrogen gas was conducted at 300° C., to thereby obtain an activated catalyst. Analysis was made with respect to the obtained activated catalyst. As a result, it was found that the activated catalyst had a Pd/Pb atomic ratio of 3/1.31 and exhibited a maximum intensity peak at a diffraction angle (2θ) of 38.623° in the powder X-ray diffraction pattern thereof, and that the ratio of the total intensity of two peaks ascribed to metallic palladium 3d electrons to the intensity of a peak ascribed to metallic lead 4f(7/2) electron which is multiplied by 1.75 in the X-ray photoelectron spectrum of the activated catalyst was 1/0.308.

Using the activated catalyst, a reaction for producing MMA was conducted in substantially the same manner as in Example 42. Analysis was made with respect to the reaction mixture withdrawn from the outlet of the reactor 10 hours after the start of the reaction. As a result, it was found that the conversion of methacrolein was 61.8%, the selectivity for MMA was 90.1%, and the selectivity for propylene as a by-product was 1.1%, and that methyl formate was by-produced in an amount of 0.051 mol/mol of MMA.

EXAMPLE 92

Substantially the same procedure as in Referential Example 2 was repeated, except that the aqueous solution of lead nitrate was not used, to thereby obtain a catalyst intermediate containing the carrier having adsorbed thereon 5.0 parts by weight of palladium, relative to 100 parts by weight of the carrier. Thereafter, substantially he same procedure for the activation treatment of the obtained catalyst intermediate as in Example 7 was repeated, except that the amount of the lead acetate trihydrate used was changed to 90.5 g, and that the period for the activation treatment was changed to 100 hours, to thereby obtain an activated catalyst. The obtained activated catalyst had a Pd/Pb atomic ratio of 3/0.96 and exhibited the maximum intensity peak at a diffraction angle (2θ) of 38.688° in the powder X-ray diffraction pattern thereof.

Using the activated catalyst, substantially the same procedure for producing MMA as in Example 7 was repeated, and analysis was made with respect to the reaction mixture which was withdrawn from the outlet of the reactor 10 hours after the start of the reaction. As a result, it was found that the conversion of methacrolein was 58.2%, the selectivity for MMA was 90.1%, and the selectivity for propylene as a by-product was 2.03%, and that methyl formate was by-produced in an amount of 0.058 mol/mol of MMA.

EXAMPLE 93

Substantially the same procedure for the activation treatment of the catalyst intermediate as in Example 1 was repeated, except that the lead acetate was added to the reaction system for effecting the activation treatment so that the lead concentration of the reaction system became 200 ppm, and that the period for the activation treatment was changed to 200 hours, to thereby obtain an activated catalyst. The obtained activated catalyst had a Pd/Pb atomic ratio of 3/0.94 and exhibited the maximum intensity peak at a diffraction angle (2θ) of 38.693° in the powder X-ray diffraction pattern thereof.

Using the activated catalyst, substantially the same procedure for producing MMA as in Example 7 was repeated, and analysis was made with respect to the reaction mixture which was withdrawn from the outlet of the reactor 10 hours after the start of the reaction. As a result, it was found that the conversion of methacrolein was 57.8%, the selectivity for MMA was 89.7%, and the selectivity for propylene as a by-product was 2.35%, and that methyl formate was by-produced in an amount of 0.054 mol/mol of MMA.

Industrial Applicability

When a process for producing a carboxylic ester from an aldehyde, an alcohol and molecular oxygen is conducted in the presence of a catalyst which comprises a carrier having supported thereon palladium and lead in a Pd/Pb atomic ratio (S) of $3/0.7 \leq S \leq 3/1.3$, exhibiting a maximum intensity peak at a diffraction angle (2θ) in the range of from 38.55° to 38.70° in a powder X-ray diffraction pattern thereof, wherein the peak is ascribed to the (111) crystal face diffraction of a Pd—Pb intermetallic compound, a desired carboxylic ester can be produced with high selectivity, while suppressing the formation of by-products, even when the production is conducted under economically advantageous but severe reaction conditions, namely, under high reaction temperature and high aldehyde concentration conditions. Further, the catalyst of the present invention exhibits high mechanical strength and high water resistance. Furthermore, in the continuous production of a carboxylic ester using the catalyst of the present invention, stabilization of the catalyst can be effectively performed to thereby achieve a prolonged catalytic life, so that a desired carboxylic ester can be produced with high efficiency and in high yield for a prolonged period of time. The commercial value of the catalyst of the present invention is very high.

We claim:

1. A catalyst for use in producing a carboxylic ester from an aldehyde, an alcohol and molecular oxygen, which comprises a carrier having supported thereon palladium and lead in a Pd/Pb atomic ratio (S) of $3/0.7 \leq S \leq 3/1.3$, said catalyst exhibiting a maximum intensity peak at a diffraction angle (2θ) in the range of from 38.55° to 38.70° in a powder X-ray diffraction pattern thereof, wherein said peak is ascribed to the (111) crystal face diffraction of a Pd—Pb intermetallic compound.

2. The catalyst according to claim 1, exhibiting, in a spectrum obtained from said catalyst by X-ray photoelectron spectroscopy, a ratio of from 1/0.2 to 1/0.7 in terms of the {Pd3d(3/2)+Pd3d(5/2)}/{Pb4f(7/2)×1.75} ratio of the sum of respective intensities of two peaks respectively ascribed to the 3d(3/2) electron and the 3d(5/2) electron of metallic palladium to the intensity of a peak ascribed to the 4f(7/2) electron of metallic lead which is multiplied by 1.75.

3. The catalyst according to claim 1 or 2, wherein said carrier is an aluminum-containing silica composition comprising silica and alumina, which has an aluminum proportion of from 1 to 30 mol. %, based on the total molar amount of silicon and aluminum in said composition.

4. The catalyst according to claim 1 or 2, wherein said carrier comprises a silica-alumina-magnesia composition having silicon, aluminum and magnesium proportions of from 42 to 90 mol. %, from 5.5 to 38 mol. %, and from 4 to 38 mol. %, respectively, based on the total molar amount of said silicon, said aluminum and said magnesium.

5. The catalyst according to claim 1 or 2, wherein said carrier comprises a crystalline metallosilicate which, in the anhydride state and on a molar basis, has a composition represented by the following formula (1);

$$xM_{2/n}O \cdot ySiO_2 \cdot R_{2/w}O \qquad (1)$$

wherein:

M represents at least one cation having the valence of n;

R represents at least one metal having the valence of w, which is selected from metals belonging to Groups IB, IIB, IIIA, IIIB, IVA, IVB, VA, VB, VIB, VIIB and VIII of the short-form Periodic Table;

n is 1 or 2;

w is an integer of from 1 to 4;

x=0.3±0.1; and $0.5 \leq y \leq 500$.

6. A method for producing a catalyst of claim 1, which comprises subjecting a catalyst precursor comprising a carrier having supported thereon a reducible palladium compound or a mixture of a reducible palladium compound and a reducible lead compound to a reduction treatment with a reducing agent in a solvent in the presence of lead ions and at least one compound selected from the group consisting of a $C_1$–$C_5$ fatty acid, an alkali metal salt and an alkaline earth metal salt.

7. The method according to claim 6, wherein said reducible palladium compound is at least one salt selected from palladium salts of organic acids and inorganic acids, and said reducible lead compound is at least one salt selected from lead salts of organic acids and inorganic acids.

8. The method according to claim 6 or 7, wherein said alkali metal salt is an alkali metal salt of a $C_1$–$C_5$ fatty acid, and said alkaline earth metal salt is an alkaline earth metal salt of a $C_1$–$C_5$ fatty acid.

9. The method according to claim 6 or 7, wherein said reducing agent comprises at least one member selected from the group consisting of formaldehyde, formic acid, hydrazine, methanol and molecular hydrogen.

10. The method according to claim 6 or 7, wherein said solvent comprises at least one member selected from the group consisting of water and an alcohol.

11. A method for producing a catalyst of claim 1, which comprises subjecting a catalyst intermediate comprising a carrier having supported thereon palladium or a mixture of palladium and lead in a Pd/Pb atomic ratio (S) of $3/0 \leq S \leq 3/10$ to a reduction treatment with a reducing agent in the presence of lead ions in a solvent.

12. The method according to claim 11, wherein said reduction treatment is conducted in the presence of at least one compound selected from the group consisting of a $C_1$–$C_5$ fatty acid, an alkali metal salt of a $C_1$–$C_5$ fatty acid and an alkaline earth metal salt of a $C_1$–$C_5$ fatty acid.

13. The method according to claim 11 or 12, wherein said reducing agent comprises at least one member selected from the group consisting of formaldehyde, formic acid, hydrazine, methanol and molecular hydrogen.

14. The method according to claim 11 or 12, wherein said solvent comprises at least one member selected from the group consisting of water and an alcohol.

15. A method for producing a catalyst of claim 1, which comprises oxidizing a catalyst intermediate comprising a carrier having supported thereon palladium and lead in a Pd/Pb atomic ratio (S) of $3/0.7 \leq S \leq 3/1.3$ with a gaseous oxidizing agent and subsequently reducing the resultant oxidized catalyst intermediate with a gaseous reducing agent, wherein a sequence of the oxidation and the reduction is conducted at least once.

16. The method according to claim 15, wherein said gaseous oxidizing agent comprises molecular oxygen.

17. The method according to claim 15 or 16, wherein said gaseous reducing agent comprises at least one member selected from methanol gas, molecular hydrogen and $C_2$–$C_4$ olefin gas.

18. A method for producing a catalyst of claim 1, which comprises oxidizing a catalyst intermediate comprising a carrier having supported thereon palladium and lead in a Pd/Pb atomic ratio (S) of $3/1.3 \leq S \leq 3/10$ with a gaseous oxidizing agent and subsequently reducing the oxidized catalyst intermediate with a gaseous reducing agent, wherein a sequence of the oxidation and the reduction is conducted at least once; and, subsequent to said sequence of the oxidation and the reduction which sequence is conducted at least once, treating the resultant catalyst intermediate with a solution of at least one compound selected from the group consisting of a $C_1$–$C_5$ fatty acid, an alkali metal salt of a $C_1$–$C_5$ fatty acid and an alkaline earth metal salt of a $C_1$–$C_5$ fatty acid in a solvent.

19. The method according to claim 18, wherein said gaseous oxidizing agent comprises molecular oxygen.

20. The method according to claim 18 or 19, wherein said gaseous reducing agent comprises at least one member selected from methanol gas, molecular hydrogen and $C_2$–$C_4$ olefin gas.

21. The method according to claim 18 or 19, wherein said solvent comprises at least one member selected from the group consisting of water and an alcohol.

22. A method for producing a catalyst of claim 1, which comprises treating a catalyst intermediate comprising a carrier having supported thereon palladium and lead in a Pd/Pb atomic ratio (S) of $3/2.5 \leq S \leq 3/10$ with a solution of at least one compound selected from the group consisting of a $C_1$–$C_5$ fatty acid, an alkali metal salt of a $C_1$–$C_5$ fatty acid and an alkaline earth metal salt of a $C_1$–$C_5$ fatty acid in a solvent.

23. The method according to claim 22, wherein said solvent comprises at least one member selected from the group consisting of water and an alcohol.

24. A method for producing the catalyst of claim 1, which comprises reacting, in a reactor, a catalyst intermediate comprising a carrier having supported thereon palladium or a mixture of palladium and lead in a Pd/Pb atomic ratio (S) of $3/0 \leq S \leq 3/10$ with an alcohol or a mixture of an alcohol and an aldehyde in the presence of lead ions, wherein said reaction is conducted under conditions such that the partial pressure of oxygen at the outlet of the reactor is from 0 to 0.8 kg/cm².

25. A method for producing the catalyst of claim 2, which comprises reacting, in a reactor, a catalyst intermediate comprising a carrier having supported thereon palladium or a mixture of palladium and lead in a Pd/Pb atomic ratio (S) of $3/0 \leq S \leq 3/10$ with an alcohol or a mixture of an alcohol and an aldehyde in the presence of lead ions, wherein said reaction is conducted under conditions such that the partial pressure of oxygen at the outlet of the reactor is from 0 to 0.4 kg/cm².

26. A method for producing the catalyst of claim 2, which comprises reacting, in a reactor, the catalyst of claim 1 with an alcohol or a mixture of an alcohol and an aldehyde in the presence of lead ions, wherein said reaction is conducted under conditions such that the partial pressure of oxygen at the outlet of the reactor is from 0 to 0.8 kg/cm².

27. A method for continuously producing a carboxylic ester, which comprises continuously reacting an aldehyde, an alcohol and molecular oxygen in a reactor in the presence of the catalyst of claim 1, while adding to the reactor a substance capable of forming lead ions in a reaction system comprising said aldehyde, said alcohol and said molecular oxygen.

28. The method according to claim 27, wherein said continuous reaction is conducted under conditions such that the partial pressure of oxygen at the outlet of the reactor is 0.8 kg/cm² or less.

29. The method according to claim 27, wherein said molecular oxygen is in the form of air.

30. A method according to claim 27, wherein said aldehyde is selected from the group consisting of methacrolein, acrolein and a mixture thereof, and said alcohol is methanol.

* * * * *